US010195211B2

(12) United States Patent
Zhao et al.

(10) Patent No.: US 10,195,211 B2
(45) Date of Patent: *Feb. 5, 2019

(54) SOFT LOZENGE COMPOSITIONS

(71) Applicant: PATHEON SOFTGELS INC, High Point, NC (US)

(72) Inventors: YinYan Zhao, Greensboro, NC (US); Justin Hughey, Asheboro, NC (US); Jason Vaughn, Browns Summit, NC (US); Qi Fang, Oak Ridge, NC (US)

(73) Assignee: Patheon Softgels, Inc., High Point, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/795,846

(22) Filed: Oct. 27, 2017

(65) Prior Publication Data

US 2018/0078502 A1    Mar. 22, 2018

Related U.S. Application Data

(60) Division of application No. 15/293,535, filed on Oct. 14, 2016, now Pat. No. 9,867,834, which is a continuation-in-part of application No. 15/181,462, filed on Jun. 14, 2016, now Pat. No. 9,877,971.

(60) Provisional application No. 62/175,470, filed on Jun. 15, 2015.

(51) Int. Cl.
| | |
|---|---|
| *A61K 9/00* | (2006.01) |
| *A61K 9/20* | (2006.01) |
| *A61K 31/56* | (2006.01) |
| *A61K 45/06* | (2006.01) |
| *A61K 47/10* | (2017.01) |
| *A61K 31/167* | (2006.01) |

(52) U.S. Cl.
CPC ............ *A61K 31/56* (2013.01); *A61K 9/0056* (2013.01); *A61K 9/2013* (2013.01); *A61K 9/2018* (2013.01); *A61K 9/2031* (2013.01); *A61K 9/2063* (2013.01); *A61K 31/167* (2013.01); *A61K 45/06* (2013.01); *A61K 47/10* (2013.01)

(58) Field of Classification Search
CPC .. A61K 9/0056; A61K 9/2063; A61K 9/2018; A61K 9/2013; A61K 45/06; A61K 31/56; A61K 9/2031; A61K 31/167; A61K 47/10
See application file for complete search history.

(56) References Cited

U.S. PATENT DOCUMENTS

| | | | |
|---|---|---|---|
| 3,511,914 | A | 5/1970 | Wolkoff |
| 5,510,339 | A | 4/1996 | Gleich |
| 8,324,192 | B2 | 12/2012 | Bastian |
| 8,497,258 | B2 | 7/2013 | Hill |
| 8,679,545 | B2 | 3/2014 | Bastian |
| 8,771,729 | B2 | 7/2014 | Perrett |
| 8,865,692 | B2 | 10/2014 | Phillips |
| 8,975,243 | B2 | 3/2015 | Bastian |
| 9,050,368 | B2 | 6/2015 | Phillips |
| 9,119,863 | B2 | 9/2015 | Hill |
| 2009/0123390 | A1 | 5/2009 | Hill |
| 2009/0123550 | A1 | 5/2009 | Deshmukh |
| 2009/0123551 | A1 | 5/2009 | Phillips |
| 2009/0131386 | A1 | 5/2009 | Phillips |
| 2009/0137540 | A1 | 5/2009 | Phillips |
| 2009/0143343 | A1 | 6/2009 | Hill |
| 2009/0149433 | A1 | 6/2009 | Phillips |
| 2009/0181099 | A1 | 7/2009 | Hill |
| 2009/0191275 | A1 | 7/2009 | Hill |
| 2009/0264392 | A1 | 10/2009 | Warndahl |
| 2010/0016754 | A1 | 1/2010 | Cohen |
| 2011/0002998 | A1 | 1/2011 | Klein |
| 2011/0081411 | A1 | 4/2011 | Perrett |
| 2011/0097401 | A1 | 4/2011 | Simpson |
| 2012/0164080 | A1 | 6/2012 | Phillips |
| 2012/0282335 | A1 | 11/2012 | Lai |
| 2013/0096096 | A1 | 4/2013 | Bastian |
| 2013/0296286 | A1 | 11/2013 | Hill |
| 2014/0187523 | A1 | 7/2014 | Hill |
| 2014/0287051 | A1 | 9/2014 | Perrett |
| 2014/0303131 | A1 | 10/2014 | Perrett |
| 2015/0005270 | A1 | 1/2015 | Phillips |

OTHER PUBLICATIONS

Alexander et al., "Swallowed Fluticasone Improves Histologic but Not Symptomatic Response of Adults with Eosinophilic Esophagitis," Clinical Gastroenterology and Hepatology 10: 742-749 (2012).
Amim et al., "Eosinophilic Esophagitis—Treatment of Eosinophilic Esophagitis with Drugs: Corticosteroids," Digestive Diseases 32: 126-129 (2014).
Carr and Watson, "Eosinophilic esophagitis," Allergy, Asthma & Clinical Immunology 7(Suppl 1): S8 (2011).
Gonsalves et al., "Elimination Diet Effectively Treats Eosinophilic Esophagitis in Adults; Food Reintroduction Identifies Causative Factors," Gastroenterology142: 1451-1459 (2012).
Konikoff et al., "A Randomized, Double-Blind, Placebo-Controlled Trial of Fluticasone Propionate for Pediatric Eosinophilic Esophagitis," Gastroenterology 131: 1381-1391 (2006).
Noel et al., "Clinical and Immunopathologic Effects of Swallowed Fluticasone for Eosinophilic Esophagitis," Clinical Gastroenterology and Hepatology 2: 568-575 (2004).

(Continued)

*Primary Examiner* — Snigdha Maewall
(74) *Attorney, Agent, or Firm* — Brinks Gilson & Lione

(57) ABSTRACT

Described herein are topical, non-systemic, slow releasing oral pharmaceutical compositions, methods for making the same, and methods for treating subjects in need thereof with such compositions. In particular, the oral composition provides topical, non-systemic administration of one or more active pharmaceutical ingredients to the oral cavity and upper gastrointestinal track, including the esophagus. In one embodiment, the pharmaceutical composition provides topical corticosteroids to the esophagus and oral cavity.

20 Claims, 1 Drawing Sheet

(56) References Cited

OTHER PUBLICATIONS

Schaefer et al., "Comparison of Oral Prednisone and Topical Fluticasone in the Treatment of Eosinophilic Esophagitis: A Randomized Trial in Children," Clinical Gastroenterology and Hepatology 6: 165-173 (2008).
Teitelbaum et al., "Eosinophilic Esophagitis in Children: Immunopathological Analysis and Response to Fluticasone Propionate," Gastroenterology 122: 1216-1225 (2002).

A
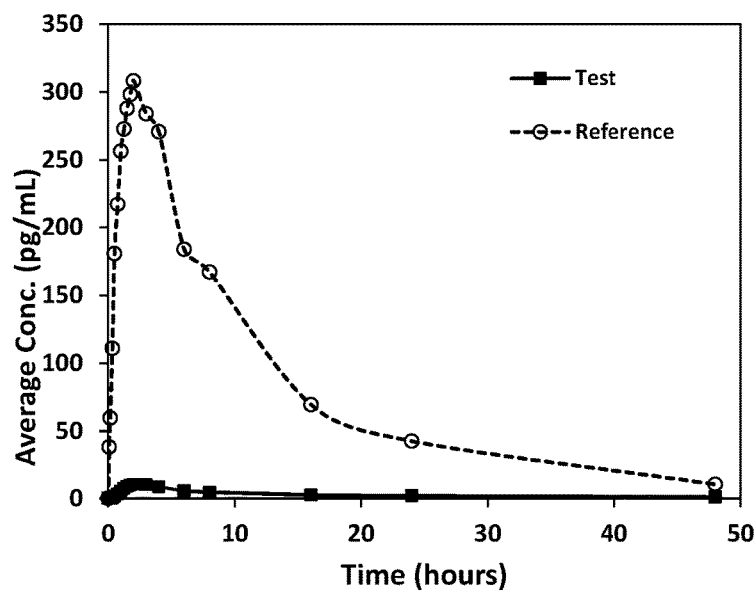
B
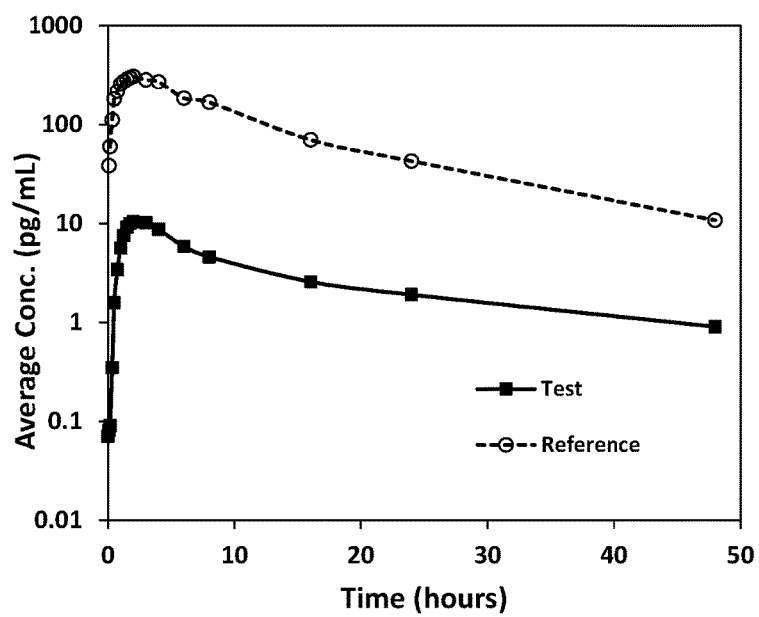

SOFT LOZENGE COMPOSITIONS

CROSS REFERENCE TO RELATED APPLICATIONS

This application is a divisional of U.S. patent application Ser. No. 15/293,535, filed on Oct. 14, 2016, which is a continuation in part of U.S. patent application Ser. No. 15/181,462, filed on Jun. 14, 2016, which claims priority to U.S. Provisional Patent Application No. 62/175,470, filed on Jun. 15, 2015, each of which is incorporated by reference herein in its entirety.

TECHNICAL FIELD

Described herein are oral pharmaceutical compositions suitable for chewing, sucking, buccal dissolution, or swallowing comprising non-systemic corticosteroids soft lozenges, and methods for treating subjects in need thereof with such compositions. In particular, the oral composition provides topical, non-systemic administration and slow-release of one or more active pharmaceutical ingredients to the oral cavity and upper gastrointestinal track, including the esophagus.

BACKGROUND

Steroid therapy has long been the therapy of choice for reducing inflammation by the application of a topical corticosteroid to the affected area, such as in the case of eczema, asthma, or other allergic conditions. In order to reduce systemic toxicity associated with steroid use, topical preparations were developed for inflammation disorders of the esophagus or gastrointestinal tract, such that the steroid could adhere to the esophageal mucosa and provide an anti-inflammatory effect. However, topical corticosteroid therapy is limited. For these types of disorders, treatments have typically involved patients swallowing inhaled corticosteroid medications or corticosteroid suspensions. Treatment using inhaled corticosteroids is achieved via a "puff and swallow" technique, where the patient administers the corticosteroid composition to the mouth, but swallows rather than inhaling. This technique is often difficult for children and geriatric patients, and can result in variable doses and less than an effective dose of the steroid being delivered to the esophagus. In addition, oral administration of topical steroids can also result in oropharyngeal or esophageal candidosis.

Thus, there is an unmet need for oral dosage forms of corticosteroids, where the dosage form can be chewed, sucked, permitted to dissolve in the mouth, or swallowed, and has desirable organoleptic properties; slowly releases the active ingredient in the oral cavity and esophagus; and maintains drug contact with the oral and esophageal tissue for an extended period providing topical, non-systemic delivery.

SUMMARY

Described herein are pharmaceutical compositions containing one or more active ingredients intended to dissolve or disintegrate slowly in the oral cavity. They can be used for topical treatment where the drug is not absorbed through the buccal or esophageal lining. In particular, soft lozenges can be chewed or allowed to dissolve slowly in the mouth. These dosage forms can be flavored and thus are administrable to both pediatric and geriatric patients; they can deliver limited quantities of the active ingredient to the oral cavity and upper gastric system with minimal systemic adsorption; and they allow for the drug to remain in contact with the oral cavity or esophagus for an extended period of time. Soft lozenges or liquid compositions comprising corticosteroids facilitate the topical, non-systemic delivery of corticosteroids for treating esophageal inflammation disorders.

One embodiment described herein is a topical, non-systemic, oral, slow releasing pharmaceutical composition comprising: (a) about 1% to about 5% by mass of one or more release modifiers; (b) about 10% to about 60% by mass of one or more film-forming polymers; (c) about 5% to about 20% by mass of one or more plasticizers; and (d) less than 1% by mass of one or more active pharmaceutical ingredients. In one aspect, the composition, further comprises: (e) about 0.1% to about 5% by mass of one or more pH modifiers; (f) about 10% to about 80% by mass of one or more sweeteners; and (g) about 5% to about 30% by mass of one or more solvents. In another aspect, the composition further comprises: (h) one or more opacifiers, coloring agent, flavoring, thickening agents or combinations thereof; (i) one or more solubilizing agents; and (j) one or more second active pharmaceutical ingredients. In another aspect, the composition comprises a soft lozenge. In another aspect, the composition comprises a liquid. In another aspect, the composition orally dissolves within about 10 to about 15 minutes upon administration to a subject. In another aspect, the composition achieves about 50% dissolution in vitro at pH 7.4 within about 10 to about 30 minutes. In another aspect, the composition topically contacts the oral and esophageal mucosa for at least about 1 minute to about 45 minutes. In another aspect, the composition topically contacts the oral and esophageal mucosa for at least about 1 minute to about 15 minutes. In another aspect, the release modifier comprises one or more of polyethylene oxide, methylcellulose, hydroxypropylmethyl cellulose, hydroxypropyl cellulose, hydroxyethyl cellulose, hydroxymethyl cellulose, polymethylmethacrylate, polyhydroxyethylmethacrylate, polyvinylpyrrolidone, copovidone, polyvinyl alcohol, copolymers of polyvinylpyrrolidone and polyvinyl acetate, or combinations thereof. In another aspect, the release modifier comprises polyethylene oxide. In another aspect, the release modifier comprises polyethylene oxide having a molecular weight ($M_v$) of about 900,000 to about 8,000,000. In another aspect, the release modifier comprises polyethylene oxide having a molecular weight ($M_v$) of about 7,000,000. In another aspect, the film-forming polymer comprises one or more of gelatin, partially hydrolyzed gelatin, hydrolyzed gelatin, hydrolyzed collagen, or combinations thereof. In another aspect, the film-forming polymer comprises one or more gelatins, having a Bloom value of about 50 Bloom to about 150 Bloom. In another aspect, the plasticizer comprises one or more of glycerol, sorbitol, mannitol, maltitol, xylitol, or combinations thereof. In another aspect, the pH modifier comprises one or more of citric acid, acetic acid, lactic acid, malic acid, tartaric acid, fumaric acid, or combinations thereof. In another aspect, the sweetener comprises one or more of xylitol, maltitol, sucralose, mannitol aspartame, *stevia*, or combinations thereof. In another aspect, the solubilizing agent comprises poloxamer, polyoxyethylene 50 stearate, polyoxyl 35 castor oil, polyoxyl 40 hydrogenated castor oil, polyoxyl 10 oleyl ether, polyoxyl 20 cetostearyl ether, polyoxyl 40 stearate, polysorbate 20, polysorbate 40, polysorbate 60, polysorbate 80, propylene glycol diacetate, propylene glycol monostearate, sodium lauryl sulfate, sodium stearate, sorbitan monolaurate, sorbitan monooleate, sorbitan monopalmitate, sorbitan monostearate, or combinations thereof. In another aspect, the thickening agent comprises polyacrylic acid, methylcellulose, alginic acid, chitosan, carboxymethyl cellulose, sodium carboxymethyl cellulose, locust bean gum, xanthum gum, high swelling crosslinked polymers, or combinations thereof. In another aspect, the active pharmaceutical ingredient comprises one or more corticosteroids. In another aspect, the active pharmaceutical ingredient comprises one or more of alclometasone, amcinonide, beclomethasone, betamethasone, budesonide, ciclesonide, clobetasol, clobetasone, clocortolone, cloprednol, cortivazol, deflazacort, deoxycorticosterone, desonide desoximetasone, dexamethasone, diflorasone, diflucortolone, difluprednate, flucorolone, fludrocortisone, fludroxycortide, flumetasone, flunisolide, fluocinolone acetonide, fluocinonide, fluocortin, fluocortolone, fluorometholone, fluperolone, fluticasone, fluticasone propionate, fluprednidene, formocortal, halcinonide, halometasone, hydrocortisone aceponate, hydrocortisone buteprate, hydrocortisone butyrate, loteprednol, medrysone, meprednisone, methylprednisolone, methylprednisolone aceponate, mometasone furoate, paramethasone, prednicarbate, prednisone, prednisolone, prednylidene, rimexolone, tixocortol, triamcinolone, ulobetasol, combinations thereof, pharmaceutically acceptable salts thereof, or esters thereof. In another aspect, the active pharmaceutical ingredients comprise one or more of fluticasone, budesonide, salts thereof, or combinations thereof. In another aspect, the active pharmaceutical ingredient comprises fluticasone or a salt thereof. In another aspect, the active pharmaceutical ingredient comprises fluticasone propionate. In another aspect, the composition comprises about 0.025% or about 0.05% fluticasone propionate. In another aspect, the composition comprises about 0.5 mg or about 1.0 mg of fluticasone propionate. In another aspect, the second active pharmaceutical ingredient comprises lidocaine, prilocaine, or a combination thereof. In another aspect, the composition topically contacts the oral and esophageal mucosa for about 1 minute to about 10 minutes.

Another embodiment described herein is topical, non-systemic oral pharmaceutical composition comprising: (a) about 10% to about 60% by mass of one or more film-forming polymers; (b) about 5% to about 20% by mass of one or more plasticizers; (c) about 0.1% to about 5% by mass of one or more pH modifiers; (d) about 10% to about 80% by mass of one or more sweeteners; (e) about 5% to about 30% by mass of one or more solvents; and (g) about 1% to about 5% by mass of one or more release modifiers; (h) about 0.1% to about 5% by mass of one or more solubilizing agents; and (i) about 0.001% to about 1% by mass of fluticasone propionate. In one aspect, the composition further comprises (j) about 0.1% to about 50% by mass of one or more thickening agents. In another aspect, the composition further comprises a second active pharmaceutical ingredient. In another aspect, the second active pharmaceutical ingredient comprises about 0.5% to about 5% by weight of lidocaine, prilocaine, or a combination thereof, and the weight percentage of maltitol is reduced accordingly. In another aspect, the composition comprises a liquid or solid dosage form. In another aspect, the liquid dosage form comprises a solution, syrup, suspension, elixir, or concentrate. In another aspect, the solid dosage form comprises a soft lozenge. In another aspect, the composition orally dissolves within about 10 to about 15 minutes upon administration to a subject. In another aspect, the composition achieves 50% dissolution in vitro at pH 7.4 within about 10 to about 30 minutes. In another aspect, the composition topically contacts the oral and esophageal mucosa for at least about 1 minute to about 45 minutes. In another aspect, the composition provides one or more of the following pharmacokinetic parameters upon administration to a subject: (a) a mean plasma fluticasone propionate $T_{max}$ of about 1.75 hours to about 3 hours; (b) a mean plasma fluticasone propionate $C_{max}$ of about 8 pg/mL to about 11 pg/mL; (c) a mean plasma fluticasone propionate $AUC_{0\to\tau}$ of about 105 pg·h/mL to about 130 pg·h/mL; (d) a mean plasma fluticasone propionate $AUC_{0\to\infty}$ of about 150 pg·h/mL to about 160 pg·h/mL; (e) a mean fluticasone propionate half-life ($t_{1/2}$) of about 0.01 h to about 0.1 h; or (f) a mean fluticasone terminal elimination rate constant ($\lambda$) of about 10 h$^{-1}$ to about 20 h$^{-1}$. In another aspect, the composition is useful for treating a subject suffering from one or more of oral or esophageal inflammation, eosinophilic esophagitis, inflammatory bowel disease involving the esophagus, oral lichen planus, aphthous stomatitis, Crohn's disease, esophageal inflammation secondary to caustic/irritant ingestion, recurrent esophageal strictures of any cause and including irritant ingestion, pill-induced esophagitis, systemic diseases, congential diseases, epidermolysis bullosa, trauma, or post-surgery inflammation.

Another embodiment described herein is a method for treating, retarding the progression of, prophylaxis of, delaying the onset of, ameliorating, or reducing the symptoms of one or more of esophageal, oral, or buccal inflammation, eosinophilic esophagitis, oral lichen planus, aphthous stomatitis, odynophagia, acid reflux, dysphagia, oral, esophageal or peptic ulcers, heart burn, chest pain, abdominal pain, nausea, vomiting, coughing, sore throat, decrease in appetite, or failure to thrive, comprising administering to a subject in need thereof any of the pharmaceutical compositions described herein.

Another embodiment described herein is a pharmaceutical composition useful for retarding the progression of, prophylaxis of, delaying the onset of, ameliorating, or reducing the symptoms of one or more of esophageal, oral, or buccal inflammation, eosinophilic esophagitis, oral lichen planus, aphthous stomatitis, odynophagia, acid reflux, dysphagia, oral, esophageal or peptic ulcers, heart burn, chest pain, abdominal pain, nausea, vomiting, coughing, sore throat, decrease in appetite, or failure to thrive, comprising administering to a subject in need thereof any of the pharmaceutical compositions described herein.

Another embodiment described herein is a method for treating for treating, retarding the progression of, prophylaxis of, delaying the onset of, ameliorating, or reducing the symptoms of one or more of esophageal oral, or buccal inflammation, eosinophilic esophagitis, inflammatory bowel disease involving the esophagus, oral lichen planus, aphthous stomatitis, Crohn's disease, esophageal inflammation secondary to caustic/irritant ingestion, recurrent esophageal strictures of any cause and including irritant ingestion, pill-induced esophagitis, systemic diseases, congenital diseases, epidermolysis bullosa, trauma, or post-surgery inflammation comprising administering to a subject in need thereof any of the pharmaceutical compositions described herein. In one aspect, the composition provides one or more of the following pharmacokinetic parameters: (a) a mean plasma fluticasone propionate $T_{max}$ of about 1.75 hours to about 3 hours; (b) a mean plasma fluticasone propionate $C_{max}$ of about 8 pg/mL to about 11 pg/mL; (c) a mean plasma fluticasone propionate $AUC_{0\to\tau}$ of about 105 pg·h/mL to about 130 pg·h/mL; (d) a mean plasma fluticasone propionate $AUC_{0\to\infty}$ of about 150 pg·h/mL to about 160 pg·h/mL; (e) a mean fluticasone propionate half-life ($t_{1/2}$) of about 0.01 h to about 0.1 h; or (f) a mean fluticasone terminal elimination rate constant (λ) of about 10 h$^{-1}$ to about 20 h$^{-1}$.

Another embodiment described herein is a pharmaceutical combination comprising the one of the compositions described herein comprising a corticosteroid and one or more additional therapeutic compounds. In one aspect, the one or more additional therapeutic compound comprises one or more of antacids (e.g., calcium hydroxide, magnesium hydroxide, alluminum hydroxide, sodium bicarbonate, calcium carbonate, bismuth subsalicylate, or others; Maalox, Mylanta, Gaviscon, Kaopectate, Pepto-Bismol) sucralfate, esomeprazole, omeprazole, lansoprazole, dexlansoprazole, esomeprazole, pantoprazole, rabeprazole, ilaprazole, cimetidine, ranitidine, famotidine, lafutidine, nizatidine, roxatidine, tiotidine, salmeterol, albuterol, aclidinium, ipratropium, tiotropium, umeclidinium, acrivastine, azelastine, bilastine, brompheniramine, buclizine, bromodiphenhydramine, carbinoxamine, chlorpromazine, cyclizine, chlorphenamine, chlorodiphenhydramine, clemastine, cyproheptadine, dexbrompheniramine, dexchlorpheniramine, dimenhydrinate, dimetindene, diphenhydramine, doxylamine, ebastine, embramine, fexofenadine, hydroxyzine, loratadine, meclozine, mirtazapine, olopatadine, orphenadrine, phenindamine pheniramine, phenyltoloxamine, promethazine, quetiapine, rupatadine, tripelennamine, triprolidine, clobenpropit, ciproxifan, conessine, thioperamide, montelukast, zafirlukast, pranlukast, mepolizumab, reslizumab, omalizumab, infliximab, azathioprine, 6-mercaptopurine, thioguanine, aspirin (acetylsalicylic acid), ibuprofen, naproxen, ketoprofen, celecoxib, diclofenac, amikacin, gentamicin, kanamycin, neomycin, netilmicin, tobramycin, paromomycin, streptomycin, spectinomycin, geldanamycin, herbimycin, rifaximin, loracarbef, ertapenem, doripenem, imipenem/cilastatin, meropenem, cefadroxil, cefazolin, cefalotin, cefalexin, cefaclor, cefamandole, cefoxitin, cefprozil, cefuroxime, cefixime, cefdinir, cefditoren, cefoperazone, cefotaxime, cefpodoxime, ceftazidime, ceftibuten, ceftizoxime, ceftriaxone, cefepime, ceftaroline fosamil, ceftobiprole, teicoplanin, vancomycin, telavancin, dalbavancin, oritavancin, clindamycin, lincomycin, daptomycin, azithromycin, clarithromycin, dirithromycin, erythromycin, roxithromycin, troleandomycin, telithromycin, spiramycin, aztreonam, furazolidone, nitrofurantoin, linezolid, posizolid, radezolid, torezolid, amoxicillin, ampicillin, azlocillin, carbenicillin, cloxacillin, dicloxacillin, flucloxacillin, mezlocillin, methicillin, nafcillin, oxacillin, penicillin G, penicillin V, piperacillin, temocillin, ticarcillin, amoxicillin/clavulanate, ampicillin/sulbactam, piperacillin/tazobactam, ticarcillin/clavulanate, bacitracin, colistin, polymyxin B, ciprofloxacin, enoxacin, gatifloxacin, gemifloxacin, levofloxacin, lomefloxacin, moxifloxacin, nalidixic acid, norfloxacin, ofloxacin, trovafloxacin, grepafloxacin, sparfloxacin, temafloxacin, mafenide, sulfacetamide, sulfadiazine, silver sulfadiazine, sulfadimethoxine, sulfamethizole, sulfamethoxazole, solfanilamide, sulfasalazine, sulfisoxazole, trimethoprim-sulfamethoxazole, sulfamidochrysoidine, demeclocycline, doxycycline, minocycline, oxytetracycline, tetracycline, clofazimine, dapsone, capreomycin, cycloserine, ethambutol, ethionamide, isoniazid, pyrazinamide, rifampicin, rifabutin, rifapentine, streptomycin, arsphenamine, chloramphenicol, fosfomycin, fusidic acid, metronidazole, mupirocin, platensimycin, quinupristin/dalfopristin, thiamphenicol, tigecycline, tinidazole, trimethoprim, or combinations thereof.

One embodiment described herein comprises a topical, non-systemic oral soft lozenge pharmaceutical composition comprising a shell encapsulating a semi solid matrix fill, the shell comprising: (a) one or more first film-forming polymers; (b) one or more first plasticizers; (c) one or more first pH modifiers; (d) one or more first sweeteners; and (e) one or more first solvents; and the matrix fill comprising: (f) one or more second film-forming polymers; (g) one or more release modifiers; (h) one or more second plasticizers; (i) one or more second pH modifiers; (j) one or more second sweeteners; (k) one or more second solvents; and (l) one or more active pharmaceutical ingredients. In one aspect, the shell further comprises: (m) one or more opacifiers, coloring agents, flavorings, or combinations thereof; and the matrix comprises: (n) one or more solubilizing agents; and (o) one or more second active pharmaceutical ingredients. In another aspect, the shell or matrix further comprises one or more pharmaceutically acceptable excipients. In another aspect, the film-forming polymer comprises one or more of gelatin, partially hydrolyzed gelatin, hydrolyzed gelatin, hydrolyzed collagen, or combinations thereof. In another aspect, the film-forming polymer comprises one or more gelatins, having a Bloom value of about 50 Bloom to about 150 Bloom. In another aspect, the plasticizer comprises one or more of glycerol, sorbitol, mannitol, maltitol, xylitol, or combinations thereof. In another aspect, the pH modifier comprises one or more of citric acid, acetic acid, lactic acid, malic acid, tartaric acid, fumaric acid, or combinations thereof. In another aspect, the release modifier comprises one or more of polyethylene oxide, methylcellulose, hydroxypropylmethyl cellulose, hydroxypropyl cellulose, hydroxyethyl cellulose, hydroxymethyl cellulose, polymethylmethacrylate, polyhydroxyethylmethacrylate, polyvinylpyrrolidone, copovidone, polyvinyl alcohol, copolymers of polyvinylpyrrolidone and polyvinyl acetate, or combinations thereof. In another aspect, the release modifier comprises polyethylene oxide. In another aspect, the release modifier comprises polyethylene oxide having a molecular weight ($M_v$) of about 900,000 to about 8,000,000. In another aspect, the release modifier comprises polyethylene oxide having a molecular weight ($M_v$) of about 7,000,000. In another aspect, the sweetener comprises one or more of xylitol, maltitol, sucralose, mannitol aspartame, *stevia*, or combinations thereof. In another aspect, the solubilizing agent comprises poloxamer, polyoxyethylene 50 stearate, polyoxyl 35 castor oil, polyoxyl 40 hydrogenated castor oil, polyoxyl 10 oleyl ether, polyoxyl 20 cetostearyl ether, polyoxyl 40 stearate, polysorbate 20, polysorbate 40, polysorbate 60, polysorbate 80, propylene glycol diacetate, propylene glycol monostearate, sodium lauryl sulfate, sodium stearate, sorbitan monolaurate, sorbitan monooleate, sorbitan monopalmitate, sorbitan monostearate, or combinations thereof. In another aspect, the active pharmaceutical ingredient comprises one or more corticosteroids or glucocorticosteroids. The composition of claim 1, wherein the active pharmaceutical ingredient comprises one or more of alclometasone, amcinonide, beclometasone, betamethasone, budesonide, ciclesonide, clobetasol, clobetasone, clocortolone, cloprednol, cortivazol, deflazacort, deoxycorticosterone, desonide desoximetasone, dexamethasone, diflorasone, diflucortolone, difluprednate, fluclorolone, fludrocortisone, fludroxycortide, flumetasone, flunisolide, fluocinolone acetonide, fluocinonide, fluocortin, fluocortolone, fluorometholone, fluperolone, fluticasone, fluticasone propionate, fluprednidene, formocortal, halcinonide, halometasone, hydrocortisone aceponate, hydrocortisone buteprate, hydrocortisone butyrate, loteprednol, medrysone, meprednisone, methylprednisolone, methylprednisolone aceponate, mometasone furoate, parametasone, prednicarbate, prednisone, prednisolone, prednylidene, rimexolone, tixocortol, triamcinolone, ulobetasol, combinations thereof, pharmaceutically acceptable salts thereof, or esters thereof. In another aspect, the active pharmaceutical ingredients comprise one or more of fluticasone, budesonide, salts thereof, or combinations thereof. In another aspect, the active pharmaceutical ingredient comprises fluticasone or a salt thereof. In another aspect, the active pharmaceutical ingredient comprises fluticasone propionate. In another aspect, the matrix comprises about 0.025% or about 0.05% fluticasone. In another aspect, the matrix comprises about 0.5 mg or about 1.0 mg of fluticasone. In another aspect, the second active pharmaceutical ingredient comprises lidocaine, prilocaine, or a combination thereof.

Another embodiment described herein comprises a pharmaceutical composition comprising a shell encapsulating a semi solid matrix fill, wherein the shell comprises: (a) about 10% to about 60% of one or more first film-forming polymers; (b) about 5% to about 20% of one or more first plasticizers; (c) about 0.1% to about 5% of one or more first pH modifiers; (d) about 10% to about 80% of one or more first sweeteners; and (e) about 5% to about 30% of one or more first solvents; and the matrix comprises: (f) about 5% to about 30% of one or more second film-forming polymers; (g) about 1% to about 5% of one or more release modifiers; (h) about 5% to about 20% of one or more second plasticizers; (i) about 0.5% to about 5% of one or more second pH modifiers; (j) about 10% to about 80% of one or more second sweeteners; (k) about 0.1% to about 5% of one or more solubilizing agents; (l) about 5% to about 30% of one or more second solvents; and (m) about 0.001% to about 1% of one or more active pharmaceutical ingredients.

Another embodiment described herein comprises a pharmaceutical composition comprising a shell encapsulating a semi solid matrix fill, wherein the shell comprises: (a) about 34% of one or more first film-forming polymers; (b) about 23% of one or more first plasticizers; (c) about 0.5% of one or more first pH modifiers; (d) about 17% of one or more first sweeteners; and (e) about 25% of one or more first solvents; and the matrix comprises: (f) about 7.5% of one or more second film-forming polymers; (g) about 3.0% of one or more release modifiers; (h) about 7.5% of one or more second plasticizers; (i) about 1% of one or more second pH modifiers; (j) about 62% of one or more second sweeteners; (k) about 0.7% of one or more solubilizing agents; (l) about 18% of one or more second solvents; and (m) about 0.025% or about 0.05% of one or more active pharmaceutical ingredients.

Another embodiment described herein comprises a pharmaceutical composition comprising (a) about 15% to about 20% of one or more film-forming polymers; (b) about 0.5% to about 3% of one or more release modifiers; (c) about 10% to about 15% of one or more plasticizers; (d) about 0.5% to about 1.5% of one or more pH modifiers; (e) about 40% to about 55% of one or more sweeteners; (f) about 0.1% to about 1% of one or more solubilizing agents; (g) about 15% to about 25% of one or more solvents; (h) about 0.01% or about 0.1% of one or more active pharmaceutical ingredients; and (i) optionally, about 0.1% to about 1% of one or more excipients comprising opacifiers, colorings, or flavorings.

Another embodiment described herein comprises a pharmaceutical composition comprising (a) about 17% of one or more film-forming polymers; (b) about 2% of one or more release modifiers; (c) about 13% of one or more plasticizers; (d) about 0.8% of one or more pH modifiers; (e) about 46% of one or more sweeteners; (f) about 0.4% of one or more solubilizing agents; (g) about 20% of one or more solvents; (h) about 0.016% or about 0.032% of one or more active pharmaceutical ingredients; and (i) optionally, about 0.5% of one or more excipients comprising opacifiers, colorings, or flavorings.

Another embodiment described herein comprises a pharmaceutical composition comprising a shell encapsulating a semi solid matrix fill, wherein the shell comprises: (a) about 5% to about 30% of 150 Bloom gelatin; (b) about 5% to about 20% of 100 Bloom gelatin; (c) about 1% to about 10% of gelatin hydrolysate; (d) about 5% to about 30% of glycerol; (e) about 0.1% to about 5% of citric acid; (f) about 5% to about 30% of maltitol; (g) about 1% to about 10% of xylitol; (h) about 0.1% to about 2% of sucralose; and (i) about 5% to about 30% of water; and the matrix comprises: (j) about 5% to about 20% of 150 Bloom gelatin; (k) about 1% to about 5% of polyethylene oxide; (l) about 5% to about 10% of glycerol; (m) about 0.5% to about 5% of citric acid; (n) about 30% to about 65% of maltitol; (o) about 1% to about 10% of xylitol; (p) about 0.1% to about 2% of sucralose; (q) about 0.1% to about 1% of polysorbate 80; (r) about 10% to about 30% of water; and (s) about 0.001% to about 1% of fluticasone propionate.

Another embodiment described herein comprises a pharmaceutical composition comprising a shell encapsulating a semi solid matrix fill, the shell comprises: (a) about 19% 150 Bloom gelatin; (b) about 13% 100 Bloom gelatin; (c) about 2.5% gelatin hydrolysate; (d) about 23% glycerol; (e) about 0.5% citric acid; (f) about 14% maltitol; (g) about 2.5% xylitol; (h) about 0.2% sucralose; and (i) about 25% water; and the matrix comprises: (j) about 7.5% 150 Bloom gelatin; (k) about 3% polyethylene oxide; (l) about 5% to about 10% of glycerol; (m) about 1% citric acid; (n) about 58% maltitol; (o) about 4% of xylitol; (p) about 0.3% sucralose; (q) about 0.7% polysorbate 80; (r) about 18% water; and (s) about 0.025% or about 0.05% fluticasone propionate.

Another embodiment described herein comprises a pharmaceutical composition comprising (a) about 5% to about 30% of 150 Bloom gelatin; (b) about 5% to about 20% of 100 Bloom gelatin; (c) about 1% to about 10% of gelatin hydrolysate; (d) about 1% to about 5% of polyethylene oxide; (e) about 1% to about 20% of glycerol; (f) about 0.1% to about 5% of citric acid; (g) about 20% to about 60% of maltitol; (h) about 0.5% to about 5% of xylitol; (i) about 0.1% to about 2% of sucralose; (j) about 0.1% to about 1% of polysorbate 80; (k) about 5% to about 30% of water; (l) about 0.01% or about 0.1% of one or more active pharmaceutical ingredients; and (m) optionally, about 0.1% to about 1% of one or more excipients comprising opacifiers, colorings, or flavorings.

Another embodiment described herein comprises a pharmaceutical composition comprising (a) about 12% 150 Bloom gelatin; (b) about 5% 100 Bloom gelatin; (c) about 1% gelatin hydrolysate; (d) about 2% polyethylene oxide; (e) about 13% glycerol; (f) about 0.8% citric acid; (g) about 42% maltitol; (h) about 4% xylitol; (i) about 0.3% sucralose; (j) about 0.4% polysorbate 80; (k) about 20% water; and (l) about 0.025% or about 0.05% fluticasone propionate.

Another embodiment described herein comprises a pharmaceutical composition comprising a second active ingredient, wherein the second active pharmaceutical ingredient comprises about 0.5% to about 5% by weight of lidocaine, prilocaine, or a combination thereof, and the weight percentage of maltitol is reduced accordingly.

Another embodiment described herein comprises a pharmaceutical composition comprising any of the compositions described herein for treating, retarding the progression of, prophylaxis of, delaying the onset of, ameliorating, or reducing the symptoms of one or more of esophageal, oral, or buccal inflammation, eosinophilic esophagitis, oral lichen planus, aphthous stomatitis, odynophagia, acid reflux, dysphagia, oral, esophageal or peptic ulcers, heart burn, chest pain, abdominal pain, nausea, vomiting, coughing, sore throat, decrease in appetite, or failure to thrive.

Another embodiment described herein comprises a pharmaceutical composition comprising any of the compositions described herein for treating a subject suffering from one or more of oral or esophageal inflammation, eosinophilic esophagitis, inflammatory bowel disease involving the esophagus, oral lichen planus, aphthous stomatitis, Crohn's disease, esophageal inflammation secondary to caustic/irritant ingestion, recurrent esophageal strictures of any cause and including irritant ingestion, pill-induced esophagitis, systemic diseases, congenital diseases, epidermolysis bullosa, trauma, or post-surgery inflammation.

Another embodiment described herein comprises a method for treating, retarding the progression of, prophylaxis of, delaying the onset of, ameliorating, or reducing the symptoms of one or more of esophageal, oral, or buccal inflammation, eosinophilic esophagitis, oral lichen planus, aphthous stomatitis, odynophagia, acid reflux, dysphagia, oral, esophageal or peptic ulcers, heart burn, chest pain, abdominal pain, nausea, vomiting, coughing, sore throat, decrease in appetite, or failure to thrive, comprising administering to a subject in need thereof any of the pharmaceutical compositions described herein.

Another embodiment described herein comprises a method for treating a subject suffering from one or more of esophageal oral, or buccal inflammation, eosinophilic esophagitis, inflammatory bowel disease involving the esophagus, oral lichen planus, aphthous stomatitis, Crohn's disease, esophageal inflammation secondary to caustic/irritant ingestion, recurrent esophageal strictures of any cause and including irritant ingestion, pill-induced esophagitis, systemic diseases, congenital diseases, epidermolysis bullosa, trauma, or post-surgery inflammation comprising administering to the subject in need thereof any of the pharmaceutical compositions described herein.

Another embodiment described herein comprises a means for treating a subject suffering from one or more of esophageal oral, or buccal inflammation, eosinophilic esophagitis, inflammatory bowel disease involving the esophagus, oral lichen planus, aphthous stomatitis, Crohn's disease, esophageal inflammation secondary to caustic/irritant ingestion, recurrent esophageal strictures of any cause and including irritant ingestion, pill-induced esophagitis, systemic diseases, congenital diseases, epidermolysis bullosa, trauma, or post-surgery inflammation comprising administering to the subject in need thereof an oral topical non-systemic pharmaceutical composition comprising any of the pharmaceutical compositions described herein.

A method for manufacturing an oral topical non-systemic pharmaceutical dosage form suitable for chewing, sucking, or buccal dissolution comprising: (a) combining gelatin, glycerol, water, maltitol, xylitol, sucralose, citric acid, polysorbate 80 and one or more active pharmaceutical ingredient to produce a matrix fill solution; (b) combining one or more gelatins, glycerol, water, maltitol, xylitol, sucralose, and citric acid to produce a shell gel mass; (c) casting the shell gel mass into films using heat-controlled drums or surfaces; and (d) injecting the matrix fill solution between the shell ribbons, and forming a soft lozenge using rotary die encapsulation technology.

Another embodiment described herein comprises a soft lozenge produced by the methods described herein. In one aspect, the soft lozenge comprises any of the composition described herein.

Another embodiment described herein comprises a kit for dispensing any of the oral pharmaceutical compositions described herein, comprising: (a) at least one oral pharmaceutical composition suitable for chewing, sucking, or buccal dissolution comprising one or more corticosteroids; (b) at least one receptacle comprising a tamper evident, moisture proof packaging that reduces the ability of removing the oral, enteric pharmaceutical composition comprising blister or strip packs, aluminum blister, transparent or opaque polymer blister with pouch, polypropylene tubes, colored blister materials, tubes, bottles, and bottles optionally containing a child-resistant feature, optionally comprising a desiccant, such as a molecular sieve or silica gel; and (c) optionally, an insert comprising instructions or prescribing information for the oral pharmaceutical composition. In one aspect, the oral pharmaceutical composition comprises any of the compositions described herein.

Another embodiment described herein comprises a pharmaceutical combination comprising a pharmaceutical composition described herein and one or more additional therapeutic compounds. In one aspect, the one or more additional therapeutic compound comprises one or more of antacids (e.g., calcium hydroxide, magnesium hydroxide, alluminum hydroxide, sodium bicarbonate, calcium carbonate, bismuth subsalicylate, or others; Maalox, Mylanta, Gaviscon, Kaopectate, Pepto-Bismol) sucralfate, esomeprazole, omeprazole, lansoprazole, dexlansoprazole, esomeprazole, pantoprazole, rabeprazole, ilaprazole, cimetidine, ranitidine, famotidine, lafutidine, nizatidine, roxatidine, tiotidine, salmeterol, albuterol, aclidinium, ipratropium, tiotropium, umeclidinium, acrivastine, azelastine, bilastine, brompheniramine, buclizine, bromodiphenhydramine, carbinoxamine, chlorpromazine, cyclizine, chlorphenamine, chlorodiphenhydramine, clemastine, cyproheptadine, dexbrompheniramine, dexchlorpheniramine, dimenhydrinate, dimetindene, diphenhydramine, doxylamine, ebastine, embramine, fexofenadine, hydroxyzine, loratadine, meclozine, mirtazapine, olopatadine, orphenadrine, phenindamine pheniramine, phenyltoloxamine, promethazine, quetiapine, rupatadine, tripelennamine, triprolidine, clobenpropit, ciproxifan, conessine, thioperamide, montelukast, zafirlukast, pranlukast, mepolizumab, reslizumab, omalizumab, infliximab, azathioprine, 6-mercaptopurine, thioguanine, aspirin (acetylsalicylic acid), ibuprofen, naproxen, ketoprofen, celecoxib, diclofenac, amikacin, gentamicin, kanamycin, neomycin, netilmicin, tobramycin, paromomycin, streptomycin, spectinomycin, geldanamycin, herbimycin, rifaximin, loracarbef, ertapenem, doripenem, imipenem/cilastatin, meropenem, cefadroxil, cefazolin, cefalotin, cefalexin, cefaclor, cefamandole, cefoxitin, cefprozil, cefuroxime, cefixime, cefdinir, cefditoren, cefoperazone, cefotaxime, cefpodoxime, ceftazidime, ceftibuten, ceftizoxime, ceftriaxone, cefepime, ceftaroline fosamil, ceftobiprole, teicoplanin, vancomycin, telavancin, dalbavancin, oritavancin, clindamycin, lincomycin, daptomycin, azithromycin, clarithromycin, dirithromycin, erythromycin, roxithromycin, troleandomycin, telithromycin, spiramycin, aztreonam, furazolidone, nitrofurantoin, linezolid, posizolid, radezolid, torezolid, amoxicillin, ampicillin, azlocillin, carbenicillin, cloxacillin, dicloxacillin, flucloxacillin, mezlocillin, methicillin, nafcillin, oxacillin, penicillin G, penicillin V, piperacillin, temocillin, ticarcillin, amoxicillin/clavulanate, ampicillin/sulbactam, piperacillin/tazobactam, ticarcillin/ clavulanate, bacitracin, colistin, polymyxin B, ciprofloxacin, enoxacin, gatifloxacin, gemifloxacin, levofloxacin, lomefloxacin, moxifloxacin, nalidixic acid, norfloxacin, ofloxacin, trovafloxacin, grepafloxacin, sparfloxacin, temafloxacin, mafenide, sulfacetamide, sulfadiazine, silver sulfadiazine, sulfadimethoxine, sulfamethizole, sulfamethoxazole, solfanilamide, sulfasalazine, sulfisoxazole, trimethoprim-sulfamethoxazole, sulfamidochrysoidine, demeclocycline, doxycycline, minocycline, oxytetracycline, tetracycline, clofazimine, dapsone, capreomycin, cycloserine, ethambutol, ethionamide, isoniazid, pyrazinamide, rifampicin, rifabutin, rifapentine, streptomycin, arsphenamine, chloramphenicol, fosfomycin, fusidic acid, metronidazole, mupirocin, platensimycin, quinupristin/dalfopristin, thiamphenicol, tigecycline, tinidazole, trimethoprim, or combinations thereof.

Another embodiment described herein comprises a method for treating, retarding the progression of, prophylaxis of, delaying the onset of, ameliorating, or reducing the symptoms of one or more of esophageal oral, or buccal inflammation, eosinophilic esophagitis, inflammatory bowel disease involving the esophagus, oral lichen planus, aphthous stomatitis, Crohn's disease, esophageal inflammation secondary to caustic/irritant ingestion, recurrent esophageal strictures of any cause and including irritant ingestion, pill-induced esophagitis, systemic diseases, congenital diseases, epidermolysis bullosa, trauma, or post-surgery inflammation comprising administering to a subject in need thereof any of the pharmaceutical combinations described herein.

BRIEF DESCRIPTION OF THE DRAWINGS

FIG. 1. (A) Linear scale plot of the mean plasma concentration over time for the Test fluticasone propionate lozenge and the Reference fluticasone propionate aerosol. (B) Log scale plot of the same data shown in (A).

DETAILED DESCRIPTION

Described herein are topical, non-systemic, slow-release oral pharmaceutical compositions comprising chewable, suckable, dissolvable soft lozenges or swallowable liquid formulations comprising one or more active pharmaceutical ingredients.

The oral pharmaceutical compositions described herein suitable for chewing, sucking, buccal dissolution, or swallowing comprising one or more corticosteroids as at least one of the active pharmaceutical ingredients, and methods for preparation thereof. The oral composition provides topical, non-systemic administration and slow release of one or more active pharmaceutical ingredients to the oral cavity and upper gastrointestinal track, including the esophagus. The soft lozenge comprises a firm, gelatinous solid or semi-solid matrix fill encapsulated by a gelatin capsule shell. Liquid formulations comprise solutions, syrups, suspensions, elixirs, or concentrates. The phrase "organoleptic properties" as used herein refers to the sensory aspects experienced by one or more subjects, including but not limited to, sight, smell, taste, mouth feel, moisture content/ dryness, plasticity, chewability, dissolution, residue, and aftertaste.

The phrase "suitable for chewing, sucking, or buccal dissolution" as used herein refers to the propensity of the soft lozenges described herein to dissolve in a subject's mouth by passive incubation in the oral cavity, or actively by sucking, chewing, or mastication to deliver one or more active pharmaceutical ingredients to the oral cavity and esophagus. In one aspect, the soft lozenge can dissolve passively over time in the subject's saliva. In another aspect, the soft lozenge can be sucked by the subject. In another aspect, the soft lozenge can be chewed by the subject. In another aspect, the soft lozenge may be ingested by a combination of dissolving, sucking, or chewing by the subject. Regardless of the mode of oral dissolution, the soft lozenge provides topical delivery of one or more active pharmaceutical ingredients to the oral cavity and esophagus.

The terms "active ingredient" or "active pharmaceutical ingredient" as used herein refer to a pharmaceutical agent, active ingredient, compound, or substance, compositions, or mixtures thereof, that provide a pharmacological, often beneficial, effect. In one embodiment, the active pharmaceutical ingredient is one or more corticosteroids.

The term "topical" as used herein refers to the administration of an active pharmaceutical ingredient directly to a portion of a subject's body, particularly to the mucus membranes. In one embodiment describe herein, topical refers to the administration of one or more corticosteroids or other active pharmaceutical ingredients to the inner lumen of the oral cavity and esophagus.

The term "contact" as used herein refers to the presence of the dissolved dosage form directly on the mucous membranes or tissues of the oral cavity or esophagus.

The term "non-systemic" as used herein refers to the administration of an active pharmaceutical ingredient that is not sufficiently absorbed to a significant extent so that it is transported throughout the body via the circulatory system or detectable in blood or plasma. In one embodiment described herein, an active pharmaceutical ingredient is topically administered at a dosage insufficient to become systemically circulated.

The term "delayed release" as used herein refers to the release of the active ingredient over a period of time that is subsequent to the dissolution of the dosage form.

The term "dissolution" as used herein refers to the complete disintegration of the dosage form either intra-orally or in-vitro.

The terms "dosage" or "dose" as used herein denote any forms of the active ingredient formulation that contain an amount sufficient to produce a therapeutic effect with a single administration. The dosage form described herein is for oral administration. The oral dosage form may also be a liquid comprising a suspension, syrup, elixir or concentrate, wherein the corticosteroid may be formulated as a viscous liquid suspension having enough viscosity such that upon drinking, the suspension adheres to the esophageal surface. The oral dosage form may also be a soft lozenge.

The terms "active pharmaceutical ingredient load" or "drug load" as used herein refer to the quantity (mass) of the active pharmaceutical ingredient comprised in a single liquid dosage or soft lozenge.

The term "formulation" or "composition" as used herein refers to the drug in combination with pharmaceutically acceptable excipients. This term includes orally administrable formulations as well as formulations administrable by other means.

As used herein, the term "pharmaceutical composition" refers to a composition comprising at least on active ingredient, nutraceutical, nutritional, or vitamin.

The term "release modifier" as used herein refers to a substance that slows the dissolution and release of the active ingredient from the soft lozenge.

The term "pH modifier" as used herein refers to a substance that adjusts the pH of a composition. In one embodiment described herein, pH modifiers comprise one or more organic acids.

The term "absolute bioavailability" as used herein refers to the fraction of a drug or active pharmaceutical ingredient absorbed through non-intravenous administration (e.g., oral administration) as compared to intravenous administration of the same drug or active pharmaceutical ingredient.

The term "$C_{max}$" as used herein refers to the maximum observed blood (plasma, serum, or whole blood) concentration or the maximum blood concentration calculated or estimated from a concentration to time curve, and is expressed in units of mg/L or ng/mL, as applicable.

The term "$C_{min}$" as used herein refers to the minimum observed blood (plasma, serum, or whole blood) concentration or the minimum blood concentration calculated or estimated from a concentration to time curve, and is expressed in units of mg/L or ng/mL, as applicable.

The term "$C_{avg}$" as used herein refers to the blood (plasma, serum, or whole blood) concentration of the drug within the dosing interval, is calculated as AUC/dosing interval, and is expressed in units of mg/L or ng/mL, as applicable.

The term "$T_{max}$" as used herein refers to the time after administration at which $C_{max}$ occurs, and is expressed in units of hours (h) or minutes (min), as applicable.

The term "$_{0\rightarrow\tau}$" as used herein refers to the area under the blood (plasma, serum, or whole blood) concentration versus time curve from time zero to time tau ($\tau$) over a dosing interval at steady state, where tau is the length of the dosing interval, and is expressed in units of h·mg/L or h·ng/mL, as applicable. For example, the term $AUC_{0\rightarrow 12}$ as used herein refers to the area under the concentration versus time curve from 0 to 12 hours.

The term "$_{0\rightarrow\infty}$" as used herein refers to the area under the blood (plasma, serum, or whole blood) concentration versus time curve from time 0 hours to infinity, and is expressed in units of h·mg/L or h·ng/mL, as applicable.

The term "room temperature" as used herein refers to common ambient temperatures found in pharmaceutical laboratories ranging from about 20° C. to about 27° C.

The term "titration" as used herein refers to the incremental increase in drug dosage to a level that provides the optimal therapeutic effect.

The term "treating" refers to administering a therapy in an amount, manner, or mode effective to improve a condition, symptom, or parameter associated with a disorder.

The term "prophylaxis" refers to preventing or reducing the progression of a disorder, either to a statistically significant degree or to a degree detectable to one skilled in the art.

The term "substantially" as used herein means to a great or significant extent, but not completely.

The term "about" as used herein refers to any values, including both integers and fractional components that are within a variation of up to ±10% of the value modified by the term "about."

As used herein, "a" or "an" means one or more unless otherwise specified.

Terms such as "include," "including," "contain," "containing," "have," "having," and the like mean "comprising."

The term "or" can be conjunctive or disjunctive.

One embodiment described herein, is a topical, non-systemic, slow-releasing oral pharmaceutical composition comprising a chewable, suckable, or dissolvable soft lozenge or liquid formulation comprising one or more active pharmaceutical ingredients. In one embodiment described herein, the pharmaceutical composition slowly dissolves in a subject's oral cavity and provides contact of the active pharmaceutical ingredient to the oral cavity and esophagus over a prolonged period. In one aspect, the pharmaceutical composition can be chewed or masticated. In another aspect, the pharmaceutical composition can be sucked. In another aspect, the pharmaceutical composition can be swallowed, particularly when the composition is a liquid. In another aspect, the pharmaceutical composition can be allowed to slowly dissolve in the oral cavity. In another aspect, the pharmaceutical composition can be masticated, sucked, and/or allowed to passively dissolve in the oral cavity at the subject's discretion. Regardless of the mode of oral dissolution, the compositions described herein provide slow releasing and prolonged topical contact of the active pharmaceutical to the oral cavity and esophagus.

In one embodiment described herein, the pharmaceutical composition comprises one or more corticosteroids that are slowly released in the oral cavity and provide topical, non-systemic treatment of the oral cavity and esophagus. The dosage form of corticosteroid is topically administered to the oral cavity and esophagus, but the dosage quantity of corticosteroid is insufficient to be systemically circulated. In one aspect, the dosage form coats the esophagus. In one aspect, the oral pharmaceutical composition described herein is for the topical treatment of esophagitis or eosinophilic esophagitis (EoE).

In one embodiment described herein, the oral pharmaceutical composition comprises a chewable, suckable, or dissolvable soft lozenge. In another embodiment, the soft lozenge comprises a gelatinous solid or semi-solid fill or matrix composition that is encapsulated within a soft shell composition. In one embodiment, the pharmaceutical composition comprises a fill composition as shown in Tables 1-2 and a shell composition as shown in Tables 3-4. In another embodiment, the pharmaceutical composition comprises the formulation shown in Table 5.

One embodiment described herein, is an oral pharmaceutical composition comprising a gel mass suitable for forming a soft lozenge fill or matrix composition. In one embodiment, the soft lozenge fill or matrix composition comprises the composition shown in Table 1.

TABLE 1

Exemplary Soft Lozenge Matrix Fill Composition

| Exemplary Ingredients | Weight Percentage (%) |
| --- | --- |
| Film-forming Polymer(s) | 5-30 |
| Release Modifier(s) | 0.5-10 |
| Plasticizer(s) | 5-20 |
| pH Modifier(s) | 0.5-5 |
| Sweetener(s) | 10-80 |
| Solubilizing Agent(s) | 0.1-5 |
| Solvent(s) | 5-30 |
| Active Pharmaceutical Ingredients (API) | 0.001-1 |
| Second API | 1-10 |
| Excipients, optional | 0-10 |
| TOTAL | 100% |

Another embodiment described herein is an oral soft lozenge fill composition comprising one or more film-forming polymers, one or more plasticizers, one or more pH modifiers, one or more solubilizing agents, one or more release modifiers, one or more solvents, one or more sweeteners, and one or more active pharmaceutical ingredients. In another embodiment, the soft lozenge fill composition comprises one or more excipients, including but not limited to coloring agents, flavorings, or the like.

In one embodiment described herein, the soft lozenge fill composition comprises that shown in Table 2.

TABLE 2

Exemplary Soft Lozenge Matrix Fill Composition

| Functional Component | Exemplary Components | Weight Percentage (%) |
|---|---|---|
| Film-forming Polymers | Gelatin, 80-180 Bloom | 5-20 |
|  | Gelatin Hydrolysate | 0-10 |
| Release Modifier(s) | Polyethylene oxide, $6 \times 10^5 - 7 \times 10^6$ MW | 0.5-10 |
| Plasticizer(s) | Glycerol | 5-20 |
| pH Modifier(s) | Citrate, Lactate, Fumarate | 0.1-5 |
| Sweetener(s) | Maltitol, Mannitol | 10-70 |
|  | Xylitol | 0-10 |
|  | Sucralose | 0.1-5 |
| Solubilizing Agent(s) | Polysorbate 80 | 0.1-2 |
| Solvent | Water | 5-30 |
| Active Pharmaceutical Ingredients (API) | fluticasone, budesonide, prednisone, other corticosteroids | 0.001-0.5 |
| Second API | Lidocaine, Prilocaine, | 1-10 |
| Excipients, optional | flavorings, colorings, etc | 0-10 |
| TOTAL |  | 100% |

Another embodiment described herein is an oral soft lozenge shell composition. The shell composition is used to enrobe or encapsulate the soft lozenge fill or matrix compositions described herein. In one embodiment, the soft lozenge shell composition comprises that shown in Table 3.

TABLE 3

Exemplary Soft Lozenge Shell Composition

| Exemplary Ingredients | Weight Percentage (%) |
|---|---|
| Film-forming Polymer(s) | 10-50 |
| Plasticizer(s) | 5-20 |
| pH Modifier(s) | 0.1-5 |
| Sweetener(s) | 10-80 |
| Solvent(s) | 5-30 |
| Excipients, optional | 0-10 |
| TOTAL | 100% |

Another embodiment described herein is a composition for a soft lozenge shell composition comprising one or more film-forming polymers, one or more plasticizers, one or more pH modifiers, one or more solvents, and one or more sweeteners. In another embodiment, the soft lozenge shell composition comprises one or more excipients, including but not limited to coloring agents, flavorings, opacifiers, or the like.

In one embodiment described herein, the soft lozenge shell composition comprises that shown in Table 4.

TABLE 4

Exemplary Soft Lozenge Shell Composition

| Functional Component | Exemplary Components | Weight Percentage (%) |
|---|---|---|
| Film-forming Polymers | Gelatin, 150 Bloom (or other high Bloom) | 5-30 |

TABLE 4-continued

Exemplary Soft Lozenge Shell Composition

| Functional Component | Exemplary Components | Weight Percentage (%) |
|---|---|---|
|  | Gelatin, 100 Bloom (or other low Bloom) | 0-20 |
|  | Gelatin Hydrolysate | 0-10 |
|  | Partially Hydrolyzed Gelatin | 0-10 |
| Plasticizer(s) | Glycerol | 5-30 |
| pH Modifier(s) | Citrate, Lactate or Fumarate | 0.1-5 |
| Sweetener(s) | Mannitol, Maltitol | 5-30 |
|  | Sucralose | 0.1-2 |
|  | Xylitol | 1-10 |
| Solvent | Water | 5-30 |
| Excipients, optional | flavorings, colorings, opacifiers, etc | 0-10 |
| TOTAL |  | 100% |

Another embodiment described herein is an oral soft lozenge composition. The soft lozenge composition comprises a shell as described herein that enrobes or encapsulates a soft lozenge fill or matrix composition as described herein. In one embodiment, the soft lozenge composition comprises that shown in Table 5.

TABLE 5

Exemplary Soft Lozenge Total Composition (Shell and Fill)

| Exemplary Ingredients | Weight Percentage (%) |
|---|---|
| Film-forming Polymer(s) | 10-40 |
| Release Modifier(s) | 0.5-10 |
| Plasticizer(s) | 5-30 |
| pH Modifier(s) | 0.5-5 |
| Sweetener(s) | 10-70 |
| Solubilizing Agent(s) | 0.1-1 |
| Solvent(s) | 5-30 |
| Active Pharmaceutical Ingredients (API, e.g., corticosteroids) | 0.005-0.5 |
| Second API (topical anesthetic, e.g., lidocaine) | 1-10 |
| Excipients | 0-10 |
| TOTAL | 100% |

In one embodiment described herein, the soft lozenge composition comprises that shown in Table 6.

TABLE 6

Exemplary Soft Lozenge Total Composition (Shell and Fill)

| Component | Exemplary Components | Weight Percentage (%) |
|---|---|---|
| Film-forming Polymers | Gelatin, 150 Bloom | 1-20 |
|  | Gelatin, 100 Bloom | 1-20 |
|  | Gelatin Hydrolysate | 0-10 |
|  | Partially Hydrolyzed Gelatin | 0-10 |
| Release Modifier(s) | Polyethylene oxides, $6 \times 10^5 - 7 \times 10^6$ MW | 0.5-10 |
| Plasticizer(s) | Glycerol | 1-20 |
| pH Modifier(s) | Citric Acid, Anhydrous | 0.1-5 |
| Sweetener(s) | Maltitol (75% solution; e.g., Lycasin ® 80/55) | 10-60 |
|  | Xylitol | 0.5-5 |
|  | Sucralose | 0.01-5 |
| Solubilizing Agent(s) | Polysorbate 80 | 0.01-5 |
| Solvent | Water | 5-40 |
| Active Pharmaceutical Ingredient | Fluticasone propionate | 0.005-0.5 |

TABLE 6-continued

Exemplary Soft Lozenge Total Composition (Shell and Fill)

| Component | Exemplary Components | Weight Percentage (%) |
|---|---|---|
| Second API | Lidocaine, Prilocaine, combination thereof | 1-10 |
| Excipients | Titanium dioxide, FD&C colorings, flavors | 0-10 |
| TOTAL | | 100% |

In one embodiment described herein, the soft lozenge composition comprises a shell composition and a fill composition that have similar compositions. In one embodiment, the soft lozenge fill composition comprises similar components as the soft lozenge shell composition except that the fill composition comprises one or more solubilizing agents and one or more release modifiers and the shell composition can optionally comprise one or more opacifiers, colors, or flavors. In one embodiment described herein, the matrix fill composition is firmer and slower to dissolve in the oral cavity compared with the shell composition.

In one embodiment described herein, the pharmaceutical compositions comprise liquid dosage forms. In one aspect, the liquid dosage form comprises a suspension. In another aspect, the liquid dosage form comprises syrup. In another aspect, the liquid dosage form comprises a concentrate.

Another embodiment described herein is a composition for a liquid dosage form comprising one or more release modifiers, one or more film forming polymers, one or more plasticizers, one or more, pH modifiers, one or more sweeteners, one or more solubilizing agents, and one or more solvents. In another embodiment, the liquid dosage form comprises one or more excipients, including but not limited to coloring agents, flavorings, opacifiers, thickeners or the like.

In one embodiment described herein, the pharmaceutical compositions described herein comprise one or more film-forming polymers. Film-former polymers that are useful for the pharmaceutical compositions described herein are gelatin, partially hydrolyzed gelatin, collagen, partially hydrolyzed collagen; sodium or calcium alginate; natural and modified starch, starch hydrolysates, pectins or amylopectins; hydroxypropylmethylcellulose (HPMC), methylcellulose, cellulose; carrageenan (e.g., iota carrageenan and kappa carrageenan), or combinations thereof. In one embodiment described herein, the pharmaceutical compositions comprise one or more film-forming polymers comprising one or more gelatins or gelatin hydrolysates.

Examples of gelatin compositions that are useful for the pharmaceutical compositions described herein comprise acid bone gelatin, pig skin gelatin, chicken skin gelatin, fish gelatin, acid hide gelatin, gelatin hydrolysate, lime bone gelatin, or combinations thereof. Gelatins are often classified as either "Type A" or "Type B" gelatin. Type A gelatin is derived from the acid hydrolysis of collagen (e.g., acid bone gelatin or pig skin gelatin), while Type B gelatin (e.g., lime bone gelatin) is derived from the alkaline hydrolysis of collagen. Traditionally, bovine bones and skins are used as raw materials for manufacturing Type A and Type B gelatin, while porcine skins are used extensively for manufacturing Type A gelatin. In addition, at neutral pH values, Type A gelatins (e.g., acid-processed gelatins) are typically net cationic (e.g., isoelectric point of about 7-9) and Type B gelatins (e.g., alkali-processed gelatins) are typically net anionic (e.g., isoelectric point of about 4.5-5.3). Type A gelatin typically has higher plasticity and elasticity than type B gelatin; type B gelatin typically has higher gel strength than type A gelatin.

The strength of gelatins is typically defined by "Bloom strength" or grade. The Bloom test determines the weight (in grams) needed by a 0.5-inch diameter probe to deflect the surface of a gel 4-mm without breaking it. The result is expressed as "Bloom" or "Bloom strength." The pharmaceutical compositions described herein utilize gelatins with Bloom strengths in the range of about 20 Bloom to about 400 Bloom, including each integer within the specified range. In one embodiment, Bloom strengths for the pharmaceutical compositions described herein are about 50 Bloom to about 250 Bloom including each integer within the specified range. In some embodiments, the gelatin Bloom strength is about 50 Bloom, about 80 Bloom, about 100 Bloom, about 120 Bloom, about 150 Bloom, about 180 Bloom, about 200 Bloom, or about 250 Bloom. In one embodiment, the gelatin Bloom strength is about 100 Bloom. In another embodiment, the gelatin Bloom strength is about 150 Bloom. In another embodiment, the gelatin Bloom strength is 195 Bloom. In another embodiment, the gelatin Bloom strength is 200 Bloom. In another aspect, the film-forming polymers comprise one or more of gelatin with various Bloom strengths, partially hydrolyzed gelatin, hydrolyzed gelatin, or combinations thereof.

In another embodiment described herein, the pharmaceutical compositions described herein comprises one or more plasticizers. As used herein, a plasticizer is a substance, often a polyol that provides flexibility and softens the lozenge. In one embodiment, the plasticizer comprises one or more of glycerol, sorbitol, partially dehydrated sorbitol (a blend of D-sorbitol, 1,4-sorbitan, mannitol, and water; e.g., Sorbitol Special® (SPI Pharma); Anidrisorb® or Polysorb®, (Roquette), corn syrup, xylitol, mannitol, propylene glycol, low molecular weight polyethylene glycols, poly-alcohols with 3 to 6 carbon atoms, or combinations thereof. In one embodiment, the plasticizer comprises glycerol, sorbitol, or combinations thereof.

In another embodiment described herein, the pharmaceutical compositions described herein comprise one or more sweeteners. In one embodiment, the sweetener comprises one or more of maltitol (e.g., hydrogenated starch hydrolysates; e.g., Lycasin® 80/55, Roquette), xylitol (Xylisorb 300), sucralose, aspartame, steviol glycosides (e.g., Stevia, Truvia), thaumatin (e.g., Talin®), glycyrrhizic acid salts (MagnaSweet®), mannitol, or combinations thereof. In one aspect, the sweetener comprises sucralose, sucrose, xylitol, or combinations thereof.

In another embodiment described herein, the pharmaceutical composition comprises one or more pH modifiers. In one embodiment, the pH modifier comprises one or more organic acids. In another embodiment, the pH modifier comprises one or more of citric acid, acetic acid, lactic acid, malic acid, tartaric acid, glutamic acid, aspartic acid, malic acid, succinic acid, fumaric acid, or combinations thereof. In one aspect, the pH modifier comprises citric acid, lactic acid, or fumaric acid. In one aspect, the pH modifier comprises citric acid.

In another embodiment described herein, the pharmaceutical composition comprises one or more solubilizing agents. In one embodiment, the solubilizing agent comprises one or more of polysorbate 20, polysorbate 40, polysorbate 60, polysorbate 80, diethanolamine, glyceryl monostearate, lanolin alcohols, lecithin, mono- and di-glycerides, monoethanolamines, oleic acids, oleyl alcohols, poloxamer, polyoxyethylene 50 stearate, polyoxyl 35 castor oil, polyoxyl 40 hydrogenated castor oil, polyoxyl 10 oleyl ether, polyoxyl 20 cetostearyl ether, polyoxyl 40 stearate, propylene glycol diacetate, propylene glycol monostearate, sodium lauryl sulfate, sodium stearate, sorbitan monolaurate, sorbitan monooleate, sorbitan monopalmitate, sorbitan monostearate, stearic acid, trolamine, emulsifying wax, or combinations thereof. In one aspect, the solubilizing agent comprises polysorbate 80.

In another embodiment described herein, the pharmaceutical composition comprises one or more release modifiers. Suitable release modifiers comprise one or more of polyethylene oxides, methylcellulose, hydroxypropylmethyl cellulose, hydroxypropyl cellulose, hydroxyethyl cellulose, hydroxymethyl cellulose, polymethylmethacrylate, polyhydroxyethylmethacrylate, polyvinylpyrrolidone, copovidone, polyvinyl alcohol, copolymers of polyvinylpyrrolidone and polyvinyl acetate, or combinations thereof. For example, Methocel™ K100M, Methocel™ A4M, Premium LV CR, K4M Premium CR, K15M Premium CR, K100 Premium CR, E4M Premium CR, E10M Premium CR, or E4M Premium (Dow Chemical Co.), CELLOSIZE™, or WALOCEL™ CRT may be used as release modifiers in the compositions described herein. In one embodiment described herein, the release modifier comprises one or more polyethylene oxides.

In one embodiment described herein, the release modifier comprises a polyethylene oxide. As described herein, polyethylene oxide polymers have an approximate molecular weight ($M_v$) of at least about 600,000 to about 10,000,000 or greater. In one aspect, the release modifier may comprise a high molecular weight polyethylene oxide having a molecular weight ($M_v$) of about 600,000 to about 10,000,000, including each integer within the specified range. In another aspect, the release modifier may comprise a high molecular weight polyethylene oxide having a molecular weight ($M_v$) of about 4,000,000 to about 10,000,000, including each integer within the specified range. In another aspect, the release modifier may comprise a high molecular weight polyethylene oxide having a molecular weight ($M_v$) of about 4,000,000 to about 8,000,000, including each integer within the specified range. In another aspect, the release modifier may comprise a polyethylene oxide having a molecular weight ($M_v$) of about 600,000, about 700,000, about 800,000, about 900,000, about 1,000,000, about 2,000,000, about 3,000,000, about 4,000,000, about 5,000,000, about 6,000,000, about 7,000,000, about 8,000,000, about 9,000,000 or about 10,000,000. In another aspect, the release modifier may comprise a high molecular weight polyethylene oxide having a molecular weight ($M_v$) of about 4,000,000. In another aspect, the release modifier may comprise a high molecular weight polyethylene oxide having a molecular weight ($M_v$) of about 5,000,000. In another aspect, the release modifier may comprise a high molecular weight polyethylene oxide having a molecular weight ($M_v$) of about 7,000,000.

The molecular weight measurements of polyethylene oxide may be approximated using rheological measurements using a viscometer (e.g., weight average molecular weight, $M_v$). For example, polyethylene oxide is considered to have an approximate molecular weight ($M_v$) of 600,000 when a 5% (by wt) aqueous solution of polyethylene oxide using a Brookfield viscometer Model RVF, spindle No. 2, at 2 rpm, at 25° C. shows a viscosity range of 30 to 50 mPa s (cP). Polyethylene oxide is considered to have an approximate molecular weight ($M_v$) of 1,000,000 when a 2% (by wt) aqueous solution of polyethylene oxide using a Brookfield viscometer Model RVF, spindle No. 1, at 10 rpm, at 25° C. shows a viscosity range of 400 to 800 mPa s (cP). Polyethylene oxide is considered to have an approximate molecular weight ($M_v$) of 2,000,000 when a 2% (by wt) aqueous solution of polyethylene oxide using a Brookfield viscometer Model RVF, spindle No. 3, at 10 rpm, at 25° C. shows a viscosity range of 2000 to 4000 mPa s (cP). Polyethylene oxide is considered to have an approximate molecular weight ($M_v$) of 4,000,000 when a 1% (by wt) aqueous solution of polyethylene oxide using a Brookfield viscometer Model RVF, spindle No. 2, at 2 rpm, at 25° C. shows a viscosity range of 1650 to 5500 mPa s (cP). Polyethylene oxide is considered to have an approximate molecular weight ($M_v$) of 4,000,000 when a 2% (by wt) aqueous solution of polyethylene oxide using a Brookfield viscometer Model RVF, spindle No. 2, at 2 rpm, at 25° C. shows a viscosity range of 3300 to 11000 mPa s (cP). Polyethylene oxide is considered to have an approximate molecular weight ($M_v$) of 5,000,000 when a 1% (by wt) aqueous solution of polyethylene oxide using a Brookfield viscometer Model RVF, spindle No. 2, at 2 rpm, at 25° C. shows a viscosity range of 5500 to 7500 mPa s (cP). Polyethylene oxide is considered to have an approximate molecular weight ($M_v$) of 5,000,000 when a 1.5% (by wt) aqueous solution of polyethylene oxide using a Brookfield viscometer Model RVF, spindle No. 2, at 2 rpm, at 25° C. shows a viscosity range of 8250 to 11250 mPa s (cP). Polyethylene oxide is considered to have an approximate molecular weight ($M_v$) of 7,000,000 when a 1% (by wt) aqueous solution of polyethylene oxide using a Brookfield viscometer Model RVF, spindle No. 2, at 2 rpm, at 25° C. shows a viscosity range of 7500 to 10,000 mPa s (cP). Polyethylene oxide is considered to have an approximate molecular weight ($M_v$) of 8,000,000 when a 1% (by wt) aqueous solution of polyethylene oxide using a Brookfield viscometer Model RVF, spindle No. 2, at 2 rpm, at 25° C. shows a viscosity range of 10,000 to 15,000 mPa s (cP). Suitable polyethylene oxide polymers with the above described viscosity and molecular weight ($M_v$) values that are useful for the matrices described are, for example, POLYOX™ polymers, such as WSR-205, WSR-1105, WSR N-12K, WSR N-60K, WSR-301, WSR Coagulant, WSR-303, WSR 308, UCARFLOC Polymers 300, 302, 304, and 309 commercially available from Dow. In one embodiment described herein, the release modifier comprises the polyethylene oxide polymer Polyox™ WSR-303 that has an approximate molecular weight (viscosity average, $M_v$) of 7,000,000 and a 1% solution of the polymer has a viscosity of 7,500-10,000 cP at 25° C. using a Brookfield Model RVF viscometer, spindle No. 2, at 2 rpm.

The one or more release modifiers may comprise a viscosity of about 50 cP to about 100,000 cP, including each integer within the specified range. For example, the release modifiers comprise a viscosity of about 50 cP, about 100 cP, about 200 cP, about 300 cP, about 400 cP, about 500 cP, about 750 cP, about 1,000 cP, about 1,500 cP, about 2,000 cP, about 2,500 cP, about 3,000 cP, about 3,500 cP, about 4,000 cP, about 4,500 cP, about 5,000 cP, about 6,000 cP, about 7,000 cP, about 8,000 cP, about 9,000 cP, or about 10,000 cP, about 15,000 cP, about 20,000 cP, about 30,000 cP, about 40,000 cP, about 50,000 cP, about 60,000 cP, about 70,000 cP, about 80,000 cP, about 90,000 cP, about 100,000 cP, greater than 100,000 cP, or even greater.

In one embodiment described herein, the one or more release modifiers provide slow release of the active pharmaceutical ingredient by retarding the dissolution of the dosage form.

In another embodiment described herein, in addition to the release modifiers, thickening agents may be used to control the release of the active pharmaceutical ingredient and may comprise one or more of polyacrylic acid, methylcellulose, alginic acid, chitosan, carboxymethyl cellulose, sodium carboxymethyl cellulose, locust bean gum, xanthum gum, high swelling crosslinked polymers, or combinations thereof.

In another embodiment described herein, the pharmaceutical compositions described herein comprises one or more solvents. In one aspect, the solvent comprises water.

In another embodiment described herein, the pharmaceutical compositions described herein comprises one or more active pharmaceutical ingredients. In one embodiment, the active pharmaceutical ingredient comprises one or more corticosteroids. In another embodiment, the active pharmaceutical ingredient comprises one or more corticosteroids and one or more topical anesthetics. In one embodiment, the active pharmaceutical composition comprises fluticasone propionate, lidocaine, prilocaine, or combinations thereof.

In one embodiment described herein, one or more film-forming polymers comprise about 5% to about 70% by weight of the composition, including each integer within the specified range. In another embodiment, one or more film-forming polymers comprise about 5% to about 30% by weight of the composition, including each integer within the specified range. In another embodiment, one or more film-forming polymers comprise about 10% to about 60% by weight of the composition, including each integer within the specified range. In another embodiment, one or more film-forming polymers comprise about 10% to about 40% by weight of the composition, including each integer within the specified range. In one aspect, one or more film-forming polymers comprise about 5% to about 20%; about 1% to about 10%; about 5% to about 15%; about 1% to about 5%; about 10% to about 20%; about 15% to about 20%; about 10% to about 15%, or about 1% to about 5% by weight of the composition, including each integer within the specified ranges.

In another embodiment described herein, one or more film-forming polymers comprise about 0.5%, about 1%, about 2%, about 2.5%, about 3%, about 4%, about 5%, about 6%, about 7.5%, about 8%, about 9%, about 10%, about 11%, about 12%, about 13%, about 14%, about 15%, about 16%, about 17%, about 18%, about 19%, about 20%, or about 25% by weight of the composition.

In one embodiment described herein, one or more plasticizers comprise about 5% to about 30% by weight of the composition, including each integer within the specified range. In another embodiment, one or more plasticizers comprise about 5% to about 20% by weight of the composition, including each integer within the specified range. In another embodiment, one or more plasticizers comprise about 10% to about 30% by weight of the composition, including each integer within the specified range. In another embodiment, one or more plasticizers comprise about 5% to about 10% by weight of the composition, including each integer within the specified range. In another embodiment, one or more plasticizers comprise about 10% to about 20% by weight of the composition, including each integer within the specified range. In one aspect, one or more plasticizers comprise about 5% to about 20%; about 1% to about 10%; about 5% to about 15%; about 1% to about 5%; about 10% to about 20%; about 15% to about 20%; about 10% to about 15%, or about 1% to about 5% by weight of the composition, including each integer within the specified ranges.

In another embodiment described herein, one or more plasticizers comprise about 5%, about 6%, about 7.5%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, or about 30% by weight of the composition.

In one embodiment, one or more pH modifiers comprise about 0.1% to about 5% by weight of the composition, including each integer within the specified range. In another embodiment, one or more pH modifiers comprise about 0.1% to about 1% by weight of the composition, including each integer within the specified range. In another embodiment, one or more pH modifiers comprise about 0.5% to about 1% by weight of the composition, including each integer within the specified range. In another embodiment, one or more pH modifiers comprise about 0.1% to about 0.5% by weight of the composition, including each integer within the specified range. In one aspect, one or more pH modifiers comprise about 0.1% to about 0.5%; about 0.5% to about 1%; about 0.25% to about 0.75%; about 0.75% to about 1%; about 1% to about 2%; about 0.5% to about 1.5%; about 0.5% to about 0.75%, or about 0.25% to about 0.5% by weight of the composition, including each integer within the specified ranges.

In another embodiment described herein, one or more pH modifiers comprise about 0.1%, about 0.2%, about 0.35, about 0.4%, about 0.5%, about 0.6%, about 0.7%, about 0.8%, about 0.9%, about 1%, about 1.2%, about 1.3%, about 1.4%, about 1.5%, about 1.6%, about 1.7%, about 1.8%, about 1.9%, about 2%, about 2.5%, about 3%, about 4%, or about 5% by weight of the composition.

In one embodiment, one or more release modifiers comprise about 0.5% to about 10% by weight of the composition, including each integer within the specified range. In another embodiment, one or more release modifiers comprise about 1% to about 5% by weight of the composition, including each integer within the specified range. In another embodiment, one or more release modifiers comprise about 2% to about 5% by weight of the composition, including each integer within the specified range. In one aspect, one or more release modifiers comprise about 0.5% to about 2%; about 1% to about 3%; about 2% to about 4%; about 2.5% to about 5%; about 0.5% to about 1%; about 1% to about 2%; about 2% to about 3%; about 3% to about 4%; or about 4% to about 5% by weight of the composition, including each integer within the specified ranges.

In another embodiment described herein, one or more release modifiers comprise about 0.2%, about 0.5%, about 1%, about 2%, about 3%, about 4%, about 5%, about 1.1%, about 1.2%, about 1.3%, about 1.4%, about 1.5%, about 1.6%, about 1.7%, about 1.8%, about 1.9%, about 2.2%, about 2.4%, about 2.6%, about 2.8%, about 2.9% about 3.1%, about 3.2%, about 3.4%, about 3.6%, about 3.8%, about 4.1%, about 4.2%, about 4.4%, about 4.6%, about 4.8%, about 5.5%, about 6%, about 7%, about 8%, about 9%, or about 10% by weight of the composition.

In one embodiment described herein, one or more sweeteners comprise about 10% to about 80% by weight of the composition, including each integer within the specified range. In another embodiment described herein, one or more sweeteners comprise about 30% to about 70% by weight of the composition, including each integer within the specified range. In another embodiment described herein, one or more sweeteners comprise about 15% to about 30% by weight of the composition, including each integer within the specified range. In another embodiment described herein, one or more sweeteners comprise about 20% to about 60% by weight of the composition, including each integer within the specified range. In one aspect, one or more release modifiers comprise about 0.1% to about 0.2%; about 0.1% to about 0.3%; about 0.1% to about 2%; about 1% to about 2.5%; about 1% to about 5%; about 2.5% to about 5%; about 1% to about 10%; about 10% to about 15%, about 15% to about 20%; about 20% to about 30%, about 30% to about 40%; about 40% to about 45%; about 45% to about 50%; about 40% to about 50%; about 50% to about 60%; about 55% to about 60%; about 60% to about 65%; about 60% to about 70%; or about 70% to about 80% by weight of the composition, including each integer within the specified ranges.

In another embodiment described herein, one or more sweeteners comprise about 0.1%; about 0.2%, about 0.3%, about 0.4%, about 0.5%, about 1%, about 2%, about 3%; about 4%, about 5%, about 6%, about 7%, about 8%, about 9%, about 10%, about 11%, about 12%, about 13%; about 14%, about 15%, about 16%, about 17%, about 18%, about 19%, about 20%, about 25%, about 30%, about 35%, about 40%, about 42%, about 45%, about 50%, about 55%, about 58%, about 60%, about 62%, about 65%, or about 70% by weight of the composition.

In one embodiment described herein, one or more solubilizing agents comprise about 0.1% to about 1% by weight of the composition, including each integer within the specified range.

In another embodiment described herein, one or more solubilizing agents comprise 0.1% to about 0.5% by weight of the composition, including each integer within the specified range. In another embodiment described herein, one or more solubilizing agents comprise 0.1% to about 0.25% by weight of the composition, including each integer within the specified range. In one aspect, one or more solubilizing agents comprise about 0.1% to about 0.5%; about 0.5% to about 0.75%; about 0.25% to about 0.5%; about 0.2% to about 0.7%; about 0.5% to about 1%; about 0.75% to about 1%; about 0.4% to about 0.7%; about 0.3% to about 0.6%; about 0.4% to about 0.8%; about 0.25% to about 0.75%; about 0.3% to about 0.9%; or about 0.75% to about 1% by weight of the composition, including each integer within the specified ranges.

In another embodiment described herein, one or more solubilizing agents comprise about 0.1%, about 0.2, about 0.3, about 0.35, about 0.4%, about 0.45%, about 0.5%, about 0.6%, about 0.7%, about 0.8%, about 0.9%, or about 1%, by weight of the composition.

In one embodiment described herein, one or more solvents comprise about 5% to about 30% by weight of the composition, including each integer within the specified range. In another embodiment described herein, one or more one or more solvents comprise about 10% to about 20% by weight of the composition, including each integer within the specified range. In another embodiment described herein, one or more one or more solvents comprise about 20% to about 30% by weight of the composition, including each integer within the specified range. In another embodiment described herein, one or more one or more solvents comprise about 20% to about 25% by weight of the composition, including each integer within the specified range. In one aspect, one or more solvents comprise about 5% to about 20%; about 10% to about 15%; about 10% to about 20%; about 15% to about 20%; about 15% to about 25%; about 15% to about 30%; about 20% to about 25%; about 20% to about 30%; or about 25% to about 30% by weight of the composition, including each integer within the specified ranges.

In another embodiment described herein, one or more solvents comprise about 5%, about 7.5%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, or about 30% by weight of the composition.

In one embodiment described herein, one or more active pharmaceutical ingredients comprise about 0.005% to about 5% by weight of the composition, including each integer within the specified range. In another embodiment described herein, one or more active pharmaceutical ingredients comprise about 0.025% to about 0.05% by weight of the composition, including each integer within the specified range. In another embodiment described herein, one or more active pharmaceutical ingredients comprise about 0.015% to about 0.035% by weight of the composition, including each integer within the specified range. In one aspect described herein, one or more active pharmaceutical ingredients comprise about 0.005% to about 0.01%; about 0.01% to about 0.05%; about 0.01% to about 0.025%; about 0.025% to about 0.1%; about 0.05% to about 0.1%; about 0.016% to about 0.032%; about 0.02% to about 0.04%; about 0.02% to about 0.05%; about 0.01% to about 0.04%; or about 0.02% to about 0.04% by weight of the composition, including each integer within the specified ranges.

In another embodiment described herein, one or more active pharmaceutical ingredients comprise about 0.01%, about 0.016%, about 0.02%, about 0.025%, about 0.03%, about 0.032%, about 0.04%, about 0.05%, about 0.06%, about 0.07%, about 0.08%, about 0.09%, about 0.1%, about 0.2%, about 0.3%, about 0.4%, about 0.5%, about 0.6%, about 0.7%, about 0.8%, about 0.9%, about 1%, about 2%, about 3%, about 4%, or about 5% by weight of the composition.

In another embodiment described herein, one or more second active pharmaceutical ingredients comprise about 0.1%, about 0.2%, about 0.3%, about 0.4%, about 0.5%, about 0.6%, about 0.7%, about 0.8%, about 0.9%, about 1%, about 2%, about 3%, about 4%, or about 5% by weight of the composition.

In one embodiment described herein, one or more pharmaceutically acceptable excipients comprise about 0.0001% to about 10% by weight of the composition, including each integer within the specified range. In another embodiment described herein, one or more pharmaceutically acceptable excipients comprise about 0.1% to about 2% by weight of the composition, including each integer within the specified range. In another embodiment described herein, one or more pharmaceutically acceptable excipients comprise about 0.1% to about 1% by weight of the composition, including each integer within the specified range. In one aspect, one or more pharmaceutically acceptable excipients comprise about 0.1% to about 0.4%; 0.1% to about 0.5%; about 0.5% to about 1%; about 1% to about 1.5%, about 0.4% to about 1.2%; about 2% to about 5%; or about 5% to about 10% by weight of the composition, including each integer within the specified ranges.

In another embodiment described herein, one or more pharmaceutically acceptable excipients comprise about 0.0006%, about 0.0017%, about 0.1%, about 0.2%, about 0.3%, about 0.4%, about 0.5%, about 0.6%, about 0.7%, about 0.8%, about 0.9%, about 1%, about 1.1%, about 1.2%, about 1.3%, about 1.4%, about 1.5%, about 1.6%, about 1.7%, about 1.8%, about 2%, about 3%, about 4%, or about 5% by weight of the composition.

In another embodiment described herein, the one or more film-forming polymers comprise gelatin having a Bloom of about 100 to about 150 and a weight percentage of about 5% to about 30% by weight of the composition, including each integer within the specified range. In one embodiment, gelatin having a Bloom of about 50 to 150 comprises about 5% to about 10%; about 10% to about 15%; 10% to about 20%; about 15% to about 20%; about 20% to about 25%; or about 25% to about 30% by weight of the composition, including each integer within the specified ranges. In one aspect, gelatin having a Bloom of about 50 to 150 comprises about 5%, about 7.5%, about 8%, about 9%, about 10%, about 11%, about 12%, about 13%, about 14%, about 15%, about 16%, about 17%, about 18%, about 19%, about 20%, about 25%, or about 30% by weight of the composition.

In another embodiment described herein, the one or more film-forming polymers comprise a gelatin having a Bloom of about 50 to about 100 and a weight percentage of about 1% to about 20% by weight of the composition, including each integer within the specified range. In another embodiment, gelatin having a Bloom of about 50 to about 100 comprises about 1% to about 5%; about 2.5% to about 5%; about 5% to about 10%; about 10% to about 15%; about 2.5% to about 10%; or about 4.7% to about 13% by weight of the composition, including each integer within the specified ranges. In one aspect, gelatin having a Bloom of about 100 comprises about 1%, about 2%, about 2.5%, about 3%, about 4%, about 4.7%, about 5%, about 6%, about 7%, about 8%, about 9%, about 10%, about 11%, about 12%, about 13%, about 14%, about 15%, about 16%, about 17%, about 18%, about 19%, or about 20% by weight of the composition.

In another embodiment described herein, the one or more film-forming polymers comprise gelatin hydrolysate at a weight percentage of about 0.5% to about 5% by weight of the composition, including each integer within the specified range. In one embodiment, gelatin hydrolysate comprises about 0.5% to about 1%; about 1% to about 2.5%; or about 0.5% to about 2.5% by weight of the composition, including each integer within the specified ranges. In one aspect, gelatin hydrolysate comprises about 0.1%, about 0.25%, about 0.5%, about 0.75%, about 0.9%, about 1%, about 1.5%, about 2%, about 2.5%, about 3%, about 4%, or about 5%, by weight of the composition.

In another embodiment described herein, the one or more film-forming polymers comprise partially hydrolyzed gelatin at a weight percentage of about 0.5% to about 5% by weight of the composition, including each integer within the specified range. In one embodiment, the partially hydrolyzed gelatin comprises about 0.5% to about 1%; about 1% to about 2.5%; or about 0.5% to about 2.5% by weight of the composition, including each integer within the specified ranges. In one aspect, partially hydrolyzed gelatin comprises about 0%, 0.1%, about 0.25%, about 0.5%, about 0.75%, about 0.9%, about 1%, about 1.5%, about 2%, about 2.5%, about 3%, about 4%, or about 5%, by weight of the composition.

In another embodiment described herein, one or more plasticizers comprise glycerol at a weight percentage of about 5% to about 30% by weight of the composition, including each integer within the specified range. In one embodiment, glycerol comprises about 5% to about 20%; about 1% to about 10%; about 5% to about 15%; about 1% to about 5%; about 10% to about 20%; about 15% to about 20%; about 10% to about 15%; or about 1% to about 5% by weight of the composition, including each integer within the specified ranges. In one aspect, glycerol comprises about 5%, about 6%, about 7.5%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, or about 30% by weight of the composition.

In another embodiment described herein, the one or more pH modifiers comprise citric acid (citrate) about 0.1% to about 5% by weight of the composition, including each integer within the specified range. In one embodiment, citrate comprises about 0.1% to about 0.5%; about 0.5% to about 1%; about 0.25% to about 0.75%; about 0.75% to about 1%; about 1% to about 2%; about 0.5% to about 1.5%; about 0.5% to about 0.75%, or about 0.25% to about 0.5% by weight of the composition, including each integer within the specified ranges. In one aspect, citrate comprises comprise about 0.1%, about 0.2%, about 0.35, about 0.4%, about 0.5%, about 0.6%, about 0.7%, about 0.8%, about 0.9%, about 1%, about 1.2%, about 1.3%, about 1.4%, about 1.5%, about 1.6%, about 1.7%, about 1.8%, about 1.9%, about 2%, about 2.5%, about 3%, about 4%, or about 5% by weight of the composition.

In one embodiment described herein, the one or more release modifiers comprise a polyethylene oxide polymer, having a molecular weight between $6 \times 10^5$ and $7 \times 10^6$ MW, at a weight percentage of about 1% to about 10% by weight of the composition, including each integer within the specified range. In one embodiment, the polyethylene oxide polymer comprises about 0.5% to about 2%; about 1% to about 3%; about 2% to about 4%; about 2.5% to about 5%; about 0.5% to about 1%, about 1% to about 2%; about 2% to about 3%; about 3% to about 4%; or about 4% to about 5% by weight of the composition, including each integer within the specified ranges. In one aspect, the polyethylene oxide polymer, having a molecular weight between 1 million and 7 million, comprises about 0.2%, about 0.5%, about 1%, about 2%, about 3%, about 4%, about 5%, about 1.1%, about 1.2%, about 1.3%, about 1.4%, about 1.5%, about 1.6%, about 1.7%, about 1.8%, about 1.9%, about 2.2%, about 2.4%, about 2.6%, about 2.8%, about 2.9% about 3.1%, about 3.2%, about 3.4%, about 3.6%, about 3.8%, about 4.1%, about 4.2%, about 4.4%, about 4.6%, about 4.8%, about 5.5%, about 6%, about 7%, about 8%, about 9%, or about 10% by weight of the composition.

In another embodiment described herein, the sweetener comprises maltitol (e.g., Lycasin® 80/55) at a weight percentage of about 10% to about 60%, by weight of the composition, including each integer within the specified range. In one embodiment, maltitol comprises about 40% to about 60%; about 5% to about 20%; about 30% to about 45% by weight of the composition, including each integer within the specified ranges. In one embodiment, maltitol comprise about 5%, about 7.5%, about 10%, about 12%, about 14% about 16%, about 18%, about 20%, about 22%, about 24%; about 26%, about 28%, about 30%, about 32%, about 34%, about 35%, about 36%, about 38%, about 40%, about 41%, about 42%, about 44% about 45%, about 46%, about 48%, about 50%, about 52%, about 54%, about 56%, about 58%, or about 60% by weight of the composition.

In another embodiment described herein, the sweetener comprises xylitol (e.g., Xylisorb 300®) at a weight percentage of about 1% to about 10% by weight of the composition, including each integer within the specified range. In one embodiment, xylitol comprises about 1% to about 5%, about 0.5% to about 4%; about 1% to about 3.5%; about 1.5% to about 3%, about 2.5% to about 5%; or about 2.5% to about 3.5% by weight of the composition, including each integer within the specified ranges. In one aspect, xylitol comprises about 1%, about 1.5%, about 2%, about 2.5%, about 3%, about 3.5%, about 3.6%, about 4%, about 4.3%, about 4.5%, or about 5% by weight of the composition.

In another embodiment described herein, the sweetener comprises sucralose comprise a weight percentage of about 0.1% to about 2% by weight of the composition, including each integer within the specified range. In one embodiment, sucralose comprises about 0.1% to about 0.2%; about 0.2% to about 0.3%; about 0.3% to about 0.4%; about 0.25% to about 0.4%; or about 0.2% to about 0.5% by weight of the composition, including each integer within the specified ranges. In one aspect, sucralose comprises about 0.2%, about 0.3%, about 0.4%, or about 0.5% by weight of the composition.

In one embodiment described herein, the one or more solubilizing agents comprise polysorbate 80 at a weight percentage of about 0.1% to about 1% by weight of the composition, including each integer within the specified range. In one embodiment, polysorbate 80 comprises about 0.2% to about 1%; about 0.3% to about 0.8%; about 0.3% to about 0.5%; about 0.6% to about 0.8%; 0.35% to about 0.45%; or about 0.65% to about 0.75% by weight of the composition including each integer within the specified ranges. In one aspect, polysorbate 80 comprises comprise about 0.1%, about 0.2, about 0.3, about 0.35, about 0.4%, about 0.45%, about 0.5%, about 0.6%, about 0.7%, about 0.8%, about 0.9%, or about 1%, by weight of the composition.

In another embodiment described herein, the solvent comprises water at a weight percentage of about 5% to about 30% by weight of the composition, including each integer within the specified range. In another embodiment, water comprises 5% to about 20%; about 10% to about 15%; about 10% to about 20%; about 15% to about 20%; about 15% to about 25%; about 15% to about 30%; about 20% to about 25%; about 20% to about 30%; or about 25% to about 30% by weight of the composition, including each integer within the specified ranges. In one aspect, water comprises about 5%, about 7.5%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, or about 30% by weight of the composition.

In another embodiment described herein, the active pharmaceutical ingredient comprises fluticasone or a pharmaceutically acceptable salt thereof at a weight percentage of about 0.005% to about 5% by weight of the composition, including each integer within the specified range. In one embodiment, fluticasone comprises about 0.005 to about 0.01%; about 0.01% to about 0.05%; about 0.01% to about 0.025%; about 0.025% to about 0.1%; about 0.05% to about 0.1%; about 0.016% to about 0.032%; about 0.02% to about 0.04%; about 0.02% to about 0.05%; about 0.01% to about 0.04%; or about 0.02% to about 0.04% by weight of the composition, including each integer within the specified ranges. In one aspect, fluticasone comprises about 0.01%, about 0.016%, about 0.02%, about 0.025%, about 0.03%, about 0.032%, about 0.04%, about 0.05%, about 0.06%, about 0.07%, about 0.08%, about 0.09%, about 0.1%, about 0.2%, about 0.3%, about 0.4%, about 0.5%, about 0.6%, about 0.7%, about 0.8%, about 0.9%, or about 1% by weight of the composition.

In another embodiment described herein, the second active pharmaceutical ingredient comprises lidocaine, prilocaine, or a combination thereof, or a pharmaceutically acceptable salt thereof at a weight percentage of about 0.5% to about 10% by weight of the composition, including each integer within the specified range. In one embodiment, fluticasone comprises about 0.5 to about 1%; about 1% to about 1.5%; about 1% to about 3%; about 1% to about 5%; about 2% to about 5%; about 3% to about 5%; about 4% to about 5%; about 0.5% to about 5%; about 2.5% to about 5%; or about 0.5% to about 2.5% by weight of the composition, including each integer within the specified ranges. In one aspect, fluticasone comprises about 0.5%, about 0.75%, about 1%, about 1.5%, about 2%, about 2.5%, about 3%, about 3.5%, about 4%, about 4.5%, about 5%, about 6%, about 7%, about 8%, about 9%, or about 10% by weight of the composition.

In another embodiment described herein, the pharmaceutical composition described herein comprises one or more optional pharmaceutically acceptable excipients. In one embodiment, the excipient comprises an opacifier such as titanium dioxide at a weight percentage of about 0.2% to about 2%, including each integer within the specified range. In another embodiment, the excipient comprises one or more coloring agents at a weight percentage of about 0.0001% to about 0.5%, including each integer within the specified range. In another embodiment, the excipient comprises one or more flavor at a weight percentage of about 0.1% to about 4%, including each integer within the specified range. In another embodiment, the pharmaceutical composition comprises a combination of excipients, including opacifiers, coloring agents, or flavors.

Additional pharmaceutical excipients useful for the pharmaceutical composition as described herein include, for example, the following: acidifying agents (acetic acid, glacial acetic acid, citric acid, fumaric acid, hydrochloric acid, diluted hydrochloric acid, malic acid, nitric acid, phosphoric acid, diluted phosphoric acid, sulfuric acid, tartaric acid); alkalizing agents (ammonia solution, ammonium carbonate, diethanolamine, diisopropanolamine, potassium hydroxide, sodium bicarbonate, sodium borate, sodium carbonate, sodium hydroxide, trolamine); antifoaming agents (dimethicone, simethicone); antimicrobial preservatives (benzalkonium chloride, benzalkonium chloride solution, benzethonium chloride, benzoic acid, benzyl alcohol, butylparaben, cetylpyridinium chloride, chlorobutanol, chlorocresol, cresol, dehydroacetic acid, ethylparaben, methylparaben, methylparaben sodium, phenol, phenylethyl alcohol, phenylmercuric acetate, phenylmercuric nitrate, potassium benzoate, potassium sorbate, propylparaben, propylparaben sodium, sodium benzoate, sodium dehydroacetate, sodium propionate, sorbic acid, thimerosal, thymol); antioxidants (ascorbic acid, ascorbyl palmitate, butylated hydroxyanisole, butylated hydroxytoluene, hypophosphorous acid, monothioglycerol, propyl gallate, sodium formaldehyde sulfoxylate, sodium metabisulfite, sodium thiosulfate, sulfur dioxide, tocopherol, tocopherols excipient); buffering agents (acetic acid, ammonium carbonate, ammonium phosphate, boric acid, citric acid, lactic acid, phosphoric acid, potassium citrate, potassium metaphosphate, potassium phosphate monobasic, sodium acetate, sodium citrate, sodium lactate solution, dibasic sodium phosphate, monobasic sodium phosphate); chelating agents (edetate disodium, ethylenediaminetetraacetic acid and salts, edetic acid); coating agents (sodium carboxymethylcellulose, cellulose acetate, cellulose acetate phthalate, ethylcellulose, gelatin, pharmaceutical glaze, hydroxypropyl cellulose, hydroxypropyl methylcellulose, hydroxypropyl methylcellulose phthalate, methacrylic acid copolymer, methylcellulose, polyvinyl acetate phthalate, shellac, sucrose, titanium dioxide, carnauba wax, microcrystalline wax, zein); colorants (caramel, red, yellow, black or blends, ferric oxide); complexing agents (ethylenediaminetetraacetic acid and salts (EDTA), edetic acid, gentisic acid ethanolamide, oxyquinoline sulfate); desiccants (calcium chloride, calcium sulfate, silicon dioxide); emulsifying and/or solubilizing agents (acacia, cholesterol, diethanolamine (adjunct), glyceryl monostearate, lanolin alcohols, mono- and di-glycerides, monoethanolamine (adjunct), lecithin, oleic acid (adjunct), oleyl alcohol (stabilizer), poloxamer, polyoxyethylene 50 stearate, polyoxyl 35 castor oil, polyoxyl 40 hydrogenated castor oil, polyoxyl 10 oleyl ether, polyoxyl 20 cetostearyl ether, polyoxyl 40 stearate, polysorbate 20, polysorbate 40, polysorbate 60, polysorbate 80, diacetate, monostearate, sodium lauryl sulfate, sodium stearate, sorbitan monolaurate, sorbitan monooleate, sorbitan monopalmitate, sorbitan monostearate, stearic acid, trolamine, emulsifying wax); filtering aids (powdered cellulose, purified siliceous earth); flavors and perfumes (anethole, benzaldehyde, ethyl vanillin, menthol, methyl salicylate, monosodium glutamate, orange flower oil, peppermint, peppermint oil, peppermint spirit, rose oil, stronger rose water, thymol, tolu balsam tincture, vanilla, vanilla tincture, vanillin); humectants (glycerol, hexylene glycol, sorbitol); plasticizers (e.g., castor oil, diacetylated monoglycerides, diethyl phthalate, glycerol, mono- and di-acetylated monoglycerides, propylene glycol, triacetin, triethyl citrate); polymers (e.g., cellulose acetate, alkyl celluloses, hydroxyalkyl, acrylic polymers and copolymers); solvents (acetone, alcohol, diluted alcohol, amylene hydrate, benzyl benzoate, butyl alcohol, carbon tetrachloride, chloroform, corn oil, cottonseed oil, ethyl acetate, glycerol, hexylene glycol, isopropyl alcohol, methyl alcohol, methylene chloride, methyl isobutyl ketone, mineral oil, peanut oil, propylene carbonate, sesame oil, water for injection, sterile water for injection, sterile water for irrigation, purified water); Sorbents (powdered cellulose, charcoal, purified siliceous earth); carbon dioxide sorbents (barium hydroxide lime, soda lime); stiffening agents (hydrogenated castor oil, cetostearyl alcohol, cetyl alcohol, cetyl esters wax, hard fat, paraffin, polyethylene excipient, stearyl alcohol, emulsifying wax, white wax, yellow wax); Suspending and/or viscosity-increasing agents (acacia, agar, alginic acid, aluminum monostearate, bentonite, purified bentonite, magma bentonite, carbomer, carboxymethylcellulose calcium, carboxymethylcellulose sodium, carboxymethylcellulose sodium 12, carrageenan, microcrystalline and carboxymethylcellulose sodium cellulose, dextrin, gelatin, guar gum, hydroxyethyl cellulose, hydroxypropyl cellulose, hydroxypropyl methylcellulose, magnesium aluminum silicate, methylcellulose, pectin, polyethylene oxide, polyvinyl alcohol, povidone, alginate, silicon dioxide, colloidal silicon dioxide, sodium alginate, tragacanth, xanthum gum); sweetening agents (aspartame, dextrates, dextrose, excipient dextrose, fructose, mannitol, saccharin, calcium saccharin, sodium saccharin, sorbitol, solution sorbitol, sucrose, compressible sugar, confectioner's sugar, syrup); tablet binders (acacia, alginic acid, sodium carboxymethylcellulose, microcrystalline cellulose, dextrin, ethylcellulose, gelatin, liquid glucose, guar gum, hydroxypropyl methylcellulose, methylcellulose, polyethylene oxide, povidone, pregelatinized starch, syrup); tablet and/or capsule diluents (calcium carbonate, dibasic calcium phosphate, tribasic calcium phosphate, calcium sulfate, microcrystalline cellulose, powdered cellulose, dextrates, dextrin, dextrose excipient, fructose, kaolin, lactose, mannitol, sorbitol, starch, pregelatinized starch, sucrose, compressible sugar, confectioner's sugar); tablet disintegrants (alginic acid, microcrystalline cellulose, croscarmellose sodium, crospovidone, polacrilin potassium, sodium starch glycolate, starch, pregelatinized starch); Tablet and/or capsule lubricants (calcium stearate, glyceryl behenate, magnesium stearate, light mineral oil, sodium stearyl fumarate, stearic acid, purified stearic acid, talc, hydrogenated vegetable oil, zinc stearate); tonicity agent (dextrose, glycerol, mannitol, potassium chloride, sodium chloride); vehicle: flavored and/or sweetened (aromatic elixir, compound benzaldehyde elixir, iso-alcoholic elixir, peppermint water, sorbitol solution, syrup, tolu balsam syrup); vehicle: oleaginous (almond oil, corn oil, cottonseed oil, ethyl oleate, isopropyl myristate, isopropyl palmitate, mineral oil, light mineral oil, myristyl alcohol, octyldodecanol, olive oil, peanut oil, persic oil, sesame oil, soybean oil, squalane); vehicle: solid carrier (sugar spheres); vehicle: sterile (bacteriostatic water for injection, bacteriostatic sodium chloride injection); viscosity-increasing (see suspending agent); water repelling agent (cyclomethicone, dimethicone, simethicone); and/or solubilizing agent (benzalkonium chloride, benzethonium chloride, cetylpyridinium chloride, docusate sodium, nonoxynol 9, nonoxynol 10, octoxynol 9, poloxamer, polyoxyl 35 castor oil, polyoxyl 40, hydrogenated castor oil, polyoxyl 50 stearate, polyoxyl 10 oleyl ether, polyoxyl 20, cetostearyl ether, polyoxyl 40 stearate, polysorbate 20, polysorbate 40, polysorbate 60, polysorbate 80, sodium lauryl sulfate, sorbitan monolaurate, sorbitan monooleate, sorbitan monopalmitate, sorbitan monostearate, tyloxapol). This list is not meant to be exclusive, but instead merely representative of the classes of excipients and the particular excipients that may be used in oral dosage forms as described herein.

In one embodiment described herein, the compositions described herein comprise one or more active pharmaceutical ingredients. In one embodiment, one active pharmaceutical ingredient is the only active ingredient in the pharmaceutical composition. In another embodiment, one or more active pharmaceutical ingredients or drugs are included in the pharmaceutical composition. In another embodiment, one or more active pharmaceutical ingredients or drugs are included in a solid or semi-solid pharmaceutical composition comprising a soft lozenge.

In one embodiment, the compositions described herein comprise one or more active pharmaceutical ingredients useful for treating, retarding the progression of, delaying the onset of, prophylaxis of, amelioration of, or reducing the symptoms of esophagitis, eosinophilic esophagitis, esophageal inflammation, acid reflux, dysphagia, odynophagia, ulcers, heart burn, chest pain, abdominal pain, nausea, vomiting, coughing, sore throat, decrease in appetite or failure to thrive.

In one embodiment described herein, the active pharmaceutical ingredient comprises one or more corticosteroids. In one embodiment, the one or more corticosteroids include but are not limited to alclometasone, amcinonide, beclometasone, betamethasone, budesonide, ciclesonide, clobetasol, clobetasone, clocortolone, cloprednol, cortivazol, deflazacort, deoxycorticosterone, desonide desoximetasone, dexamethasone, diflorasone, diflucortolone, difluprednate, fluclorolone, fludrocortisone, fludroxycortide, flumetasone, flunisolide, fluocinolone acetonide, fluocinonide, fluocortin, fluocortolone, fluorometholone, fluperolone, fluticasone, fluticasone propionate, fluprednidene, formocortal, halcinonide, halometasone, hydrocortisone aceponate, hydrocortisone buteprate, hydrocortisone butyrate, loteprednol, medrysone, meprednisone, methylprednisolone, methylprednisolone aceponate, mometasone furoate, paramethasone, prednicarbate, prednisone, prednisolone, prednylidene, rimexolone, tixocortol, triamcinolone and ulobetasol, or combinations thereof, pharmaceutically acceptable salts or esters thereof.

In one embodiment described herein, the active pharmaceutical ingredient comprises one or more corticosteroid, including but not limited to, fluticasone, budesonide, prednisone, or combinations thereof. In another aspect, the active pharmaceutical ingredient comprises budesonide. In one aspect, the active pharmaceutical ingredient comprises fluticasone. In another aspect, the active pharmaceutical ingredient comprises fluticasone propionate.

In another embodiment, the active pharmaceutical ingredients described herein may comprise pharmaceutically acceptable salts of any of the above mentioned active drug substances. The term "pharmaceutically acceptable salts" of an active pharmaceutical ingredient includes alkali metal salts such as, for example, sodium or potassium salts, alkaline earth metal salts such as, for example, calcium and magnesium salts, and salts with organic or inorganic acid such as, for example, hydrochloric acid, hydrobromic acid, nitric acid, sulfuric acid, phosphoric acid, citric acid, formic acid, maleic acid, succinic acid, tartaric acid, methanesulphonic acid, toluenesulphonic acid etc. In another embodiment, the active pharmaceutical ingredient may also be in the form of pharmaceutically acceptable salts, uncharged or charged molecules, molecular complexes, solvates, or anhydrates thereof, and, if relevant, single isomers, enantiomers, racemic mixtures, or mixtures thereof.

In another embodiment, the active pharmaceutical ingredient may be in any of its crystalline, polymorphous, semicrystalline, amorphous or polyamorphous forms or mixtures thereof.

In one embodiment described herein, the pharmaceutical composition is a soft lozenge dosage form. The soft lozenge comprises a solid or semisolid matrix encapsulated by a gelatinous shell. In one embodiment described herein, the soft lozenge dosage form comprises about 0.5 mg or 1.0 mg of corticosteroid per dose. This comprises 0.016% or 0.032% by weight of a 3162.7 mg soft lozenge dosage form as described herein. Assuming an average body mass of 70 kg, the soft lozenge dosage forms provide a dose of 7.14 µg corticosteroid per kg body mass (µg/kg; 0.5 mg dose) or 14.3 µg/kg (1.0 mg dose).

In another embodiment described herein, the pharmaceutical composition is a liquid dosage form. The liquid dosage form can comprise a suspension, syrup, elixir, or concentrate. In one embodiment described herein the liquid dosage from comprises about 0.5 mg or 1.0 mg of corticosteroid per dose. A typical dose of a liquid dosage form comprises about 1 mL to about 20 mL of liquid, including all integers within the specified range.

The exact dosage will depend upon the route of administration, the form in which the composition is administered, the subject to be treated, the age, body weight/height of the subject to be treated, and the preference and experience of the attending physician. In certain embodiments, the optimal concentration of the corticosteroid in the composition depends upon the specific corticosteroid used, the characteristics of the patient, and the nature of the inflammation for which the treatment is sought. In various embodiments, these factors are determined by those of skill in the medical and pharmaceutical arts in view of the present disclosure.

In one embodiment described herein, the pharmaceutical composition comprises one or more corticosteroids comprising a therapeutically effective dose. A therapeutically effective dose comprises an amount of one or more corticosteroids that results in a degree of amelioration of symptoms or inflammation relative to the status of such symptoms or inflammation prior to treatment. In one embodiment, the amount of one or more corticosteroids used in a composition or in a method described herein is from about 7 µg/kg to about 70 µg/kg of body mass per day.

In one embodiment, the amount of corticosteroid used in a method, in a composition, or in a dose of a composition described herein comprises about 500 µg to about 2 mg, 500 µg to about 1 mg, about 1 mg to about 2 mg, about 1 mg, about 3 mg, about 1 mg to about 4 mg, about 1 mg to about 5 mg, or any amount suitable. In one embodiment, the dosage is provided in a volume that treats the esophagus with an effective amount. In one embodiment the effective amount is about 0.5 mg, about 1 mg, about 1.5 mg, or about 2 mg of a corticosteroid.

The dosage may, for example, be administered at least once a day, e.g., in five, four, three, two, or one dose a day. In one illustrative example, the dose is provided once a day. In specific embodiments, administration of any composition described herein (e.g., for the treatment of gastrointestinal or esophageal inflammation including eosinophilic esophagitis) is once a day. In other specific embodiments, administration (e.g., for the treatment of gastrointestinal or esophageal inflammation including eosinophilic esophagitis) is b.i.d. In still other embodiments, administration (e.g., for the treatment of gastrointestinal or esophageal inflammation including eosinophilic esophagitis) is t.i.d. In another embodiment, administration (e.g., for the treatment of gastrointestinal or esophageal inflammation including eosinophilic esophagitis) is q.i.d. In another embodiment, the dose is administered at night. In another aspect, the dose is administered about 30 minutes prior to bed, with no food or water given after administration of the compositions herein. In another embodiment, the dose is administered prior to bedtime, wherein after administration of the composition, the patient or individual is in a substantially supine position for at least 30 minutes, at least 1 hour, at least 2 hours, at least 4 hours, at least 8 hours, about 30 minutes to about 8 hours, about 30 minutes to about 4 hours, about 1 hour to about 8 hours, or, about 1 hour to about 6 hours. In some embodiments provided herein, the dose is administered prior to the individual being in a substantially supine position for at least 30 minutes, at least 1 hour, at least 2 hours, at least 4 hours, at least 8 hours, about 30 minutes to about 8 hours, about 30 minutes to about 4 hours, about 1 hour to about 8 hours, or, about 1 hour to about 6 hours. In specific embodiments, a corticosteroid or composition is administered according to any method described herein, wherein administration of the corticosteroid or composition is once a day, no more than once a day, more than once a day, twice a day, two to four times a day, three times a day, or four times a day. In some embodiments, the administration of the corticosteroid or composition provided herein is administered at night, e.g., not more than once a day at night.

In one embodiment described herein, the corticosteroid is present in a pharmaceutical composition described herein in any effective amount. In some embodiments, an effective amount is an amount sufficient to reduce inflammation or symptoms of inflammation associated with an allergic or caustic inflammatory disorder or condition of the gastrointestinal tract (e.g., the esophagus) as compared to the level of inflammation or symptoms of inflammation associated with an inflammatory disease prior to administration of the effective amount. In certain embodiments, effective amount is an amount sufficient to maintain a reduction in inflammation or symptoms of inflammation achieved in any manner including, but not limited to, by the administration of an effective amount sufficient to achieve such a reduction in inflammation.

In one embodiment, the effective amount is about 0.5 mg to about 5 mg, about 0.5 mg to about 1 mg, about 0.5 mg to about 2 mg, about 0.5 mg to about 3 mg; about 0.5 mg to about 4 mg; about 1 mg to about 5 mg, about 1 mg to about 2 mg, about 1 mg to about 3 mg, about 1 mg to about 4 mg, about 2 mg to about 3 mg, about 2 mg to about 4 mg, about 2 mg to about 5 mg, about 3 mg to about 4 mg, about 3 mg to about 5 mg, or about 4 mg to about 5 mg.

In another embodiment, the effective amount of corticosteroid is about 0.25 mg, about 0.5 mg, about 1 mg., about 1.5 mg., about 2 mg., about 2.5 mg., about 3 mg, about 3.5 mg, about 4 mg, about 4.5 mg, or about 5 mg, of corticosteroid.

In another embodiment, the corticosteroid is present in a pharmaceutical composition at any concentration suitable for providing a therapeutically effective amount of corticosteroid to a surface of the gastrointestinal tract (e.g., the surface of the esophagus), e.g., at a dosage of about 0.01 mg to about 2 mg of composition. In another embodiment, the corticosteroid is present in a pharmaceutical composition at a dose of about 0.5 mg to about 1 mg, about 0.5 mg to about 1.5 mg, about 0.5 mg to about 2 mg, about 0.5 mg to about 2.5 mg, about 0.5 mg to about 3 mg, about 0.5 mg to about 3.5 mg, about 0.5 to about 4 mg, about 0.5 to about 4.5 mg, or about 0.5 mg to about 5 mg. In another embodiment, the corticosteroid is present in a pharmaceutical composition at a dose of about 0.5 mg to about 1 mg. In another embodiment, any composition described herein comprises an amount or dose of corticosteroid sufficient to provide about 0.5 mg to about 5 mg of corticosteroid per day, about 0.5 mg to about 2 mg of corticosteroid per day, about 1 mg to about 2 mg of corticosteroid per day, about 2 mg to about 3 mg of corticosteroid per day, about 3 mg to about 4 mg of corticosteroid per day, about 4 mg to about 5 mg of corticosteroid per day, or about 5 mg of corticosteroid per day.

In another embodiment described herein, the therapeutically effective dose is about 2 mg of corticosteroid per day, administered b.i.d or q.i.d.

In another embodiment described herein, the dosage form can be administered, for example, 1×, 2×, 3×, 4×, 5×, 6×, 7×, or 8×, per day. One or more dosage form can be administered, for example, for 1, 2, 3, 4, 5, 6, 7 days, or even longer. One or more dosage forms can be administered, for example, for 1, 2, 3, 4 weeks, or even longer. One or more dosage forms can be administered, for example, for 1, 2, 3, 4, 5, 6, 7, 8, 9, 10, 11, 12 months, or even longer. One or more dosage forms can be administered until the patient, subject, mammal, mammal in need thereof, human, or human in need thereof, does not require treatment, prophylaxis, or amelioration of any disease or condition such as, for example, inflammation or pain. In some aspects, the dosage form may be co-administered with other pharmaceutical compositions until the patient, subject, mammal, mammal in need thereof, human, or human in need thereof, does not require treatment, prophylaxis, or amelioration of any disease or condition including but not limited to inflammation or pain.

In another embodiment described herein, the dosage form dissolves intra-orally over a period of time comprising about 30 seconds to about 2 minutes, about 1 minute to about 5 minutes, about 5 minutes to about 10 minutes, about 10 minutes to about 15 minutes, about 10 minutes to about 20 minutes, about 15 minutes to about 20 minutes, about 20 minutes to about 30 minutes, about 20 minutes to about 45 minutes, about 30 minutes to about 45 minutes, about 30 minutes to about 1 hour, about 45 minutes to about 60 minutes, about 45 minutes to about 75 minutes, about 60 minutes to about 75 minutes, or about 60 minutes to about 90 minutes.

In another embodiment described herein, the dosage form dissolves in vitro in aqueous media at neutral pH over a period of time comprising about 30 seconds to about 2 minutes, about 1 minute to about 5 minutes, about 5 minutes to about 10 minutes, about 10 minutes to about 15 minutes, about 10 minutes to about 20 minutes, about 15 minutes to about 20 minutes, about 20 minutes to about 30 minutes, about 20 minutes to about 45 minutes, about 30 minutes to about 45 minutes, about 30 minutes to about 1 hour, about 45 minutes to about 60 minutes, about 45 minutes to about 75 minutes, about 60 minutes to about 75 minutes, or about 60 minutes to about 90 minutes.

In another embodiment, the dosage form has an in vitro dissolution rate in a neutral aqueous media (e.g., pH 7.4) of about 5% to about 50% after about 2 minutes to about 40 minutes, including each integer within the specified ranges of dissolution and time. In one aspect, the in vitro dissolution rate in a neutral aqueous media (e.g., pH 7.4) is about 50% after about 2 minutes. In one aspect, the in vitro dissolution rate in a neutral aqueous media (e.g., pH 7.4) is about 50% after about 2.5 minutes. In one aspect, the in vitro dissolution rate in a neutral aqueous media (e.g., pH 7.4) is about 50% after about 5 minutes. In one aspect, the in vitro dissolution rate in a neutral aqueous media (e.g., pH 7.4) is about 50% after about 7.5 minutes. In one aspect, the in vitro dissolution rate in a neutral aqueous media (e.g., pH 7.4) is about 50% after about 10 minutes. In one aspect, the in vitro dissolution rate in a neutral aqueous media (e.g., pH 7.4) is about 50% after about 12.5 minutes. In one aspect, the in vitro dissolution rate in a neutral aqueous media (e.g., pH 7.4) is about 50% after about 15 minutes. In one aspect, the in vitro dissolution rate in a neutral aqueous media (e.g., pH 7.4) is about 50% after about 20 minutes. In one aspect, the in vitro dissolution rate in a neutral aqueous media (e.g., pH 7.4) is about 50% after about 25 minutes. In one aspect, the in vitro dissolution rate in a neutral aqueous media (e.g., pH 7.4) is about 50% after about 30 minutes.

In another embodiment described herein, the dosage form releases the active ingredient over a period of time comprising about 30 seconds to about 2 minutes, about 1 minute to about 5 minutes, about 5 minutes to about 10 minutes, about 10 minutes to about 15 minutes, about 10 minutes to about 20 minutes, about 15 minutes to about 20 minutes, about 20 minutes to about 30 minutes, about 20 minutes to about 45 minutes, about 30 minutes to about 45 minutes, about 30 minutes to about 1 hour, about 45 minutes to about 60 minutes, about 45 minutes to about 75 minutes, about 60 minutes to about 75 minutes, or about 60 minutes to about 90 minutes.

In another embodiment described herein, the dosage form is in contact with the oral and esophageal mucosa for a period of time comprising about 30 seconds to about 45 minutes, including all integers within the specified range. In one aspect, the dosage form is in contact with the oral and esophageal mucosa for a period of time comprising about 30 seconds, about 1 minutes, about 2 minutes, about 3 minutes, about 4 minutes, about 5 minutes, about 6 minutes, about 7 minutes, about 8 minutes, about 9 minutes, about 10 minutes, about 11 minutes, about 12 minutes, about 15 minutes, about 20 minutes, about 25 minutes, about 30 minutes, about 35 minutes, about 40 minutes, about 45 minutes, about 50 minutes, about 55 minutes, about 60 minutes, about 65 minutes, about 70 minutes, about 75 minutes, about 80 minutes, about 85 minutes, about 90 minutes, or even longer.

In another embodiment described herein, the dosage form is in contact with the oral and esophageal mucosa for a period of time comprising at least about 30 seconds to about 45 minutes, including all integers within the specified range. In one aspect, the dosage form is in contact with the oral and esophageal mucosa for a period of time comprising at least about 30 seconds, about 1 minutes, about 2 minutes, about 3 minutes, about 4 minutes, about 5 minutes, about 6 minutes, about 7 minutes, about 8 minutes, about 9 minutes, about 10 minutes, about 11 minutes, about 12 minutes, about 15 minutes, about 20 minutes, about 25 minutes, about 30 minutes, about 35 minutes, about 40 minutes, about 45 minutes, about 50 minutes, about 55 minutes, about 60 minutes, about 65 minutes, about 70 minutes, about 75 minutes, about 80 minutes, about 85 minutes, about 90 minutes, or even longer.

In another embodiment described herein, the dosage form is in contact with the oral and esophageal mucosa for a period of time comprising about 30 seconds to about 90 minutes including all integers within the specified range. In one aspect, the dosage form is in contact with the oral and esophageal mucosa for a period of time comprising about 30 seconds to about 2 minutes, about 1 minute to about 5 minutes, about 1 minutes to about 10 minutes, about 1 minute to about 15 minutes, about 1 minute to about 20 minutes, about 1 minute to about 20 minutes, about 1 minute to about 30 minutes, about 1 minute to about 45 minutes, about 1 minute to about 1 hour, about 1 minute to about 75 minutes, or about 1 minute to about 90 minutes.

In another embodiment described herein, the dosage form is in contact with the oral and esophageal mucosa for a period of time comprising at least about 30 seconds to about 90 minutes including all integers within the specified range. In one aspect, the dosage form is in contact with the oral and esophageal mucosa for a period of time comprising at least about 30 seconds to about 2 minutes, about 1 minute to about 5 minutes, about 5 minutes to about 10 minutes, about 10 minutes to about 15 minutes, about 10 minutes to about 20 minutes, about 15 minutes to about 20 minutes, about 20 minutes to about 30 minutes, about 20 minutes to about 45 minutes, about 30 minutes to about 45 minutes, about 30 minutes to about 1 hour, about 45 minutes to about 60 minutes, about 45 minutes to about 75 minutes, about 60 minutes to about 75 minutes, or about 60 minutes to about 90 minutes.

Another embodiment described herein is a topical, non-systemic, slow-release oral pharmaceutical composition suitable for chewing, sucking, buccal dissolution or swallowing as described herein for treating, retarding the progression of, prophylaxis of, delaying the onset of, ameliorating, reducing the symptoms of, or promoting health, including but not limited to of one or more of esophageal, oral, or buccal inflammation, eosinophilic esophagitis, oral lichen planus, aphthous stomatitis, odynophagia, acid reflux, dysphagia, oral, esophageal or peptic ulcers, heart burn, chest pain, abdominal pain, nausea, vomiting, coughing, sore throat, decrease in appetite, or failure to thrive.

Another embodiment described herein is a method for treating, retarding the progression of, prophylaxis of, delaying the onset of, ameliorating, reducing the symptoms of, or promoting health of one or more of esophageal, oral, or buccal inflammation, eosinophilic esophagitis, oral lichen planus, aphthous stomatitis, odynophagia, acid reflux, dysphagia, oral, esophageal or peptic ulcers, heart burn, chest pain, abdominal pain, nausea, vomiting, coughing, sore throat, decrease in appetite, or failure to thrive, comprising administering to a subject in need thereof an oral pharmaceutical composition suitable for chewing, sucking, or buccal dissolution as described herein.

Another embodiment described herein is a topical, non-systemic, slow-release pharmaceutical composition suitable for chewing, sucking, buccal dissolution or swallowing as described herein for treating a subject suffering from one or more of oral or esophageal inflammation, eosinophilic esophagitis, inflammatory bowel disease involving the esophagus, oral lichen planus, aphthous stomatitis, Crohn's disease, esophageal inflammation secondary to caustic/irritant ingestion, recurrent esophageal strictures of any cause and including irritant ingestion, pill-induced esophagitis, systemic diseases, congenital diseases, epidermolysis bullosa, trauma, or post-surgery inflammation.

Another embodiment described herein is a method for treating a subject suffering from oral or esophageal inflammation, eosinophilic esophagitis, inflammatory bowel disease involving the esophagus, oral lichen planus, aphthous stomatitis, Crohn's disease, esophageal inflammation secondary to caustic/irritant ingestion, recurrent esophageal strictures of any cause and including irritant ingestion, pill-induced esophagitis, systemic diseases, congenital diseases, epidermolysis bullosa, trauma, or post-surgery inflammation, including comprising administering to the subject in need thereof an topical, non-systemic, slow-releasing oral pharmaceutical composition suitable for chewing, sucking, buccal dissolution, or swallowing as described herein.

Another embodiment described herein is a topical, non-systemic, slow-releasing oral pharmaceutical composition suitable for chewing, sucking, buccal dissolution, or swallowing as described herein for treating disease, allergic, idiopathic, immunogenic, traumatic, caustic or general inflammation of the oral cavity, esophagus, or upper gastrointestinal tract, or a symptom thereof comprising about 0.5 mg to about 5 mg of corticosteroid, about 0.5 mg to about 1 mg of corticosteroid, about 1 mg to about 2 mg of corticosteroid, about 2 mg to about 3 mg of corticosteroid, about 3 mg to about 4 mg of corticosteroid, or about 4 mg to about 5 mg of corticosteroid.

Another embodiment described herein is a method for treating disease, allergic, idiopathic, immunogenic, traumatic, caustic or general inflammation of the oral cavity, esophagus, or upper gastrointestinal tract, or a symptom thereof, by administering a sufficient amount of a pharmaceutical composition suitable for chewing, sucking, or buccal dissolution as described herein to provide about 0.5 mg to about 5 mg of corticosteroid per day, about 0.5 mg to about 1 mg of corticosteroid per day, about 1 mg to about 2 mg of corticosteroid per day, about 2 mg to about 3 mg of corticosteroid per day, about 3 mg to about 4 mg of corticosteroid per day, or about 4 mg to about 5 mg of corticosteroid per day to an individual in need thereof.

Initial treatment may continue, for example, for about 3 days to 2 weeks for an acute condition, or about 4 weeks to about 16 weeks for a chronic condition, or about 8 weeks to about 12 weeks for a chronic condition. Longer therapy may also be needed, such as, for example, therapy similar to chronic therapy for persistent asthma. Patients may, for example, be treated for up to 6 months, or up to one year. Maintenance treatment can last up to or longer than one year. Patients may be treated on a maintenance basis or on an as needed basis during a problematic episode, depending on the severity of the condition. Patients can also be treated on a rotating treatment basis, where treatment is provided for a period of time and then the patient is taken off of the drug for a period before treatment resumes again. When off the drug, the patient may be given no treatment, treatment with another medication, or treatment with a reduced dosage. Patients may be given treatment with a higher dose of the composition until a desired reduced disease state is achieved, and then continued on a lower dose of the composition.

Another embodiment described herein comprises administering one or more of the pharmaceutical compositions or dosage forms described herein in combination with one or more additional active pharmaceutical ingredients. Such combinations may be formulated into a single dosage form or alternatively co-administered as separate dosage forms in a treatment regimen. Co-administration may be simultaneously or at a different time. Suitable combinations include administering one or more corticosteroids as described herein with one or more antacids, synthetic corticosteroids, proton pump inhibitors (e.g., $H_1$ and $H_2$ antagonists), $\beta_2$ adrenergic receptor agonists, anticholinergic bronchodilators, antihistamines, leukotriene receptor antagonists, interleukin-5 antibodies, anti-IgE antibodies, anti-TNF antibodies, purine analogues, non-steroidal anti-inflammatory drugs (NSAIDS), one or more antibiotics, or combinations thereof. In one embodiment the pharmaceutical compositions described herein can be combined with one or more of antacids (e.g., calcium hydroxide, magnesium hydroxide, alluminum hydroxide, sodium bicarbonate, calcium carbonate, bismuth subsalicylate, or others; Maalox, Mylanta, Gaviscon, Kaopectate, Pepto-Bismol) sucralfate, esomeprazole, omeprazole, lansoprazole, dexlansoprazole, esomeprazole, pantoprazole, rabeprazole, ilaprazole, cimetidine, ranitidine, famotidine, lafutidine, nizatidine, roxatidine, tiotidine, salmeterol, albuterol, aclidinium, ipratropium, tiotropium, umeclidinium, acrivastine, azelastine, bilastine, brompheniramine, buclizine, bromodiphenhydramine, carbinoxamine, chlorpromazine, cyclizine, chlorphenamine, chlorodiphenhydramine, clemastine, cyproheptadine, dexbrompheniramine, dexchlorpheniramine, dimenhydrinate, dimetindene, diphenhydramine, doxylamine, ebastine, embramine, fexofenadine, hydroxyzine, loratadine, meclozine, mirtazapine, olopatadine, orphenadrine, phenindamine pheniramine, phenyltoloxamine, promethazine, quetiapine, rupatadine, triprolennamine, triprolidine, clobenpropit, ciproxifan, conessine, thioperamide, montelukast, zafirlukast, pranlukast, mepolizumab, reslizumab, omalizumab, infliximab, azathioprine, 6-mercaptopurine, thioguanine, aspirin (acetylsalicylic acid), ibuprofen, naproxen, ketoprofen, celecoxib, diclofenac, amikacin, gentamicin, kanamycin, neomycin, netilmicin, tobramycin, paromomycin, streptomycin, spectinomycin, geldanamycin, herbimycin, rifaximin, loracarbef, ertapenem, doripenem, imipenem/cilastatin, meropenem, cefadroxil, cefazolin, cefalotin, cefalexin, cefaclor, cefamandole, cefoxitin, cefprozil, cefuroxime, cefixime, cefdinir, cefditoren, cefoperazone, cefotaxime, cefpodoxime, ceftazidime, ceftibuten, ceftizoxime, ceftriaxone, cefepime, ceftaroline fosamil, ceftobiprole, teicoplanin, vancomycin, televancin, dalbavancin, oritavancin, clindamycin, lincomycin, daptomycin, azithromycin, clarithromycin, dirithromycin, erythromycin, roxithromycin, troleandomycin, telithromycin, spiramycin, aztreonam, furazolidone, nitrofurantoin, linezolid, posizolid, radezolid, torezolid, amoxicillin, ampicillin, azlocillin, carbenicillin, cloxacillin, dicloxacillin, flucloxacillin, mezlocillin, methicillin, nafcillin, oxacillin, penicillin G, penicillin V, piperacillin, temocillin, ticarcillin, amoxicillin/clavulanate, ampicillin/sulbactam, piperacillin/tazobactam, ticarcillin/clavulanate, bacitracin, colistin, polymyxin B, ciprofloxacin, enoxacin, gatifloxacin, gemifloxacin, levofloxacin, lomefloxacin, moxifloxacin, nalidixic acid, norfloxacin, ofloxacin, trovafloxacin, grepafloxacin, sparfloxacin, temafloxacin, mafenide, sulfacetamide, sulfadiazine, silver sulfadiazine, sulfadimethoxine, sulfamethizole, sulfamethoxazole, solfanilamide, sulfasalazine, sulfisoxazole, trimethoprim-sulfamethoxazole, sulfamidochrysoidine, demeclocycline, doxycycline, minocycline, oxytetracycline, tetracycline, clofazimine, dapsone, capreomycin, cycloserine, ethambutol, ethionamide, isoniazid, pyrazinamide, rifampicin, rifabutin, rifapentine, streptomycin, arsphenamine, chloramphenicol, fosfomycin, fusidic acid, metronidazole, mupirocin, platensimycin, quinupristin/dalfopristin, thiamphenicol, tigecycline, tinidazole, trimethoprim, or combinations thereof.

In another embodiment, the pharmaceutical compositions described herein can be administered in combination with elimination or elemental diets. In one embodiment, the subject eliminates milk products, eggs, wheat, soy, peanut/tree nuts, and fish/shellfish from the diet for at least 6 weeks. In another embodiment, foods are re-introduced while monitoring symptoms. Foods most frequently associated with eosinophilic esophagitis in adults were wheat and milk. Gonsalves et al., *Gastroenterology* 142(7):1451-1459 (2012), incorporated herein by reference for the specific teachings thereof. Elemental diets comprising monomeric food elements, including amino acids, fats, sugars, vitamins, and minerals, can also be used in combination with the pharmaceutical compositions described herein. Such elemental diets can reduce the symptoms of eosinophilic esophagitis. Vashi and Hirano, *Curr. Opin. Gastroenterol.* 29(4):407-415 (2013), incorporated herein by reference for the specific teachings thereof.

In another embodiment, the pharmaceutical composition may contain one or more active pharmaceutical ingredients. For example, the pharmaceutical composition may contain one or more corticosteroids and one or more topical anesthetics such as lidocaine, prilocaine, or a eutectic mixture of idocaine/prilocaine, at a concentration of about 2% to about 5% of anesthetic by weight of the total pharmaceutical composition. Such pharmaceutical compositions may be used for treating pain associated with oral or esophageal inflammation, including but not limited to infection, trauma, post-surgical inflammation, oral lichen planus, or other painful inflammatory condition or disorder.

Another embodiment described herein is a process of manufacturing pharmaceutical compositions comprising the soft lozenges as described herein. The process includes preparing the matrix fill composition is prepared by combining gelatin, glycerol, and water and maintaining the mixture and adding maltitol syrup to create a fill gel solution; separately, combining water, xylitol, sucralose, and citric acid together to create a fill sweetener solution; separately, combining the active pharmaceutical ingredient (API) and polysorbate 80; combining the API and polysorbate 80 with the fill sweetener solution to create an API solution; combining the API solution and the fill gel solution; further mixing the combined API and fill gel solution at least about 65° C.; slowly introducing solid polyethylene oxide into the combined API and fill gel solution and mixing and deaerating at least about 65° C. creating a matrix fill composition. The gel mass is prepared by combining gelatins, glycerol, and water and maintaining the mixture at least about 65° C.; adding maltitol syrup to create a shell gel solution; separately, combining water, xylitol, sucralose, and citric acid together to create a shell sweetener solution; combining the shell sweetener solution and shell gel solution and mixing the combined shell sweetener and shell gel solution at least about 65° C. to create a gel mass. The soft lozenge is prepared by casting the gel mass into shell films or ribbons using heat-controlled drums or surfaces; and injecting the matrix fill solution between the shell ribbons, and creating soft lozenges using rotary die technology. Rotary die encapsulation may be performed using an apparatus as described in U.S. Pat. Nos. 5,459,983; 5,146,730; and 6,482,516, each of which are incorporated by reference herein for such teachings.

Another embodiment described herein includes a process of manufacturing soft lozenges comprising the pharmaceutical compositions as described herein. The process includes preparing a gel mass composition comprising one or more polymers, one or more plasticizers, one or more pH modifiers, one or more solvents, one or more active pharmaceutical ingredients, and appropriate flavorings, sweeteners, coloring agents, or other excipients; casting the gel mass into films or ribbons using heat-controlled drums or surfaces; and manufacturing a soft capsule comprising a matrix fill using rotary die technology. The thickness of the films or ribbons that form the soft lozenge is from about 0.010 inches (≈0.254 mm) to about 0.050 inches (≈1.27 mm), including all integers within the specified range. The shell thickness can be about 0.010 inch (≈0.254 mm), about 0.015 inch (≈0.381 mm), about 0.02 in (≈0.508 mm), about 0.03 in (≈0.762 mm), about 0.04 in (≈1.02 mm), or about 0.05 in (≈1.27 mm). In one embodiment, the thickness is about 0.02 inches (≈0.508 mm) to about 0.040 inches (≈1.02 mm). In one embodiment, the shell thickness is about 0.028 inches (≈0.711 mm). In another embodiment, the shell thickness is about 0.033 inches (≈0.838 mm). In another embodiment, the shell thickness is about 0.038 inches (≈0.956 mm). In some embodiments, the fill of the soft lozenge can comprise the same components of the "shell" and can be injected into the "shell" to form a uniform soft lozenge. In other embodiments, the shell can have a different formulation as compare to the fill.

In another embodiment described herein, the soft lozenge comprises an outer dimension from about 2 oval to about 30 oval including all iterations of typical soft capsule sizes within the specified range (e.g., 2 oval, 3 oval, 4 oval, 5 oval, 6 oval, 7 oval, 8 oval, 10 oval, 12 oval, 16 oval, 20, or 30 oval). In another embodiment described herein, the soft lozenge comprises an outer dimension from about 2 round to about 28 round including all iterations of capsule size within the specified range (e.g., 2 round, 3 round, 4 round, 5 round, 6 round, 7 round, 8 round, 10 round, 12 round, 16 round, 20 round, or 28 round). In another embodiment described herein, the soft lozenge comprises an outer dimension from about 2 oblong to about 22 oblong including all iterations of capsule size within the specified range (e.g., 2 oblong, 3 oblong, 4 oblong, 5 oblong, 6 oblong, 7 oblong, 8 oblong, 10 oblong, 11, oblong, 12 oblong, 14 oblong, 16 oblong, 20 oblong, or 22 oblong). See *Remington's Essentials of Pharmaceutics*, Pharmaceutical Press Publishing Company, London, UK, 1$^{st}$ Edition, 2013, which is incorporated by reference herein for such teachings.

In another embodiment, the pharmaceutical composition described herein is contained and dispensed from a tamper evident packaging. The term "tamper evident" or "tamper resistant" refers to a packaging of any kind that readily displays or allows an individual to observe any physical interference or manipulation of said packaging. The tamper evident packaging provides reasonable evidence to consumers that tampering has occurred. The tamper evident packaging additionally contains appropriate labelling statements describing the features and evidences of the tamper evident packaging. In one aspect, the tamper evident packaging comprises: bottles, film wrappers, blister or strip packs, bubble packs, heat shrink bands or wrappers, foil, paper, or plastic pouches, container mouth inner seals, tape seals, breakable caps, sealed metal tubes or plastic heat-sealed tubes, sealed cartons, aerosol containers, cans including metal and composite materials, or any combination thereof. The packaging may also contain instructions for prescribing, instructions for use, warnings, or other appropriate information.

It will be apparent to one of ordinary skill in the relevant art that suitable modifications and adaptations to the compositions, formulations, methods, processes, and applications described herein can be made without departing from the scope of any embodiments or aspects thereof. The compositions and methods provided are exemplary and are not intended to limit the scope of any of the specified embodiments. All of the various embodiments, aspects, and options disclosed herein can be combined in any and all variations or iterations. The scope of the compositions, formulations, methods, and processes described herein include all actual or potential combinations of embodiments, aspects, options, examples, and preferences herein described. The exemplary compositions and formulations described herein may omit any component, substitute any component disclosed herein, or include any component disclosed elsewhere herein. The ratios of the mass of any component of any of the compositions or formulations disclosed herein to the mass of any other component in the formulation or to the total mass of the other components in the formulation are hereby disclosed as if they were expressly disclosed. Should the meaning of any terms in any of the patents or publications incorporated by reference conflict with the meaning of the terms used in this disclosure, the meanings of the terms in this disclosure are controlling. Furthermore, the foregoing discloses and describes exemplary embodiments. All patents and publications cited herein are incorporated by reference herein for the specific teachings thereof.

EXAMPLES

Example 1

Soft Lozenge Compositions

Exemplary soft lozenges were prepared by rotary die encapsulation using the respective fill and shell compositions shown in Tables 7-8. The weight of the fill is 2000 mg and the shell is 1162.7 mg. The total weight of the soft lozenge is 3162.7 mg. After drying, the final mass of the soft lozenge is about 2800 mg. About 300-400 mg of water is evaporated during drying (~9-10% water lost).

TABLE 7

Exemplary Soft Lozenge Fill Composition

| Ingredient | Mass (mg) | Weight Percent (%) |
|---|---|---|
| Gelatin, 150 Bloom | 150 | 7.5 |
| Glycerol | 150 | 7.5 |
| Citric Acid | 20 | 1 |
| Mannitol Syrup | 1154 | 57.7 |
| Xylitol (Xylisorb 300 ®) | 85 | 4.3 |

TABLE 7-continued

Exemplary Soft Lozenge Fill Composition

| Ingredient | Mass (mg) | Weight Percent (%) |
|---|---|---|
| Sucralose | 6 | 0.3 |
| Water | 433 | 21.7 |
| Fluticasone | 1.8 | 0.1 |
| TOTAL | 2000 | 100% |

TABLE 8

Exemplary Soft Lozenge Shell Composition

| Ingredient | Mass (mg) | Weight Percent (%) |
|---|---|---|
| Gelatin, 150 Bloom | 219.9 | 18.9 |
| Gelatin, 100 Bloom | 149.9 | 12.9 |
| Gelatin Hydrolysate | 27.7 | 2.4 |
| Glycerol | 264.6 | 22.8 |
| Citric Acid, Anhydrous | 6.3 | 0.5 |
| Maltitol (75% solution; e.g., Lycasin ® 80/55) | 163.7 | 14.1 |
| Xylitol (e.g., Xylisorb 300 ®) | 29.1 | 2.5 |
| Sucralose | 2.4 | 0.2 |
| Water | 286.6 | 24.6 |
| Titanium Dioxide | 12.5 | 1.1 |
| TOTAL | 1162.7 | 100% |

Example 2

Based on the results of solubility and bioavailability testing of the Example 1 formulation (data not shown), a second formulation was developed that included a solubilizing agent comprising polysorbate 80 and release modifier comprising a high molecular weight polyethylene oxide to further solubilize and control the release of the active pharmaceutical ingredient. Batches of soft lozenges were prepared by rotary die encapsulation using the fill and shell compositions shown in Tables 9-10. The total weight of the soft lozenge was 3162.7 mg. After drying, the final mass of the soft lozenge was about 2800 mg. About 300-400 mg of water is evaporated during drying (~9-10% water lost).

TABLE 9

Exemplary Soft Lozenge Fill Composition

| Ingredient | Mass (mg) | Weight Percent (%) |
|---|---|---|
| Gelatin, 150 Bloom | 150 | 7.5 |
| Glycerol | 150 | 7.5 |
| Polyethylene Oxide, 7,000,000 MW, (e.g., Polyox ® WSR-303) | 60 | 3 |
| Citric Acid | 20 | 1 |
| Mannitol Syrup | 1154 | 57.7 |
| Xylitol (e.g., Xylisorb 300 ®) | 85 | 4.3 |
| Sucralose | 6 | 0.3 |
| Polysorbate 80 (e.g., Tween ® 80) | 14 | 0.7 |
| Water | 360 | 18 |
| Fluticasone propionate | 1.8 | 0.1 |
| TOTAL | 2000 | 100% |

TABLE 10

Exemplary Soft Lozenge Shell Composition

| Ingredient | Mass (mg) | Weight Percent (%) |
|---|---|---|
| Gelatin, 150 Bloom | 219.9 | 18.9 |
| Gelatin, 100 Bloom | 149.9 | 12.9 |
| Gelatin Hydrolysate | 27.7 | 2.4 |
| Glycerol | 264.6 | 22.8 |
| Citric Acid, Anhydrous | 6.3 | 0.5 |
| Maltitol (75% solution; e.g., Lycasin ® 80/55) | 163.7 | 14.1 |
| Xylitol (e.g., Xylisorb 300 ®) | 29.1 | 2.5 |
| Sucralose | 2.4 | 0.2 |
| Water | 286.6 | 24.6 |
| Titanium Dioxide | 12.5 | 1.1 |
| TOTAL | 1162.7 | 100% |

Example 3

Exemplary soft lozenges can be prepared by rotary die encapsulation using the compositions shown in Tables 11-12. The weight of the fill is 2000 mg and the shell is 1162.7 mg. The total weight of the soft lozenge is 3162.7 mg. After drying, the final mass of the soft lozenge is about 2800 mg. About 300-400 mg of water is evaporated during drying (~9-10% water lost).

TABLE 11

Exemplary Soft Lozenge Fill Compositions

| Ingredient | Weight Percent (%) | | | | | | | |
|---|---|---|---|---|---|---|---|---|
| | EX1 | EX2 | EX3 | EX4 | EX5 | EX6 | EX7 | EX8 |
| Gelatin, 150 Bloom | 7.0 | 10.0 | 9.0 | 8.0 | 9.0 | 10.0 | 4.5 | 11.0 |
| Polyethylene Oxide, 7,000,000 MW, (e.g., Polyox ® WSR-303) | 1.0 | 5.0 | 2.8 | 3.0 | 4.1 | 4.0 | 4.3 | 5.0 |
| Glycerol | 11.0 | 10.0 | 9.0 | 8.0 | 7.0 | 6.0 | 5.0 | 4.0 |
| Citric Acid | 5.0 | 4.3 | 3.5 | 3.0 | 2.0 | 1.5 | 1.0 | 0.5 |
| Maltitol (75% solution; e.g., Lycasin ® 80/55) | 34.7 | 24.7 | 45.3 | 54.0 | 58.2 | 60.9 | 70.2 | 66.3 |
| Xylitol (e.g., Xylisorb 300 ®) | 10.0 | 9.0 | 6.0 | 5.5 | 4.8 | 3.5 | 2.0 | 1.0 |
| Sucralose | 0.1 | 2.0 | 0.6 | 1.0 | 1.5 | 1.8 | 1.8 | 2.1 |
| Polysorbate 80 (e.g., Tween ® 80) | 1.2 | 1.0 | 0.8 | 0.5 | 0.4 | 0.3 | 0.3 | 0.1 |
| Water | 30.0 | 34.0 | 23.0 | 17.0 | 13.0 | 12.0 | 11.0 | 10.0 |
| Fluticasone propionate | 0.03 | 0.05 | 0.08 | 0.01 | 0.10 | 0.05 | 0.04 | 0.03 |
| TOTAL | 100.0 | 100.0 | 100.0 | 100.0 | 100.0 | 100.0 | 100.0 | 100.0 |

TABLE 11-continued

Exemplary Soft Lozenge Fill Compositions

| Ingredient | Weight Percent (%) | | | | | | | |
|---|---|---|---|---|---|---|---|---|
| | EX1 | EX2 | EX3 | EX4 | EX5 | EX6 | EX7 | EX8 |
| Subcomponent Totals | | | | | | | | |
| Film-forming Polymer | 7.0 | 10.0 | 9.0 | 8.0 | 9.0 | 10.0 | 4.5 | 11.0 |
| Release Modifier | 1.0 | 5.0 | 2.8 | 3.0 | 4.1 | 4.0 | 4.3 | 5.0 |
| Plasticizer | 11.0 | 10.0 | 9.0 | 8.0 | 7.0 | 6.0 | 5.0 | 4.0 |
| pH Modifier | 5.0 | 4.3 | 3.5 | 3.0 | 2.0 | 1.5 | 1.0 | 0.5 |
| Sweetener | 44.8 | 35.7 | 51.9 | 60.5 | 64.4 | 66.2 | 74.0 | 69.4 |
| Solubilizing Agent | 1.2 | 1.0 | 0.8 | 0.5 | 0.4 | 0.3 | 0.3 | 0.1 |
| Solvent | 30.0 | 34.0 | 23.0 | 17.0 | 13.0 | 12.0 | 11.0 | 10.0 |
| API | 0.0 | 0.1 | 0.1 | 0.0 | 0.1 | 0.1 | 0.0 | 0.0 |
| Relational Ratios | | | | | | | | |
| API:Total Fill Composition | $2.5E^{-4}$ | $5.0E^{-4}$ | $7.5E^{-4}$ | $1.0E^{-4}$ | $1.0E^{-4}$ | $5.0E^{-4}$ | $4.0E^{-4}$ | $2.5E^{-4}$ |
| PEO:Gelatin | 0.14 | 0.50 | 0.31 | 0.38 | 0.46 | 0.40 | 0.94 | 0.45 |
| PEO:Plasticizer | 0.09 | 0.50 | 0.31 | 0.38 | 0.59 | 0.67 | 0.85 | 1.25 |

TABLE 12

Exemplary Soft Lozenge Shell Compositions

| Ingredient | Weight Percent (%) | | | | | | | |
|---|---|---|---|---|---|---|---|---|
| | EX1 | EX2 | EX3 | EX4 | EX5 | EX6 | EX7 | EX8 |
| Gelatin, 150 Bloom | 20.0 | 20.0 | 19.0 | 17.0 | 15.0 | 12.0 | 11.0 | 10.0 |
| Gelatin, 100 Bloom | 10.0 | 12.0 | 14.0 | 12.0 | 14.0 | 14.0 | 17.0 | 10.0 |
| Gelatin hydrolysate | 0.5 | 0.5 | 1.0 | 2.0 | 3.0 | 4.0 | 5.0 | 5.0 |
| Glycerol | 10.0 | 12.0 | 15.0 | 17.0 | 22.0 | 25.0 | 27.0 | 30.0 |
| Maltitol (75% solution; e.g., Lycasin ® 80/55) | 5.0 | 4.5 | 4.0 | 3.0 | 2.5 | 1.0 | 0.8 | 0.1 |
| Citric Acid | 5.0 | 10.0 | 9.2 | 14.5 | 12.7 | 18.9 | 19.3 | 20.3 |
| Xylitol | 10.0 | 9.0 | 7.0 | 5.0 | 3.0 | 1.0 | 1.5 | 8.0 |
| Sucralose | 2.5 | 2.0 | 1.8 | 1.5 | 1.0 | 0.1 | 0.4 | 0.1 |
| Water | 35.0 | 29.0 | 27.0 | 26.0 | 24.0 | 22.0 | 15.0 | 12.0 |
| Titanium dioxide | 0.0 | 0.0 | 0.1 | 0.5 | 0.8 | 1.0 | 1.5 | 2.5 |
| Coloring (FD&C dyes) | 0.020 | 0.010 | 0.015 | 0.020 | 0.020 | 0.010 | 0.015 | 0.020 |
| Flavoring (e.g., cherry, orange) | 2.0 | 1.0 | 2.0 | 1.5 | 2.0 | 1.0 | 1.5 | 2.0 |
| TOTAL | 100.0 | 100.0 | 100.0 | 100.0 | 100.0 | 100.0 | 100.0 | 100.0 |
| Subcomponent Totals | | | | | | | | |
| Film-forming Polymers | 30.5 | 32.5 | 34.0 | 31.0 | 32.0 | 30.0 | 33.0 | 25.0 |
| Plasticizer | 10.0 | 12.0 | 15.0 | 17.0 | 22.0 | 25.0 | 27.0 | 30.0 |
| pH Modifier | 5.0 | 4.5 | 4.0 | 3.0 | 2.5 | 1.0 | 0.8 | 0.1 |
| Total Sweetener | 17.5 | 21.0 | 17.9 | 21.0 | 16.7 | 20.0 | 21.2 | 28.4 |
| Solvent | 35.0 | 29.0 | 27.0 | 26.0 | 24.0 | 22.0 | 15.0 | 12.0 |
| Excipients | 2.0 | 1.0 | 2.1 | 2.0 | 2.8 | 2.0 | 3.0 | 4.5 |
| Relational Ratios | | | | | | | | |
| Gelatin:Plasticizer | 3.1 | 2.7 | 2.3 | 1.8 | 1.5 | 1.2 | 1.2 | 0.8 |

Example 4

Exemplary soft lozenges can be prepared by rotary die encapsulation using the fill composition in Table 13 with the shell compositions shown in Tables 10 or 12. The weight of the fill is 2000 mg and the shell is 1162.7 mg. The total weight of the soft lozenge is 3162.7 mg. After drying, the final mass of the soft lozenge is about 2800 mg. About 300-400 mg of water is evaporated during drying (~9-10% water lost).

TABLE 13

Exemplary Soft Lozenge Fill Compositions

| Ingredient | Weight Percent (%) | | | | | | | |
|---|---|---|---|---|---|---|---|---|
| | EX1 | EX2 | EX3 | EX4 | EX5 | EX6 | EX7 | EX8 |
| Gelatin, 150 Bloom | 7.5 | 7.5 | 7.5 | 7.5 | 7.5 | 7.5 | 7.5 | 7.5 |
| Polyethylene Oxide, 4,000,000 MW, (e.g., Polyox ® WSR-303) | — | 4.6 | — | — | — | — | — | — |

TABLE 13-continued

Exemplary Soft Lozenge Fill Compositions

| | Weight Percent (%) | | | | | | | |
|---|---|---|---|---|---|---|---|---|
| Ingredient | EX1 | EX2 | EX3 | EX4 | EX5 | EX6 | EX7 | EX8 |
| Polyethylene Oxide, 5,000,000 MW | — | — | 4.0 | 3.5 | — | — | — | — |
| Polyethylene Oxide, 7,000,000 MW | 2.8 | — | — | — | 4.0 | — | — | 3.2 |
| Polyethylene Oxide, 10,000,000 MW | — | — | — | — | — | 2.5 | 2.1 | — |
| Glycerol | 7.5 | 7.5 | 7.5 | 7.5 | 7.5 | 7.5 | 7.5 | 7.5 |
| Citric Acid | 1.0 | 1.0 | 1.0 | 1.0 | 1.0 | 1.0 | 1.0 | 1.0 |
| Maltitol (75% solution; e.g., Lycasin ® 80/55) | 57.9 | 56.1 | 56.7 | 57.2 | 56.7 | 58.2 | 58.6 | 57.5 |
| Xylitol | 4.3 | 4.3 | 4.3 | 4.3 | 4.3 | 4.3 | 4.3 | 4.3 |
| Sucralose | 0.3 | 0.3 | 0.3 | 0.3 | 0.3 | 0.3 | 0.3 | 0.3 |
| Polysorbate 80 (e.g., Tween ® 80) | 0.7 | 0.7 | 0.7 | 0.7 | 0.7 | 0.7 | 0.7 | 0.7 |
| Water | 18.0 | 18.0 | 18.0 | 18.0 | 18.0 | 18.0 | 18.0 | 18.0 |
| Fluticasone propionate | 0.025 | 0.025 | 0.025 | 0.025 | 0.025 | 0.025 | 0.025 | 0.025 |
| TOTAL | 100.0 | 100.0 | 100.0 | 100.0 | 100.0 | 100.0 | 100.0 | 100.0 |
| Subcomponent Totals | | | | | | | | |
| Film-forming Polymer | 7.5 | 7.5 | 7.5 | 7.5 | 7.5 | 7.5 | 7.5 | 7.5 |
| Release Modifier | 2.8 | 4.6 | 4.0 | 3.5 | 4.0 | 2.5 | 2.1 | 3.2 |
| Plasticizer | 7.5 | 7.5 | 7.5 | 7.5 | 7.5 | 7.5 | 7.5 | 7.5 |
| pH Modifier | 1.0 | 1.0 | 1.0 | 1.0 | 1.0 | 1.0 | 1.0 | 1.0 |
| Sweetener | 62.5 | 60.7 | 61.3 | 61.8 | 61.3 | 62.8 | 63.2 | 62.1 |
| Solubilizing Agent | 0.7 | 0.7 | 0.7 | 0.7 | 0.7 | 0.7 | 0.7 | 0.7 |
| Solvent | 18.0 | 18.0 | 18.0 | 18.0 | 18.0 | 18.0 | 18.0 | 18.0 |
| API | 0.025 | 0.025 | 0.025 | 0.025 | 0.025 | 0.025 | 0.025 | 0.025 |
| Relational Ratios | | | | | | | | |
| API:Total Fill Composition | $2.5E^{-4}$ | $2.5E^{-4}$ | $2.5E^{-4}$ | $2.5E^{-4}$ | $2.5E^{-4}$ | $2.5E^{-4}$ | $2.5E^{-4}$ | $2.5E^{-4}$ |
| PEO:Gelatin | 0.373 | 0.613 | 0.533 | 0.467 | 0.533 | 0.333 | 0.280 | 0.427 |
| PEO:Plasticizer | 0.373 | 0.613 | 0.533 | 0.467 | 0.533 | 0.333 | 0.280 | 0.427 |
| Gelatin:Plasticizer | 1.0 | 1.0 | 1.0 | 1.0 | 1.0 | 1.0 | 1.0 | 1.0 |

Example 5

Exemplary soft lozenges can be prepared by rotary die encapsulation using compositions shown in Table 14. The weight of the fill is 2000 mg and the shell is 1162.7 mg. The total weight of the soft lozenge is 3162.7 mg. After drying, the final mass of the soft lozenge is about 2800 mg. About 300-400 mg of water is evaporated during drying (~9-10% water lost).

TABLE 14

Exemplary Soft Lozenge Total Compositions (Shell and Fill)

| | Weight Percent (%) | | | | | | | |
|---|---|---|---|---|---|---|---|---|
| Ingredient | EX1 | EX2 | EX3 | EX4 | EX5 | EX6 | EX7 | EX8 |
| Gelatin, 150 Bloom | 11.70 | 12.33 | 11.07 | 12.65 | 10.12 | 7.59 | 5.06 | 11.54 |
| Gelatin, 100 Bloom | 4.74 | 3.79 | 5.06 | 3.16 | 6.32 | 9.49 | 11.38 | 4.90 |
| Gelatin hydrolysate | 0.89 | 0.63 | 0.95 | 0.32 | 0.79 | 0.47 | 0.89 | 0.79 |
| PEO, $1 \times 10^6 - 7 \times 10^6$ MW | 1.90 | 1.58 | 2.06 | 2.21 | 1.96 | 1.74 | 1.90 | 2.02 |
| Glycerol | 13.12 | 12.65 | 13.28 | 13.12 | 12.96 | 13.28 | 13.03 | 13.60 |
| Citric Acid | 0.85 | 0.76 | 0.95 | 0.79 | 1.26 | 0.89 | 0.82 | 0.79 |
| Maltitol (e.g., Lycasin ® 80/55) | 41.53 | 44.24 | 41.29 | 42.94 | 41.46 | 41.43 | 42.12 | 41.39 |
| Xylitol | 3.64 | 3.16 | 3.79 | 3.48 | 4.11 | 3.95 | 3.64 | 3.16 |
| Sucralose | 0.25 | 0.22 | 0.28 | 0.19 | 0.25 | 0.22 | 0.21 | 0.32 |
| Polysorbate 80 | 0.44 | 0.38 | 0.32 | 0.41 | 0.25 | 0.47 | 0.41 | 0.51 |
| Water | 20.49 | 20.24 | 20.55 | 20.39 | 19.92 | 20.24 | 20.08 | 20.55 |
| Fluticasone propionate | 0.01 | 0.02 | 0.02 | 0.03 | 0.05 | 0.02 | 0.03 | 0.02 |
| Titanium dioxide | 0.38 | 0.00 | 0.32 | 0.25 | 0.47 | 0.19 | 0.40 | 0.35 |
| Coloring (FD&C dyes) | $6.3E^{-4}$ | 0.00 | $4.7E^{-4}$ | $6.3E^{-4}$ | $6.3E^{-4}$ | $3.2E^{-4}$ | $4.7E^{-4}$ | $6.3E^{-4}$ |
| Flavoring (e.g., cherry, orange) | 0.06 | 0.00 | 0.06 | 0.05 | 0.06 | 0.03 | 0.05 | 0.06 |
| TOTAL | 100.0 | 100.0 | 100.0 | 100.0 | 100.0 | 100.0 | 100.0 | 100.0 |
| Subcomponent Totals | | | | | | | | |
| Film-forming Polymers | 17.33 | 16.76 | 17.07 | 16.13 | 17.23 | 17.55 | 17.33 | 17.23 |
| Release Modifiers | 1.90 | 1.58 | 2.06 | 2.21 | 1.96 | 1.74 | 1.90 | 2.02 |

TABLE 14-continued

Exemplary Soft Lozenge Total Compositions (Shell and Fill)

| | Weight Percent (%) | | | | | | | |
|---|---|---|---|---|---|---|---|---|
| Ingredient | EX1 | EX2 | EX3 | EX4 | EX5 | EX6 | EX7 | EX8 |
| Plasticizer | 13.12 | 12.65 | 13.28 | 13.12 | 12.96 | 13.28 | 13.03 | 13.60 |
| pH Modifier | 0.85 | 0.76 | 0.95 | 0.79 | 1.26 | 0.89 | 0.82 | 0.79 |
| Sweetener | 45.42 | 47.62 | 45.37 | 46.61 | 45.82 | 45.60 | 45.96 | 44.86 |
| Solubilizing Agent | 0.44 | 0.38 | 0.32 | 0.41 | 0.25 | 0.47 | 0.41 | 0.51 |
| Solvent | 20.49 | 20.24 | 20.55 | 20.39 | 19.92 | 20.24 | 20.08 | 20.55 |
| API | 0.01 | 0.02 | 0.02 | 0.03 | 0.05 | 0.02 | 0.03 | 0.02 |
| Excipients | 0.44 | 0.00 | 0.38 | 0.30 | 0.54 | 0.22 | 0.44 | 0.41 |
| Relational Ratios | | | | | | | | |
| API:Total Composition | $7.9E^{-5}$ | $1.6E^{-4}$ | $2.4E^{-4}$ | $3.2E^{-4}$ | $4.7E^{-4}$ | $1.6E^{-4}$ | $3.2E^{-4}$ | $2.4E^{-4}$ |
| PEO:Gelatin | 0.109 | 0.094 | 0.120 | 0.137 | 0.114 | 0.099 | 0.109 | 0.117 |
| PEO:Plasticizer | 0.145 | 0.125 | 0.155 | 0.169 | 0.151 | 0.131 | 0.146 | 0.149 |
| Gelatin:Plasticizer | 1.320 | 1.325 | 1.286 | 1.229 | 1.329 | 1.321 | 1.330 | 1.267 |

Example 6

Exemplary soft lozenges comprising fluticasone can be prepared by rotary die encapsulation using compositions shown in Tables 15-16 with two dosage strengths: 0.5 mg or 1.0 mg. The weight of the fill is 2000 mg and the shell is 1162.7 mg. The total weight of the soft lozenge is 3162.7 mg. After drying, the final mass of the soft lozenge is about 2869.5 mg. Accordingly, about 293.2 mg of water is evaporated during drying (~9.3% water lost).

TABLE 15

Exemplary Soft Lozenge Fill Composition

| | 0.5 mg API | | 1.0 mg API | |
|---|---|---|---|---|
| Ingredient | Mass (mg) | Percent Wt (%) | Mass (mg) | Percent Wt (%) |
| Gelatin, 150 Bloom | 150 | 7.5 | 150 | 7.5 |
| Polyethylene Oxide, 7,000,000 MW (e.g., Polyox ® WSR-303) | 60.0 | 3.0 | 60.0 | 3.0 |
| Glycerol | 150 | 7.5 | 150 | 7.5 |
| Citric Acid | 20.0 | 1.0 | 20.0 | 1.0 |
| Maltitol (75% solution; e.g., Lycasin ® 80/55) | 1154.7 | 57.7 | 1154.2 | 57.2 |
| Xylitol (e.g., Xylisorb 300 ®) | 85.0 | 4.3 | 85.0 | 4.3 |
| Sucralose | 5.8 | 0.3 | 5.8 | 0.3 |
| Polysorbate 80 (e.g., Tween ® 80) | 14.0 | 0.7 | 14.0 | 0.7 |
| Water | 360 | 18.0 | 360 | 18.0 |
| Fluticasone propionate | 0.50 | 0.025 | 1.0 | 0.050 |
| TOTAL | 2000 | 100.0% | 2000 | 100.0% |
| Subcomponent Totals | | | | |
| Film-forming Polymer | 150.0 | 7.5 | 150.0 | 7.5 |
| Release Polymer | 60.0 | 3.0 | 60.0 | 3.0 |
| Plasticizer | 150.0 | 7.5 | 150.0 | 7.5 |
| pH Modifier | 20.0 | 1.0 | 20.0 | 1.0 |
| Sweetener | 1245.5 | 62.3 | 1245.0 | 62.3 |
| Solubilizing Agent | 14.0 | 0.7 | 14.0 | 0.7 |
| Solvent | 360.0 | 18.0 | 360.0 | 18.0 |
| API | 0.50 | 0.025 | 1.00 | 0.05 |
| Relational Ratios | | | | |
| API:Total Fill Composition | 0.00025 | 0.00025 | 0.0005 | 0.0005 |
| PEO:Gelatin | 0.4 | 0.4 | 0.4 | 0.4 |
| PEO:Plasticizer | 0.4 | 0.4 | 0.4 | 0.4 |
| Gelatin:Plasticizer | 1.0 | 1.0 | 1.0 | 1.0 |

TABLE 16

Exemplary Soft Lozenge Shell Composition

| Ingredient | Mass (mg) | Percent Wt (%) | Mass (mg) | Percent Wt (%) |
|---|---|---|---|---|
| Gelatin, 150 Bloom | 219.9 | 18.9 | 219.9 | 18.9 |
| Gelatin, 100 Bloom | 149.9 | 12.9 | 149.9 | 12.9 |
| Gelatin Hydrolysate | 27.7 | 2.4 | 27.7 | 2.4 |

TABLE 16-continued

Exemplary Soft Lozenge Shell Composition

| | Mass (mg) | Percent Wt (%) | Mass (mg) | Percent Wt (%) |
|---|---|---|---|---|
| Glycerol | 264.6 | 22.8 | 264.6 | 22.8 |
| Citric Acid, Anhydrous | 6.3 | 0.54 | 6.3 | 0.54 |
| Maltitol (75% solution; e.g., Lycasin ® 80/55) | 161.7 | 13.9 | 163.7 | 14.1 |
| Xylitol (e.g., Xylisorb 300 ®) | 29.1 | 2.5 | 29.1 | 2.5 |
| Sucralose | 2.4 | 0.21 | 2.4 | 0.21 |
| Water | 286.6 | 24.7 | 286.6 | 24.7 |
| Titanium Dioxide | 12.5 | 1.1 | 12.5 | 1.1 |
| Coloring (FD&C dyes) | 0.02 | 0.0017 | 0 | 0 |
| Flavoring (e.g., cherry) | 2.0 | 0.17 | 0 | 0 |
| TOTAL | 1162.7 | 100.0% | 1162.7 | 100.0% |
| Subcomponent Totals | | | | |
| Film-forming Polymer | 397.5 | 34.2 | 397.5 | 34.2 |
| Plasticizer | 264.6 | 22.8 | 264.6 | 22.8 |
| pH Modifier | 6.3 | 0.5 | 6.3 | 0.5 |
| Sweetener | 193.2 | 16.6 | 195.2 | 16.8 |
| Solvent | 286.6 | 24.6 | 286.6 | 24.6 |
| Excipients | 14.5 | 1.2 | 12.5 | 1.1 |
| Relational Ratios | | | | |
| Gelatin:Plasticizer | 1.5 | 1.5 | 1.5 | 1.5 |

TABLE 17

Exemplary Soft Lozenge Total Composition

| | Mass (mg) | Percent Wt (%) | Mass (mg) | Percent Wt (%) |
|---|---|---|---|---|
| Ingredient | | | | |
| Gelatin, 150 Bloom | 369.9 | 11.7 | 369.9 | 11.7 |
| Gelatin, 100 Bloom | 149.9 | 4.7 | 149.9 | 4.7 |
| Gelatin hydrolysate | 27.7 | 0.9 | 27.7 | 0.9 |
| Polyethylene oxide, 7,000,000 MW (e.g., Polyox ® WSR-303) | 60.0 | 1.9 | 60.0 | 1.9 |
| Glycerol | 414.6 | 13.1 | 414.6 | 13.1 |
| Citric Acid | 26.3 | 0.8 | 26.3 | 0.8 |
| Maltitol (75% solution; e.g., Lycasin ® 80/55) | 1316.4 | 41.6 | 1317.9 | 41.7 |
| Xylitol | 114.1 | 3.6 | 114.1 | 3.6 |
| Sucralose | 8.2 | 0.3 | 8.2 | 0.3 |
| Polysorbate 80 | 14.0 | 0.4 | 14.0 | 0.4 |
| Water | 646.6 | 20.4 | 646.6 | 20.4 |
| Fluticasone propionate | 0.5 | 0.016 | 1.0 | 0.032 |
| Titanium dioxide | 12.5 | 0.4 | 12.5 | 0.4 |
| Coloring (FD&C dyes) | 0.02 | 0.0006 | 0.0 | 0 |
| Flavoring (e.g., cherry) | 2.0 | 0.1 | 0 | 0 |
| TOTAL | 3162.7 | 100.0% | 3162.7 | 100.0% |
| Subcomponent Totals | | | | |
| Film-forming Polymer | 547.5 | 17.3 | 547.5 | 17.3 |
| Release Modifier | 60.0 | 1.9 | 60.0 | 1.9 |
| Plasticizer | 414.6 | 13.1 | 414.6 | 13.1 |
| pH Modifier | 26.3 | 0.8 | 26.3 | 0.8 |
| Sweetener | 1438.7 | 45.5 | 1440.2 | 45.5 |
| Solubilizing Agent | 14.0 | 0.4 | 14.0 | 0.4 |
| Solvent | 646.6 | 20.4 | 646.6 | 20.4 |
| API | 0.5 | 0.016 | 1.0 | 0.032 |
| Excipients (opacifier, coloring, flavoring) | 14.5 | 0.5 | 12.5 | 0.4 |
| Relational Ratios | | | | |
| API:Total | 0.00016 | 0.00016 | 0.00032 | 0.00032 |
| PEO:Gelatin | 0.11 | 0.11 | 0.11 | 0.11 |
| PEO:Plasticizer | 0.14 | 0.14 | 0.14 | 0.14 |
| Gelatin:Plasticizer | 1.32 | 1.32 | 1.32 | 1.32 |

Example 7

Manufacturing Process

The soft lozenge compositions described herein were manufactured according to the following processes:

the matrix fill composition is prepared by:
(a) combining gelatin, glycerol, and water and maintaining the mixture at least about 65° C. for at least 5 minutes; adding maltitol syrup to create a fill gel solution;
(b) separately, combining water, xylitol, sucralose, and citric acid together to create a fill sweetener solution;
(c) separately, combining the active pharmaceutical ingredient (API) and polysorbate 80;
(d) combining the API and polysorbate 80 with the fill sweetener solution to create an API solution;
(e) combining the API solution and the fill gel solution;
(f) further mixing the combined API and fill gel solution at least about 65° C. for at least 5 minutes;
(g) slowly introducing solid polyethylene oxide into the combined API and fill gel solution and mixing and deaerating at least about 65° C. for at least 5 minutes to create a matrix fill composition;

the shell gel mass is prepared by:
(h) combining gelatins, glycerol, and water and maintaining the mixture at least about 65° C. for at least 5 minutes; adding maltitol syrup to create a shell gel solution;
(i) separately, combining water, xylitol, sucralose, and citric acid together to create a shell sweetener solution;
(j) combining the shell sweetener solution and shell gel solution and mixing the combined shell sweetener and shell gel solution at least about 65° C. for at least 5 minutes to create a gel mass; and the soft lozenge is prepared by:
(k) casting the shell gel mass into shell films or ribbons using heat-controlled drums or surfaces;
(l) injecting the matrix fill solution between the shell ribbons, and creating soft lozenges using rotary die technology.

Example 8

Soft lozenges as described in Tables 15-17 comprising 1 mg of fluticasone propionate were manufactured and packaged in 30-count HDPE bottles and stored at 30° C. and 65% relative humidity or 40° C. and 75% relative humidity for stability testing. Samples were evaluated at 2-weeks, 1-month, and 2-months after packaging; results are shown in Tables 18-20.

TABLE 18

Stability and Disintegration after storage at 40° C. and 75% relative humidity

| Test | Specification[1] | Initial | 2 weeks | 1 month |
|---|---|---|---|---|
| Physical Description | White, opaque, pillow shape soft gelatin lozenge | Pass | Pass | Pass |
| Physical Evaluation | Passes visual quality inspection: Shell/Color/Print/Shape: meets requirements for abnormalities in capsule shell, capsule seams, color consistency, print, and misshapen units, Sticking/Package Integrity: meets requirements for sticking, nesting, bricking, and package integrity. | Pass | Fail (sticking lozenges) | Fail (sticking/mis-shaped lozenges) |
| Assay | 90.0-110.0% of label claim (0.9-1.1 mg/lozenge) | 96.7% of label claim (1.0 mg/lozenge) | 98.8% of label claim (1.0 mg/lozenge) | 96.1% of label claim (1.0 mg/lozenge) |
| Degradation Products (method 1) | Report Results | EP Impurity A = ND[2]<br>USP Impurity A = ND<br>EP Impurity F = ND<br>RRT 1.23 = ND<br>Total (methods 1 and 2) = NR[3] | EP Impurity A = ND[2]<br>USP Impurity A = ND<br>EP Impurity F = ND<br>RRT 1.23 = ND<br>Total (methods 1 and 2) = NR[3] | EP Impurity A = ND[2]<br>USP Impurity A = ND<br>EP Impurity F = ND<br>RRT 1.23 = ND<br>Total (methods 1 and 2) = NR[3] |
| Degradation Products (method 2) | Report Results | EP Impurity H = NR[3] | EP Impurity H = NR[3] | EP Impurity H = NR[3] |
| Disintegration | Report Results (minutes:seconds) | 39:32, 40:15, 40:24, 40:30, 40:44, 41:51 | 33:00, 33:00, 35:00, 35:00, 35:00, 35:00 | 35:00, 35:00, 38:00, 38:00, 38:00, 40:00 |
| Microbial Limits | Total Plate Count - NMT 1000 cfu/g<br>Yeast & Mold - NMT 100 cfu/g<br>E. coli - Absent<br>Salmonella - Absent | Total Plate Count: <10 cfu/g<br>Yeast & Mold: <10 cfu/g<br>E. coli: Absent<br>Salmonella: | Not Scheduled | Not Scheduled |

TABLE 18-continued

Stability and Disintegration after storage at 40° C. and 75% relative humidity

| Test | Specification[1] | Initial | 2 weeks | 1 month |
|---|---|---|---|---|
| | S. aureus - Absent<br>P. aeruginosa - Absent | | Absent<br>S. aureus: Absent<br>P. aeruginosa:<br>Absent | |

[1] Use current version of method or compendium.
[2] None detected.
[3] Not reported (reporting limit = 0.05%).

TABLE 19

Stability and Disintegration after storage at 40° C. and 75% relative humidity

| Test | Specification[1] | Initial | 2 months |
|---|---|---|---|
| Physical Description | White, opaque, pillow shape soft gelatin lozenge | Pass | Pass |
| Physical Evaluation | Passes visual quality inspection: Shell/Color/Print/Shape: meets requirements for abnormalities in capsule shell, capsule seams, color consistency, print, and misshapen units. Sticking/Package Integrity: meets requirements for sticking, nesting, bricking, and package integrity. | Pass | Fail (sticking & misshapen lozenges) |
| Assay | 90.0-110.0% of label claim (0.9-1.1 mg/lozenge) | 96.7% of label claim (1.0 mg/lozenge) | 97.9% of label claim (1.0 mg/lozenge) |
| Degradation Products (method 1) | Report Results | EP Impurity A = ND[2]<br>USP Impurity A = ND<br>EP Impurity F = ND<br>RRT 1.23 = ND<br>Total (methods 1 and 2) = NR[3] | EP Impurity A = ND[2]<br>USP Impurity A = ND<br>EP Impurity F = ND<br>RRT 1.23 = ND<br>Total (methods 1 and 2) = NR[3] |
| Degradation Products (method 2) | Report Results | EP Impurity H = NR[3] | EP Impurity H = NR[3] |
| Disintegration | Report Results (minutes:seconds) | 39:32, 40:15, 40:24, 40:30, 40:44, 41:51 | 36:00, 38:00, 38:00, 41:00, 41:00, 48:00 |
| Microbial Limits | Total Plate Count - NMT 1000 cfu/g<br>Yeast & Mold - NMT 100 cfu/g<br>E. coli - Absent<br>Salmonella - Absent<br>S. aureus - Absent<br>P. aeruginosa - Absent | Total Plate Count: <10 cfu/g<br>Yeast & Mold: <10 cfu/g<br>E. coli: Absent<br>Salmonella: Absent<br>S. aureus: Absent<br>P. aeruginosa: Absent | Not Scheduled |

[1] Use current version of method or compendium.
[2] None detected.
[3] Not reported (reporting limit = 0.05%).

TABLE 20

Stability and Disintegration after storage at 30° C. and 65% relative humidity

| Test | Specification[1] | Initial | 2 weeks | 1 month |
|---|---|---|---|---|
| Physical Description | White, opaque, pillow shape soft gelatin lozenge | Pass | Pass | Pass |
| Physical Evaluation | Passes visual quality inspection: Shell/Color/Print/Shape: meets requirements for abnormalities in capsule shell, capsule seams, color | Pass | Pass | Pass |

TABLE 20-continued

Stability and Disintegration after storage at 30° C. and 65% relative humidity

| Test | Specification[1] | Initial | 2 weeks | 1 month |
|---|---|---|---|---|
| | consistency, print, and misshapen units. Sticking/Package Integrity: meets requirements for sticking, nesting, bricking, and package integrity. | | | |
| Assay | 90.0-110.0% of label claim (0.9-1.1 mg/lozenge) | 96.7% of label claim (1.0 mg/lozenge) | 97.2% of label claim (1.0 mg/lozenge) | 97.7% of label claim (1.0 mg/lozenge) |
| Degradation Products (method 1) | Report Results | EP Impurity A = ND[2] USP Impurity A = ND EP Impurity F = ND RRT 1.23 = ND Total (methods 1 and 2) = NR[3] | EP Impurity A = ND[2] USP Impurity A = ND EP Impurity F = ND RRT 1.23 = ND Total (methods 1 and 2) = NR[3] | EP Impurity A = ND[2] USP Impurity A = ND EP Impurity F = ND RRT 1.23 = ND Total (methods 1 and 2) = NR[3] |
| Degradation Products (method 2) | Report Results | EP Impurity H = NR[3] | EP Impurity H = NR[3] | EP Impurity H = NR[3] |
| Disintegration | Report Results (minutes:seconds) | 39:32, 40:15, 40:24, 40:30, 40:44, 41:51 | 30:00, 30:00, 32:00, 33:00, 33:00, 33:00 | 32:00, 32:00, 35:00, 35:00, 35:00, 35:00 |
| Microbial Limits | Total Plate Count - NMT 1000 cfu/g Yeast & Mold - NMT 100 cfu/g E. coli - Absent Salmonella - Absent S. aureus - Absent P. aeruginosa - Absent | Total Plate Count: <10 cfu/g Yeast & Mold: <10 cfu/g E. coli: Absent Salmonella: Absent S. aureus: Absent P. aeruginosa: Absent | Not Scheduled | Not Scheduled |

[1]Use current version of method or compendium.
[2]None detected.
[3]Not reported (reporting limit = 0.05%).

Example 9

A single-dose, randomized, open-label, crossover, comparative bioavailability and placebo-controlled, double-blind taste-test study of fluticasone 1 mg lozenge and Flovent® HFA 220 μg (swallowed and inhaled) was performed in healthy male and female volunteers under fasting conditions.

The primary objective of this pilot study was to estimate the intrasubject variability of, and to compare the bioavailability of fluticasone administered via a fluticasone 1 mg lozenge and Flovent® HFA 220 μg, swallowed and inhaled (GlaxoSmithKline) in healthy male and non-pregnant female volunteers under fasting conditions.

The secondary objective of this study was to evaluate the taste of the fluticasone and placebo lozenges.

The study was designed as a single-dose, randomized, four-period, three-sequence (comparative BA) and two-sequence (taste test), five-treatment (2 treatments for taste test and 3 treatments for comparative BA), combined comparative bioavailability and double-blind taste-test study.

Twenty-four (24) subjects were enrolled made up of healthy, non-smoking (for at least 6 months prior to first study drug administration), male and non-pregnant female volunteers, between 18 and 65 years, with a body mass index (BMI) within 18.5-29.9 kg/m², inclusive.

The specific drugs tested were (a) Fluticasone Lozenge 1 mg (Banner Life Sciences), (b) Flovent® HFA 220 mcg, Inhalation Aerosol (GlaxoSmithKline NC) and (c) a placebo lozenge, to evaluate the taste difference between the placebo and the Fluticasone lozenge 1 mg.

A taste test study was performed by administering both the test drug 1, 1 mg Fluticasone Lozenge (Banner Lifesciences) and the placebo lozenge.

A comparative bioavailability study was performed using (a) the test drug Fluticasone Lozenge 1 mg (Banner Life Sciences) or a first reference drug (R1), 4×220 μg, inhalation aerosol (for oral ingestion) or a second reference drug (R2) 4×220 mcg, inhalation aerosol (to inhale) in each study period.

Safety monitoring was conducted and the duration of confinement was broken up into four periods of time. Period 1 was from at least ten hours prior to, and until at least eight hours after the first dose administration, for a total of at least 18-hours for study Period 1. Periods 2, 3 and 4 was from at least ten hours prior to dosing until at least 24-hours post-dose, for a total of at least 34-hours for each of three study periods with a minimum of at least four days between each dosing. Vital signs (blood pressure and heart rate) were measured for each period. Period 1 vital signs will be measured at pre-dose and at one, three and eight hours after the first dose. Vital signs for the remaining time periods was measured at pre-dose and at one, three, five, eight and 24 hours after the first dose.

The Principal Investigator/Sub-Investigator was present from approximately 30-minutes prior to dosing until at least four hours after the last subject was dosed in each study period. The Principal Investigator/Sub-Investigator remained on-call throughout the duration of the study.

All blood samples were collected in a 6 mL, pre-chilled, sodium fluoride/potassium oxalate Vacutainer® at the following time intervals for Periods 2, 3 and 4: 0, 0.083, 0.167, 0.333, 0.5, 0.75, 1, 1.25, 1.5, 1.75, 2, 3, 4, 6, 8, 16, 24 and 48-hours post-dose in each study period.

Approximately 353 mL of blood, including ~29 mL for pre- and post-study procedures were drawn. Plasma samples were assayed for fluticasone using a validated analytical method according to the principles of Good Laboratory Practice. The Analysis of Variance (ANOVA) for ln-transformed $AUC_{0\rightarrow\tau}$, and $AUC_{0\rightarrow\infty}$, and untransformed $T_{max}$, $\lambda$, and $t_{1/2}$. $T_{max}$ was also analyzed using an additional non-parametric test (Wilcoxon test). The 90% confidence intervals (CI) for the Test/Reference ratios of geometric means for $AUC_{0\rightarrow\tau}$, $AUC_{0\rightarrow\infty}$, and $C_{max}$ were calculated based on the least square means (LSMEANS) and ESTIMATE of the ANOVA.

Palatability scores were calculated for the lozenges and summarized with descriptive statistics. Within-subject paired differences in characteristic scores between placebo and test lozenges were analyzed using non-parametric Wilcoxon Signed-Rank tests if data permitted.

Taste-Test Study—Period 1

This part of the study was a single-dose, randomized, double-blind, cross-over, single-period, two-sequence, two-treatment taste study of fluticasone lozenge 1 mg (Banner Life Sciences) and placebo lozenge (Banner Life Sciences). In this treatment period, 24 healthy, adult non-smoking (for at least 6 months prior to first drug administration) male and non-pregnant female volunteers were administered 1×1 mg fluticasone propionate lozenge and 1 $AUC_{0\rightarrow\infty}$ placebo lozenge under fasting conditions.

Comparative Bioavailability Study—Periods 2, 3 and 4

This was a single-dose, randomized, open-label, 3-way crossover, three-period, three sequence, three-treatment, single-center, comparative bioavailability study of fluticasone lozenge 1 mg and Flovent® HFA 220 µg, both swallowed and inhaled (GlaxoSmithKline). In 3 separate treatment periods, the 24 healthy, adult non-smoking (for at least 6 months prior to first drug administration) male and non-pregnant female volunteers were administered 1×1 mg fluticasone propionate lozenge, 4×220 µg inhalation aerosol to swallow or 4×220 µg inhalation aerosol to inhale under fasting conditions.

There was at least a 4-day washout period between the study periods. The washout period of at least 4 days was estimated to be adequate in avoiding potential carry-over effects of the preceding treatments. Blood samples were collected in Period 2, Period 3 and Period 4, at pre-dose and at 0.083, 0.167, 0.333, 0.5, 0.75, 1, 1.25, 1.5, 1.75, 2, 3, 4, 6, 8, 16, 24 and 48 hours post dose in each study period.

Study Duration and Confinement

Period 1

Subjects were confined to the clinic from at least 10-hours prior to, and until at least 8-hours after the first dose, for a total of at least 18-hours for study Period 1.

Period 2, Period 3 and Period 4

Subjects were confined to the clinic from at least 10 hours prior to dosing until at least 24-hours post-dose, for a total of at least 34-hours for each study period. Subjects were required to return to the clinical facility for the 48-hour blood draw in study Period 2, Period 3 and Period 4.

Randomization and Blinding

In this study, assignment of two separate treatment groups (randomization scheme) for taste test and comparative BA was generated by a computer program designed and run in SAS® Version 9.4.

Comparative Bioavailability Study

The comparative bioavailability study was open-label, and subjects as well as the study staff will were not blinded to the randomization. The bioanalytical laboratory did not have access to the randomization scheme until the bioanalytical analysis is complete. To avoid any study evaluation bias, the taste test study was double-blinded, where the fluticasone lozenge and its matching placebo were blinded to both subjects and clinic staff in charge of reviewing and evaluating adverse events and safety.

In the taste-test portion of the study, un-blinding was only permitted in case of an emergency involving a subject where it was necessary to know which treatment the subject received prior to the subject receiving medical aid. The investigator and the Sponsor had the ability to un-blind the treatment assignment for subjects enrolled in the study.

Subjects who met the eligibility criteria were randomly assigned equally into both of the following treatment groups:

Period 1: Two Sequence Groups

|  | Period 1 | |
|---|---|---|
| Sequence 1 | T | P |
| Sequence 2 | P | T |

Periods 2, 3 and 4: Three Sequence Groups

|  | Period 2 | Period 3 | Period 4 |
|---|---|---|---|
| Sequence 1 | T | R1 | R2 |
| Sequence 2 | R1 | R2 | T |
| Sequence 3 | R2 | T | R1 |

T = fluticasone lozenge; P = placebo lozenge; R1 = Flovent HFA ingestion; R2 = Flovent HFA inhalation Each subject was scheduled to receive a total of five treatments by the end of the study.

Dosing

Subjects took their assigned formulation after a fast of at least 10-hours at their scheduled time point.

Period 1 (Taste-Test)

The subject received the fluticasone propionate 'test' drug lozenge (T) and the placebo lozenge (P) approximately 2 hours apart. The subject was asked to complete a questionnaire in 3 minutes after administering the lozenge for the initial-taste assessment, and after the lozenge completely disintegrated for after-taste assessment, to evaluate the taste characteristics of the lozenge. Disintegration time should have been documented by clinic staff. The subject was NOT to be informed whether the lozenge had active drug or placebo.

First Dose Administration

Subjects were asked to rinse their mouth with 20 mL of ambient temperature water for approximately five seconds and swallow that water prior to lozenge administration. Subjects were instructed to swallow saliva before dosing. Subsequently, staff placed the lozenge directly on the subject's tongue, and asked the subject to close his/her mouth in a natural way, without swallowing, chewing, biting or breaking the lozenge, to permit complete lozenge disintegration. If the subject chewed or swallowed or moved the study drug before it was completely dissolved, the subject was removed from the study. After subjects indicated complete disintegration of the lozenge (confirmed by visual inspection), they were allowed to swallow. Dosing time was set to the time the lozenge was placed on the subject's tongue. Subjects were instructed to inform study staff when they believed that the lozenge was completely disintegrated.

Visual inspection of the lozenge was conducted by the study staff every two minutes until either disintegration was noted or until the subject alerted the study staff to complete disintegration of the lozenge by raising their hand.

Following completion of the after taste assessment for the first dose, subjects were served two cookies and 50 mL of orange juice. Subjects were also provided with 60 mL of water to rinse the mouth and swallow that water.

Second Dose Administration

Subject fasted for one hour before the second lozenge administration. Subject rinsed the mouth with 20 mL of water for approximately five seconds and swallowed that water prior to lozenge administration. Subjects swallowed saliva before dosing. Staff placed the lozenge directly on the subject's tongue, and asked the subject to close his/her mouth in a natural way, without swallowing, chewing, biting or breaking the lozenge, permitting complete lozenge disintegration. After subjects indicated complete disintegration of the lozenge (confirmed by visual inspection), they were allowed to swallow. After completion of the after-taste assessment for the second lozenge, 60 mL of water was provided to rinse the mouth and subjects swallowed the water.

Following the administration of each lozenge, hands and mouth were checked in order to confirm the consumption.

In the taste test questionnaire, the taste was categorized using a specific scoring grid with values from 1-5 for bitterness, sweetness, mouth feel (grittiness), flavor, and overall acceptability; adapted from Reddy et al, "Evaluation Study of Oral Disintegrating Tablets by Human Volunteers." *Internat. J. Pharm. Science Res.* 1(8):326-346 (2010), which is incorporated by reference herein for such teachings. Three minutes after placing the lozenge on the tongue, the subject recorded their feedback in the table based on a scoring grid. The taste scoring, once completed, was taken from the subject.

Once the lozenge has completely disintegrated, the subject recorded their feedback again in the questionnaire based on the scoring grid. When completing the second scoring grid, subjects were not permitted to see their prior responses.

Period 2, Period 3 and Period 4—Lozenge Administration (Test)

The subjects were instructed by the designated study staff to move his/her tongue around the mouth (front and back part of gums, teeth and palate) two times and document any signs of oral irritation and/or any mouth, tongue or gum ulcer(s) were investigated. Just prior to drug administration, each subject rinsed his/her mouth for approximately 5 seconds with approximately 20 mL of room temperature water, and then swallowed the water. Subjects were instructed to swallow saliva before dosing. Subsequently, staff placed the lozenge directly on the subject's tongue, and asked the subject to close his/her mouth in a natural way, without swallowing, chewing, biting or breaking the lozenge, in order to permit complete lozenge disintegration. If the subject chewed, swallowed, or moved the study drug before it was completely dissolved, the subject was removed from the study. After subjects indicated complete disintegration of the lozenge (confirmed by visual inspection), they were allowed to swallow. Dosing time was set to the time the lozenge was placed on the subject's tongue. Subjects were instructed to inform study staff when they believed that the lozenge had completely disintegrated.

Visual inspection of the lozenge was conducted by the study staff every 2-minutes until either disintegration was noted or until the subject alerted the study staff to complete disintegration of the lozenge by raising their hand. Subjects should refrain from talking until complete disintegration of the lozenge is verified by study staff.

The study staff recorded the actual time of lozenge placement and the actual time of disintegration. Subjects were instructed to notify study staff if the lozenge was accidentally swallowed before it was completely disintegrated. Study staff recorded the time the lozenge was swallowed.

Following the administration of the lozenge, hands and mouth were checked in order to confirm the consumption. Following complete dissolution of the lozenge, the subject rinsed his/her mouth with 60 mL of water and then swallowed the water.

The subject was asked to move his/her tongue around the mouth (front and back part of gums, teeth, and palate) two times.

Reference Drug (R1—FLOVENT® Ingested)

Just prior to drug administration, each subject rinsed his/her mouth for approximately 5 seconds with approximately 20 mL of room temperature water, and then swallowed this water. Subjects were assigned to take four inhalations, swallowed approximately 30 seconds apart. Following the fourth and final inhalation/swallow, the subject rinsed his/her mouth with 60 mL of water and then swallowed the water.

Reference Drug (R2—FLOVENT® Inhaled)

The reference drug was delivered using a "spacer" (also known as aerosol-holding chambers, add-on devices, and spacing devices).

Just prior to drug administration, each subject rinsed his/her mouth for approximately 5 seconds with approximately 20 mL of room temperature water, and then will swallowed this water. Subjects were assigned to take four inhalations, 30 seconds apart. Following the fourth and final inhalation/swallow, the subject rinsed his/her mouth with 60 mL of water and then swallowed the water.

Pharmacokinetic and Palatability Analysis Data Set

Two populations were defined for the final PK and statistical analysis as follows:
1. The PK population includes all subjects for whom PK can be determined following a fluticasone (T) dose and at least 1 reference dose (R1 or R2).
2. The full population is comprises of all subjects who received at least one study dose either placebo or test lozenge. This population was also used for the Taste Test analysis.

Data from subjects who were dismissed/withdrawn or who withdrew was evaluated by a BPSI PK specialist and/or the Sponsor for inclusion in the PK and statistical analysis. Subjects with emesis within 4-hours post-dose from period 2, period 3, and period 4, may have been included in the PK analysis, at the discretion of the pharmacokinetic scientist. All other subject data were reported separately. Non-compliant subject data were not included in the PK population, but will be reported separately.

Analysis of Data

Pharmacokinetic and statistical analysis was performed on all data from all subjects in the PK population. Any bioanalytical and/or PK data from subjects not included in the PK population but in the full population will be reported separately.

The PK and/or statistical analyses outlined in this protocol may be altered with appropriate justification.

Pharmacokinetic Analysis

Pharmacokinetic parameters were calculated using non-compartmental analysis (NCA) method. The following PK parameters were estimated (where possible) for fluticasone:

$C_{max}$ The maximal observed plasma concentration.

$T_{max}$ Time when the maximal plasma concentration is observed.

$AUC_{0 \to \tau}$ Area under the concentration-time curve from time zero until the last measurable concentration or last sampling time t, whichever occurs first. $AUC_{0 \to \tau}$ is estimated using the trapezoidal method.

$AUC_{0 \to \infty}$ Area under the concentration-time curve from time zero to infinity, calculated as $AUC_{0 \to \tau} + C_{last}/\lambda$, where $C_{last}$ is the last measurable concentration.

$\lambda$ Terminal elimination rate constant, estimated by linear regression analysis of the terminal portion of the ln-concentration vs. time plot.

$t_{1/2}$ Terminal elimination half-life, estimated as $\ln(2)/\lambda$.

During PK and statistical analyses, drug concentrations below the lower limit of quantitation (BLQ) of an assay were considered as zero except when they occurred following the appearance of quantifiable concentration in the time course; thereafter they were considered as missing during PK calculations and estimations.

Missed samples and non-reportable concentrations (e.g. quantity not sufficient) from the analytical laboratory were treated as missing in the PK analysis.

The $\lambda$, $t_{1/2}$, and $AUC_{0 \to \infty}$ parameters were estimated for plasma concentration-time profiles where the terminal linear phase was not clearly defined, (i.e. the $R^2$ of the terminal linear regression is not ≥0.700).

Statistical Analysis

The PK and statistical analysis was performed at BPSI using SAS® Version 9.4.

Descriptive statistics (min, max, median, mean, standard deviation, and coefficient of variability) of all PK parameters in the PK population were provided for fluticasone for the Test and Reference products.

ANOVA including sequence, subjects nested within sequence, period, and treatment were performed on the ln-transformed data for $AUC_{0 \to \tau}$, $AUC_{0 \to \infty}$, and $C_{max}$ and on the untransformed data for $T_{max}$, $\lambda$, and $t_{1/2}$. $T_{max}$ were analyzed using an additional non-parametric test (Wilcoxon test).

The 90% CI of the Test/Reference ratios of geometric means for $AUC_{0 \to \tau}$, $AUC_{0 \to \infty}$, and $C_{max}$ were calculated based on the LSMEANS and ESTIMATE of the ANOVA.

The following statistical comparisons were performed:
Treatment T vs. Treatment R1
Treatment T vs. Treatment R2
Treatment R1 vs Treatment R2

Palatability Analyses

Using the full population, palatability of the fluticasone and placebo lozenges was measured as described by Reddy et al, *Internat. J. Pharm. Science Res.* 1(8):326-346 (2010), incorporated by reference herein for these specific teachings. The analysis differs marginally because this study is evaluating only two lozenges (Test and Placebo). Initial and post-dissolution palatability was evaluated on four characteristics: bitterness, sweetness, mouth feel, and pleasantness of flavor. Descriptive statistics of the ordinal characteristic scores (1-5) were presented for the placebo and fluticasone lozenges; the statistics included frequency distributions of the scores, as well as summary statistics (mean, standard deviation.) of the scores. Within-subject paired differences between Placebo and Test scores were evaluated using nonparametric Wilcoxon Signed-Rank tests, assessing the null hypothesis of zero difference in scores.

Additional statistical tests were performed as necessary (e.g., initial vs. post-dissolution scores).

Example 10

Summary of pharmacokinetic parameters from the bioavailability study described in Example 10 are shown in Tables 21 and 22. Plots of mean fasting plasma concentrations versus time are shown in FIG. 1. The quantity of systemic Test fluticasone provided by the pharmaceutical compositions described herein is very low ~10 pg/mL and is about 30-times lower than the Reference.

TABLE 21

Mean Fasting Plasma Concentrations for Fluticasone propionate After Dosing

| | Test | | Reference | |
|---|---|---|---|---|
| Time (h) | Conc. (pg/mL) | Std Dev. | Conc. (pg/mL) | Std Dev. |
| Pre-dosing | 0.07 | 0.28 | 0 | 0 |
| 0.083 | 0.08 | 0.32 | 38.26 | 56.55 |
| 0.167 | 0.09 | 0.32 | 59.67 | 74.26 |
| 0.333 | 0.35 | 0.72 | 110.88 | 108.34 |
| 0.5 | 1.59 | 1.87 | 180.55 | 177.48 |
| 0.75 | 3.41 | 2.46 | 217.10 | 193.06 |
| 1 | 5.64 | 3.81 | 256.39 | 233.54 |
| 1.25 | 7.54 | 4.65 | 272.78 | 223.70 |
| 1.5 | 9.15 | 5.26 | 287.90 | 224.13 |
| 1.75 | 9.95 | 5.34 | 298.25 | 229.88 |
| 2.0 | 10.43 | 5.76 | 308.25 | 245.92 |
| 3.0 | 10.14 | 5.67 | 284.04 | 218.94 |
| 4.0 | 8.73 | 4.82 | 270.80 | 212.48 |
| 6.0 | 5.85 | 2.62 | 183.73 | 145.34 |
| 8.0 | 4.60 | 2.22 | 166.96 | 136.21 |
| 16.0 | 2.58 | 1.12 | 69.52 | 62.88 |
| 24.0 | 1.91 | 1.12 | 42.57 | 38.86 |
| 48.0 | 0.91 | 1.18 | 10.78 | 9.31 |

N = 14 subjects

TABLE 22

Summary of Comparative Bioavailability Analysis for Fluticasone 1 mg Lozenge

Single-dose, randomized, open-label, crossover, comparative bioavailability

Geometric Mean
*Arithmetic Mean
(% CV)

| Sample | $AUC_{0 \to \tau}$ (pg · h/mL) | $AUG_{0 \to \infty}$ (pg · h/mL) | $C_{max}$ (pg/mL) | $T_{max}$ (h)* | $t_{1/2}$ (h)* | $\lambda$ (1/h)* | $AUC_{0 \to \tau}/AUG_{0 \to \infty}$† |
|---|---|---|---|---|---|---|---|
| Reference (R) | 1523.19 3852.78 (81.51) | 1533.60 4045.56 (81.51) | 121.50 322.17 (79.75) | 1.76 (1.00-4.08) | 12.06 (17.05) | 0.0591 (17.96) | 0.9551 (1.49) |

TABLE 22-continued

Summary of Comparative Bioavailability Analysis for Fluticasone 1 mg Lozenge

| Test (T) | 108.91 | 154.56 | 9.06 | 2.00 | 0.0604 | 15.39 | 0.7532 |
|---|---|---|---|---|---|---|---|
| | 125.51 | 157.69 | 10.86 | (1.75-3.00) | (54.01) | (56.78) | (13.79) |
| | (58.11) | (60.75) | (53.39) | | | | |

| | | Ratio of Geometric Means (T:R) | 90% Confidence Interval | Intra-subject CV (%) |
|---|---|---|---|---|
| Test (T) | $AUC_{0 \to \tau}$ | 7.15 | 4.64-11.02 | 55.54 |
| | $AUG_{0 \to \infty}$ | 10.08 | 6.04-16.83 | 63.11 |
| | $C_{max}$ | 7.46 | 4.66-11.95 | 61.25 |

Reference (R): Flovent ® HFA 220 µg (fluticasone propionate 220 µg; Inhalation Aerosol) (GlaxoSmithKline)
Test (T): Fluticasone propionate 1.0 mg lozenge (Banner Life Sciences); see Tables 15 and 17
*Arithmetic mean (% CV) only
†Median and range only Example 11

Palatability Data Assessment

The nonparametric Wilcoxon Signed-Rank Test showed that there were not any statistically significantly differences for scores of bitterness, sweetness, mouth feel, and flavor between Test and Placebo groups for both initial-taste assessment phase and post-dissolution taste assessment phase, respectively. These results show that patients did not detect any difference in taste associated with the fluticasone formulation in lozenge dosage form as described herein as compared to the placebo lozenge lacking fluticasone.

TABLE 23

Summary of P-Values Using Wilcoxon Signed-Rank Test for Differences between Placebo and Test Scores

| Evaluation | Taste Test | P-Value | Significant |
|---|---|---|---|
| Bitter | Initial | 0.8234 | No |
| Sweet | Initial | 0.2100 | No |
| Mouth Feel | Initial | 0.9727 | No |
| Flavor | Initial | 0.6292 | No |
| Bitter | Post-dissolution | 0.8750 | No |
| Sweet | Post-dissolution | 0.2051 | No |
| Mouth Feel | Post-dissolution | 0.4465 | No |
| Flavor | Post-dissolution | 0.2432 | No |

Test: Fluticasone Propionate Lozenge, 1.0 mg; Lot No: 147000651A; (Banner Life Sciences LLC)
Placebo: Fluticasone Propionate Lozenge Placebo Lot No: 147000655A; (Banner Life Sciences LLC)

Example 11

A non-controlled oral dissolution study was performed where five subjects were given the lozenge of Examples 15 and 17. Subjects were given no instructions or restrictions other than to communicate when their lozenge was completely dissolved without chewing or biting the lozenge. Subjects were provided the lozenge and were asked to place it in their mouth, at which time timing began.

Complete oral dissolution occurred over a range of about 10 to about 15 minutes, with an average oral dissolution time of 12.5 minutes.

What is claimed is:

1. An oral slow releasing, solid, soft lozenge pharmaceutical dosage form comprising a shell encapsulating a semi-solid matrix fill, the shell comprising:
   (a) about 10% to about 60% by mass of one or more gelatins;
   (b) about 5% to about 20% by mass of glycerol;
   (c) about 0.1% to about 5% by mass of citric acid, acetic acid, lactic acid, malic acid, tartaric acid, fumaric acid, or combinations thereof;
   (d) about 10% to about 80% by mass of one or more of maltitol, xylitol, sucralose or combinations thereof; and
   (e) about 5% to about 30% by mass of water; and the matrix comprising:
   (f) about 5% to about 30% by mass of one or more gelatins;
   (g) about 1% to about 5% by mass of one or more polyethylene oxides comprising a molecular weight of about 900,000 to about 8,000,000;
   (h) about 5% to about 20% by mass of glycerol;
   (i) about 0.5% to about 5% by mass of one or more of citric acid, acetic acid, lactic acid, malic acid, tartaric acid, fumaric acid, or combinations thereof;
   (j) about 10% to about 80% by mass of one of maltitol, xylitol, sucralose, or combinations thereof;
   (k) about 0.1% to about 1% by mass of polysorbate 20, polysorbate 40, polysorbate 60, or polysorbate 80;
   (l) about 5% to about 30% by mass of water; and
   (m) about 0.001% to about 5% by mass of one or more active pharmaceutical ingredients.

2. The composition of claim 1, wherein the composition orally dissolves within about 10 to about 15 minutes upon administration to a subject.

3. The composition of claim 1, wherein the composition contacts the oral and esophageal mucosa for at least about 10 minutes after administration to a subject.

4. The composition of claim 1, wherein the composition contacts the oral and esophageal mucosa for about 10 minutes to about 45 minutes after administration to a subject.

5. The composition of claim 1, wherein the composition achieves about 50% dissolution in vitro at pH 7.4 within about 10 to about 30 minutes.

6. The composition of claim 1, wherein the polyethylene oxide comprises a molecular weight ($M_v$) of about 7,000,000.

7. The composition of claim 1, wherein the gelatins comprises one or more of gelatin, partially hydrolyzed gelatin, hydrolyzed gelatin, or combinations thereof.

8. The composition of claim 1, further comprising one or more thickening agents comprising polyacrylic acid, methyl cellulose, alginic acid, chitosan, carboxymethyl cellulose, sodium carboxymethyl cellulose, locust bean gum, xanthum gum, or combinations thereof.

9. The composition of claim 1, wherein the active pharmaceutical ingredient comprises one or more corticosteroids.

10. The composition of claim 1, wherein the active pharmaceutical ingredients comprise one or more of fluticasone, budesonide, salts thereof, or combinations thereof.

11. The composition of claim 1, wherein the active pharmaceutical ingredient comprises fluticasone propionate.

12. The composition of claim 1, wherein the active pharmaceutical ingredient comprises about 0.025% or about 0.05% fluticasone propionate.

13. The composition of claim 1, wherein the active pharmaceutical ingredient comprises about 0.5 mg or about 1.0 mg of fluticasone propionate.

14. The composition of claim 1, wherein the matrix further comprises a second active pharmaceutical ingredient.

15. The composition of claim 14, wherein the second active pharmaceutical ingredient comprises lidocaine, prilocaine, or a combination thereof.

16. The composition of claim 14, wherein the second active pharmaceutical ingredient comprises about 0.5% to about 5% by weight of the matrix of lidocaine, prilocaine, or a combination thereof.

17. A pharmaceutical combination comprising the composition of claim 1 and one or more additional therapeutic compounds.

18. The pharmaceutical combination of claim 17, wherein the one or more additional therapeutic compound comprises calcium hydroxide, magnesium hydroxide, alluminum hydroxide, sodium bicarbonate, calcium carbonate, bismuth subsalicylate, or others; Maalox, Mylanta, Gaviscon, Kaopectate, Pepto-Bismol) sucralfate, esomeprazole, omeprazole, lansoprazole, dexlansoprazole, esomeprazole, pantoprazole, rabeprazole, ilaprazole, cimetidine, ranitidine, famotidine, lafutidine, nizatidine, roxatidine, tiotidine, salmeterol, albuterol, aclidinium, ipratropium, tiotropium, umeclidinium, acrivastine, azelastine, bilastine, brompheniramine, buclizine, bromodiphenhydramine, carbinoxamine, chlorpromazine, cyclizine, chlorphenamine, chlorodiphenhydramine, clemastine, cyproheptadine, dexbrompheniramine, dexchlorpheniramine, dimenhydrinate, dimetindene, diphenhydramine, doxylamine, ebastine, embramine, fexofenadine, hydroxyzine, loratadine, meclozine, mirtazapine, olopatadine, orphenadrine, phenindamine pheniramine, phenyltoloxamine, promethazine, quetiapine, rupatadine, tripelennamine, triprolidine, clobenpropit, ciproxifan, conessine, thioperamide, montelukast, zafirlukast, pranlukast, mepolizumab, reslizumab, omalizumab, infliximab, azathioprine, 6-mercaptopurine, thioguanine, aspirin (acetylsalicylic acid), ibuprofen, naproxen, ketoprofen, celecoxib, diclofenac, amikacin, gentamicin, kanamycin, neomycin, netilmicin, tobramycin, paromomycin, streptomycin, spectinomycin, geldanamycin, herbimycin, rifaximin, loracarbef, ertapenem, doripenem, imipenem/cilastatin, meropenem, cefadroxil, cefazolin, cefalotin, cefalexin, cefaclor, cefamandole, cefoxitin, cefprozil, cefuroxime, cefixime, cefdinir, cefditoren, cefoperazone, cefotaxime, cefpodoxime, ceftazidime, ceftibuten, ceftizoxime, ceftriaxone, cefepime, ceftaroline fosamil, ceftobiprole, teicoplanin, vancomycin, telavancin, dalbavancin, oritavancin, clindamycin, lincomycin, daptomycin, azithromycin, clarithromycin, dirithromycin, erythromycin, roxithromycin, troleandomycin, telithromycin, spiramycin, aztreonam, furazolidone, nitrofurantoin, linezolid, posizolid, radezolid, torezolid, amoxicillin, ampicillin, azlocillin, carbenicillin, cloxacillin, dicloxacillin, flucloxacillin, mezlocillin, methicillin, nafcillin, oxacillin, penicillin G, penicillin V, piperacillin, temocillin, ticarcillin, amoxicillin/clavulanate, ampicillin/sulbactam, piperacillin/tazobactam, ticarcillin/clavulanate, bacitracin, colistin, polymyxin B, ciprofloxacin, enoxacin, gatifloxacin, gemifloxacin, levofloxacin, lomefloxacin, moxifloxacin, nalidixic acid, norfloxacin, ofloxacin, trovafloxacin, grepafloxacin, sparfloxacin, temafloxacin, mafenide, sulfacetamide, sulfadiazine, silver sulfadiazine, sulfadimethoxine, sulfamethizole, sulfamethoxazole, solfanilamide, sulfasalazine, sulfisoxazole, trimethoprim-sulfamethoxazole, sulfamidochrysoidine, demeclocycline, doxycycline, minocycline, oxytetracycline, tetracycline, clofazimine, dapsone, capreomycin, cycloserine, ethambutol, ethionamide, isoniazid, pyrazinamide, rifampicin, rifabutin, rifapentine, streptomycin, arsphenamine, chloramphenicol, fosfomycin, fusidic acid, metronidazole, mupirocin, platensimycin, quinupristin/dalfopristin, thiamphenicol, tigecycline, tinidazole, trimethoprim, or combinations thereof.

19. The pharmaceutical composition of claim 9, wherein the composition is useful for treating a subject suffering from one or more of oral or esophageal inflammation, eosinophilic esophagitis, inflammatory bowel disease involving the esophagus, oral lichen planus, aphthous stomatitis, Crohn's disease, esophageal inflammation secondary to caustic/irritant ingestion, recurrent esophageal strictures of any cause and including irritant ingestion, pill-induced esophagitis, systemic diseases, congential diseases, epidermolysis bullosa, trauma, or post-surgery inflammation odynophagia, acid reflux, dysphagia, oral, esophageal or peptic ulcers, heart burn, chest pain, abdominal pain, nausea, vomiting, coughing, sore throat, decrease in appetite.

20. A method for treating, retarding the progression of, prophylaxis of, delaying the onset of, ameliorating, or reducing the symptoms of one or more of esophageal, oral, or buccal inflammation, eosinophilic esophagitis, oral lichen planus, aphthous stomatitis, odynophagia, acid reflux, dysphagia, oral, esophageal or peptic ulcers, heart burn, chest pain, abdominal pain, nausea, vomiting, coughing, sore throat, decrease in appetite, or failure to thrive, comprising administering to a subject in need thereof the pharmaceutical composition of claim 9.

* * * * *